US012774330B2

(12) United States Patent
Guhan et al.

(10) Patent No.: US 12,774,330 B2
(45) Date of Patent: Oct. 27, 2026

(54) CONTINUOUS MANUFACTURING PROCESS FOR BIOLOGICS MANUFACTURING BY INTEGRATION OF DRUG SUBSTANCE AND DRUG PRODUCT PROCESSES

(71) Applicant: Amgen Inc., Thousand Oaks, CA (US)

(72) Inventors: Subramanian Guhan, Thousand Oaks, CA (US); Malhar R. Ambhaikar, Thousand Oaks, CA (US); Vincent Chai, Thousand Oaks, CA (US); Sai Chakradhar Padala, Thousand Oaks, CA (US); Nitin Rathore, Thousand Oaks, CA (US); Kenneth Shoemaker, Thousand Oaks, CA (US); Benjamin J. Tillotson, Bainbridge Island, WA (US); Balakumar Thangaraj, Lexington, MA (US); Philip Clark, Seattle, WA (US); Ashish Sharma, Lincoln, RI (US); Hann-Chung Wong, Newbury Park, CA (US); John E. Thorup, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1336 days.

(21) Appl. No.: 17/424,547

(22) PCT Filed: Jan. 27, 2020

(86) PCT No.: PCT/US2020/015137

§ 371 (c)(1),
(2) Date: Jul. 21, 2021

(87) PCT Pub. No.: WO2020/159838

PCT Pub. Date: Aug. 6, 2020

(65) Prior Publication Data

US 2022/0119526 A1 Apr. 21, 2022

Related U.S. Application Data

(60) Provisional application No. 62/797,445, filed on Jan. 28, 2019.

(51) Int. Cl.

| | |
|---|---|
| ***C07K 16/28*** | (2006.01) |
| ***A61K 47/26*** | (2006.01) |
| ***B01D 61/14*** | (2006.01) |
| ***B01D 63/02*** | (2006.01) |
| ***C07K 1/36*** | (2006.01) |

(52) U.S. Cl.

CPC .......... *C07K 16/2809* (2013.01); *A61K 47/26* (2013.01); *B01D 61/146* (2022.08); *B01D 63/02* (2013.01); *C07K 1/36* (2013.01); *C07K 2317/31* (2013.01)

(58) Field of Classification Search

None

See application file for complete search history.

(56) References Cited

U.S. PATENT DOCUMENTS

| | | | |
|---|---|---|---|
| 7,118,675 | B2 | 10/2006 | Siwak et al. |
| 7,776,821 | B2 | 8/2010 | Laursen |
| 8,697,847 | B2 | 4/2014 | Arunakumari et al. |
| 9,845,338 | B2 | 12/2017 | Kokke et al. |
| 9,963,516 | B2 | 5/2018 | Zeng et al. |
| 10,513,555 | B2 | 12/2019 | Gardiel et al. |
| 11,590,452 | B2 | 2/2023 | Iwasaki et al. |
| 2006/0051347 | A1 | 3/2006 | Winter |
| 2006/0210557 | A1 | 9/2006 | Luisi et al. |
| 2008/0132688 | A1 | 6/2008 | Zhou |
| 2012/0329092 | A1 | 12/2012 | Goletz et al. |
| 2013/0195888 | A1 | 8/2013 | Wang et al. |
| 2013/0260419 | A1 | 10/2013 | Ransohoff et al. |
| 2014/0271632 | A1 * | 9/2014 | Hossler ................ C12N 5/0018 435/69.6 |
| 2015/0335706 | A1 | 11/2015 | Olbrich et al. |
| 2016/0176921 | A1 | 6/2016 | Rajendran et al. |
| 2016/0289301 | A1 | 10/2016 | Hoang |
| 2017/0015732 | A1 | 1/2017 | Park et al. |
| 2017/0209571 | A1 | 7/2017 | Kanapuram et al. |
| 2017/0218078 | A1 | 8/2017 | Raum et al. |
| 2017/0260498 | A1 | 9/2017 | Mundt et al. |
| 2017/0260763 | A1 | 9/2017 | Fortin et al. |
| 2017/0274299 | A1 | 9/2017 | Coutard |
| 2018/0072769 | A1 | 3/2018 | Olson et al. |
| 2018/0127461 | A1 | 5/2018 | Schwan et al. |
| 2018/0135006 | A1 | 5/2018 | Maiser et al. |
| 2019/0023768 | A1 | 1/2019 | Nadarajah et al. |
| 2020/0094190 | A1 | 3/2020 | Iwasaki et al. |
| 2024/0277805 | A1 | 8/2024 | Haqq et al. |

FOREIGN PATENT DOCUMENTS

| | | |
|---|---|---|
| EP | 2682168 | 1/2014 |
| JP | 2008512473 | 4/2008 |
| JP | 2013501075 | 1/2013 |
| JP | 2013508387 | 3/2013 |
| JP | 2014514345 | 6/2014 |
| JP | 2015536938 | 12/2015 |
| JP | 2017095440 | 1/2017 |
| WO | 2006031560 | 8/2006 |
| WO | 2008/036899 A2 | 3/2008 |
| WO | 2011/031397 A1 | 3/2011 |
| WO | 2011/050071 A2 | 4/2011 |
| WO | 2012/151199 A1 | 11/2012 |
| WO | 2015/192127 A2 | 12/2015 |

(Continued)

OTHER PUBLICATIONS

Allen, "The Evolution of Platform Technologies for the Downstream Processing of Antibodies", Pharma/Biotech Research and Technology, Lonza AG, Slough, UK, 2017, pp. 365-389.

(Continued)

*Primary Examiner* — Marianne P Allen
(74) *Attorney, Agent, or Firm* — Lauren Mangano Drenkard

(57) ABSTRACT

A biologics manufacturing process that connects the drug substance and drug product processes into an integrated, continuous process.

26 Claims, 20 Drawing Sheets

(56) References Cited

FOREIGN PATENT DOCUMENTS

| | | | |
|---|---|---|---|
| WO | 2016005903 | | 1/2016 |
| WO | 2017051273 | | 3/2017 |
| WO | 2017072201 | | 5/2017 |
| WO | 2017/218997 | A2 | 12/2017 |
| WO | 2017218977 | | 12/2017 |
| WO | 2018/152165 | A1 | 8/2018 |
| WO | 2018/183459 | A1 | 10/2018 |
| WO | 2018230397 | | 12/2018 |

OTHER PUBLICATIONS

Ghose, "Integrated Polishing Steps for Monoclonal Antibody Purification", Process Scale Purification of Antibodies, 2017, pp. 304-323.

Johnson, "Virus filtration: A review of current and future practices in bioprocessing", Biotechnology Bioengineering. 2022; 119: pp. 743-761.

Office Action Issued for Japanese Patent Application No. 2021-542380, Mailed Jul. 2, 2024, 6 pages.

Office Action Issued for Brazilian Patent Application No. 11 2021 014634-2, Mailed Feb. 26, 2025, 6 pages.

Viresolve® Pro Solution Performance Guide, EDM Millipore Corporation, 2014, pp. 1-52.

Katz, et al, *Prefiltration and Process Improvements: Enhancing Virus Filter Performance with the Use of Adsorptive Depth or Surface Modified Prefilters*, EDM Millipore Corporation, 2016.

Adamo, et al, *On-demand continuous-flowproduction of pharmaceuticals in a compact, reconfigurable system*, Science, v352 #6281, 2016, pp. 61-67.

Barone, et al, *Biopharmaceutical Industry Approaches to Facility Segregation for Viral Safety: An Effort from the Consortium on Adventitious Agent Contamination in Biomanufacturing*, J Pharm Sci and Tech, v73, 2019, pp. 191-203.

Callahan, et al, *Control of Protein Particle Formation During Ultrafiltration/Diafiltration Through Interfacial Protection*, J Pharmaceutical Science, v103, 2014, pp. 862-869.

Doodeji, et al, *A Review on the Applications of Nanofiltration in Virus Removal and Pharmaceutical Industries*, Glob J Nano. 2018; v3 #5.

Katz, et al, *Developing the biofacility of the future based on continuous processing and single-use technology*, J Biotechnology, v213, 2015, pp. 120-130.

Lee, et al, *Modernizing Pharmaceutical Manufacturing: from Batch to Continuous Production*, J Pharma Innov, v10, 2015, pp. 191-199.

Mattila, et al, *Retrospective Evaluation of Low-pH Viral Inactivation and Viral Filtration Data from a Multiple Company Collaboration*, PDA J Pharm Sci and Tech, v70 #3, 2016, pp. 293-299.

Misra, et al, *A Three Plus Three Parameters Mechanistic Model for Viral Filtration*, Biotechnol. Prog, v36 #6, 2017, pp. 1538-1547.

Poechlauer, et al, *Continuous Processing in the Manufacture of Active Pharmaceutical Ingredients and Finished Dosage Forms: An Industry Perspective*, Am Chemical Society, v16, 2012, pp. 1586-1590.

Rathore, et al., *Current Perspectives on Stability of Protein Drug Products during Formulation, Fill and Finish Operations*, Biotechnol. Prog., v24 #3, 2008, pp. 504-514.

Rayfield, et al, *Prediction of Viral Filtration Performance of Monoclonal Antibodies Based on Biophysical Properties of Feed*, Biotechnol. Prog, v31 #3, 2015, pp. 765-774.

International Search Report for PCT Application No. PCT/US2020/015137, mailed on Jul. 7, 2020.

Warikoo, et al, *Integrated Continuous Production of Recombinant Therapeutic Proteins*, Biotechnology & Bioengineering, v109 #12, 2012, pp. 1-12.

International Written Opinion for PCT Application No. PCT/US2020/015137.

Xue, et al, *Leveraging Allotrope to Holistically Integrate Process Analytics Data for Real Time Process Monitoring and Release Testing*, IPFAC 32$^{nd}$ Annual International Forum and Exhibition Process Analytical Technology, Bethesda, MD., 2018, pp. 1-20.

Clark, et al, *Continuous Manufacturing Using Fully Closed Processing Provides Appropriate Segregation of Pre- and Post-Viral Removal Within the Same Product Manufacturing Suite*, Charles River Viral Safety Summit, San Mateo, CA, 2017, pp. 1-19.

Patent Search Report for Eurasian Patent Application No. 202590765, mailed Sep. 30, 2025.

Office Action for Eurasian Patent Application No. 202590765, Issued Jul. 3, 2025, 4 pages.

CA Office Action Mailed on Jan. 19, 2026 for CA Application No. 3127258, 6 page(s).

EA Office Action Mailed on Apr. 30, 2026 for EA Application No. 202590765, 7 page(s).

EP Office Action Mailed on Nov. 21, 2025 for EP Application No. 20708774, 8 page(s).

IN Office Action Mailed on May 20, 2026 for IN Application No. 202117036594, 15 page(s).

JP Office Action Mailed on Feb. 10, 2026 for JP Application No. 2024195730, 9 page(s).

Observations by third parties Mailed on Sep. 9, 2025 for EP Application No. 20708774, 6 page(s).

* cited by examiner

CONTINUOUS MANUFACTURING PROCESS FOR BIOLOGICS MANUFACTURING BY INTEGRATION OF DRUG SUBSTANCE AND DRUG PRODUCT PROCESSES

This application claims the benefit of U.S. Provisional Application No. 62/797,445 filed Jan. 28, 2019, which is hereby incorporated by reference.

FIELD OF DISCLOSURE

A biologics manufacturing process that connects the drug substance and drug product processes into an integrated, continuous process.

BACKGROUND

Taking a drug substance to drug product fill/finish is typically a two-part process, usually separated at the conversion of drug substance to drug product by a freeze/thaw step. The conversion of purified biopharmaceutical protein of interest to drug substance (DS) and then to drug product (DP) typically involves concentrating the protein of interest to a desired level in a suitable formulation buffer through an ultrafiltration and diafiltration (UFDF) unit operation. Following UFDF, the concentrated, formulated protein is processed by one or more bioburden-reduction filters, typically into a hold vessel. One or more additional excipients, typically to enhance protein stability, are added to the concentrated, formulated protein, now drug substance, which is once again processed by one or more bioburden-reducing filters into sterile containers. The drug substance is typically sampled at this point to test certain drug substance attributes against release specifications. The drug substance is then frozen for storage or for ease of transferring to another manufacturing facility. When needed, the drug substance material is thawed, pooled into a formulation vessel, mixed and processed by one or more bioburden-reduction filters, resulting in filtered bulk drug product. The filtered bulk drug product is then sterile filtered and transferred to a sterile facility for fill/finish operations. An additional round of attribute and/or release assays are repeated at this fill/finish step to assess attributes against release specification and to confirm that the drug product quality/characteristics have not changed after undergoing the drug product preparation process, some of which are common to attribute testing already done to the drug substance.

This process involves duplicated effort that contributes to an increase in manufacturing costs and material waste; multiple hold/store steps that are not compatible with continuous manufacturing platforms; redundant filtration steps, and freeze and thaw unit operations, which all have the potential for drug substance loss and/or destabilization. As such, there is a need for a more cost effective, continuous, integrated conversion purified biopharmaceutical proteins of interest to drug substance and then to drug product that would allow for reduction in the size and quantity of equipment and materials needed and used; which could have the benefit of reducing the footprint of a manufacturing facility or allowing for use of manufacturing pods or other compact systems, reducing the time and cost of establishing and operating manufacturing facilities and consolidation of attribute testing. The invention described herein meets this need by providing a fully integrated, continuous, manufacturing process for biologics manufacturing by integration of drug substance and drug product processes by eliminating and/or combining the process steps from UFDF through drug product fill/finish.

BRIEF SUMMARY OF THE INVENTION

The invention provides an integrated, continuous method for producing a recombinant biologic therapeutic comprising providing a purified recombinant protein of interest; concentrating or diluting the purified recombinant protein by ultrafiltration; buffer exchanging the purified recombinant protein into a desired formulation by diafiltration; further diluting or concentrating the formulated recombinant protein by ultrafiltration until a target concentration is achieved; adding or combining at least one stability-enhancing excipient once the target concentration is achieved; subjecting the resulting bulk drug substance to filtration to reduce bioburden; subjecting the resulting bulk drug product to sterile filtration; and subjecting the sterile bulk drug product to a fill and finish operation; wherein neither the purified recombinant protein nor the bulk drug substance is subjected to freezing and thawing unit operations. In one embodiment the stability-enhancing excipient is added in-line to the formulated recombinant protein. In one embodiment the stability-enhancing excipient is added directly to an ultrafiltration and diafiltration (UFDF) retentate feed tank. In a related embodiment the stability-enhancing excipient is added in-line directly to the UFDF retentate feed tank once the target concentration is achieved. In another embodiment the stability-enhancing excipient is a non-ionic detergent or surfactant. In one embodiment the stability-enhancing excipient is a poly-oxy-ethylene (PEO)-based surfactant. In one embodiment the stability-enhancing excipient is selected from polysorbate 80 and polysorbate 20. In one embodiment the concentration of at least one stability-enhancing excipient is from 0.001 to 0.1% (weight/volume). In one embodiment the bulk drug product is collected in a storage vessel. In one embodiment the bulk drug product is delivered to an aseptic processing facility. In a related embodiment the aseptic processing facility comprises at least one filling station. In another related embodiment the aseptic processing facility comprises at least one gloveless, sterile isolator. In another embodiment the bulk drug product is collected in a storage vessel and delivered directly to the aseptic processing facility. In a related embodiment the storage vessel is connected to the aseptic processing facility. In another related embodiment a storage bag containing the bulk drug product, or the output of a filter processing the bulk drug product, is connected to a gloveless, sterile isolator. In another related embodiment the aseptic processing facility has a connection with a storage vessel containing the bulk drug product, or the output of a filter unit processing the bulk drug product. In one embodiment a primary drug product container is filled with sterile bulk drug product. In a related embodiment the primary drug product container is sealed, labeled and packaged. In one embodiment there is a continuous flow between one or more steps. In one embodiment the pool from UFDF and/or bioburden-reduction filtration is collected into a storage vessel. In one embodiment the formulated recombinant protein is diluted until a target concentration is achieved. In one embodiment the formulated recombinant protein is concentrated by ultrafiltration until a target concentration is achieved. In one embodiment the ultrafiltration is performed using a stabilized cellulose based hydrophilic membrane, loading up to 72 $g/m^2$ of membrane area. In one embodiment the ultrafiltration is performed using a stabilized based hydrophilic membrane at target concentration less than or equal to 3.20 mg/ml. In one embodiment the ultrafiltration is performed using a stabilized cellulose based hydrophilic membrane at a target overconcentration of 1.1× to 2.5× the initial concentration. In one embodiment the ultrafiltration and diafiltration is performed using a regenerated cellulose, alkali stable membrane loaded up to 170 g/$m^2$ of membrane area. In one embodiment 1 the ultrafiltration and diafiltration is performed using a regenerated cellulose, alkali stable membrane at an intermediate target overconcentration of less than or equal to 9 g/L with up to 13 diavolumes. In one embodiment the method described herein further comprises at least one viral filtration operation. In one embodiment at least one viral filtration operation follows the UFDF operation. In a related embodiment at least one viral filtration operation follows the in-line addition of the stability-enhancing excipient to the formulated recombinant protein or the addition of the stability-enhancing excipient stability-enhancing excipient to the UFDF retentate tank. In one embodiment a bispecific T cell engager having a formulation concentration of 5 g/L or less is subjected to the viral filtration operation. In one embodiment the viral filter is selected from a hydrophilized polyvinylidene fluoride (PVDF) hollow fiber filter, a cuprammonium-regenerated cellulose hollow fiber filter, or a polyethersulfone (PES) parvovirus retentive filter. In another related embodiment at least one viral filtration operation also includes a prefilter. In another related embodiment the prefilter is a depth filter. In one embodiment one or more additional purified recombinant proteins of interest or drug substances are added prior to sterile filtration. In one embodiment the purified protein of interest is an antigen-binding protein. In one embodiment the antigen-binding protein is a multispecific protein. In one embodiment the multispecific protein is a bispecific antibody. In one embodiment the bispecific protein is a bispecific T cell engager. In one embodiment the bispecific T cell engager is a half life extended bispecific T cell engager. In a related embodiment one binding domain of the bispecific T cell engager is specific for a tumor-associated surface antigen on target cell selected from EGFRvIII, MSLN, CDH19, DLL3, CD19, CD33, CD38, FLT3, CDH3, BCMA, PSMA, MUC17, CLDN18.2, or CD70. In a related embodiment the bispecific T cell engager is selected from blinatumomab, pasotuxizumab, AMG103, AMG330, AMG212, AMG160, AMG420, AMG-110, AMG562, AMG596, AMG427, AMG673, AMG675, or AMG701.

The invention also provides a pharmaceutical composition comprising the drug product from the method described herein.

The invention also provides a method for producing a recombinant protein drug product comprising expanding cells expressing a protein of interest to the N−1 stage; inoculating and/or feeding a bioreactor with the expanded cells and cultivating the cells to express a recombinant protein of interest; recovering the recombinant protein through a harvest unit operation; purifying the harvested recombinant protein through at least one capture chromatography unit operation; purifying the recombinant protein through at least one polish chromatography unit operation; subjecting the purified recombinant protein to an ultrafiltration and diafiltration unit operation comprising concentrating or diluting the purified recombinant protein by ultrafiltration; buffer exchanging the purified recombinant protein into a desired formulation by diafiltration; further diluting or concentrating the formulated purified recombinant protein by ultrafiltration until a target concentration is achieved, adding one or more stability-enhancing excipients directly to the UFDF retentate feed tank containing the formulated purified recombinant protein resulting in formulated drug substance; subjecting the formulated drug substance to a single unit operation to reduce bioburden resulting in filtered bulk drug product sterile filtering the bulk drug product; filling a primary drug product container with sterile bulk drug product; and sealing, labeling and packaging the primary drug product container; wherein neither the recombinant protein nor the drug substance is subjected to freezing and thawing unit operations.

The invention also provides a pharmaceutical composition comprising the recombinant protein drug product of the method described herein.

The invention also provides a method for reducing the manufacturing footprint for drug product production process comprising subjecting a purified recombinant protein of interest to an ultrafiltration and diafiltration (UFDF) unit operation until a target concentration has been achieved; adding at least one stability-enhancing excipient directly to the UFDF retentate feed tank; subjecting the bulk drug substance to a single unit operation to reduce bioburden followed by sterile filtration; subjecting the sterile bulk drug product to a fill and finish unit operation; wherein neither the recombinant protein nor the drug substance is subjected to freezing and thawing unit operations. In one embodiment the storage vessel containing the bulk drug product is connected to an aseptic processing facility. In one embodiment an aseptic processing facility has a connection with a storage vessel containing, or the output of a filter processing, the bulk drug product. In one embodiment there is a continuous flow between one or more steps. In one embodiment at least one viral filtration unit operation follows the UFDF unit operation.

The invention also provides a method for reducing drug substance loss and/or destabilization during recombinant therapeutic protein manufacturing comprising subjecting a purified recombinant protein of interest to a UFDF unit operation; adding at least one stability-enhancing excipient to the UFDF retentate feed tank once a target concentration has been achieved; subjecting the UFDF pool to a single filtration to reduce bioburden resulting in bulk drug substance; wherein neither the recombinant protein nor the drug substance is subjected to freezing and thawing unit operations.

The invention also provides a method for reducing viral contaminants in a composition comprising a recombinant bispecific T cell engager comprising providing a sample comprising less than 7.0 g/L of a recombinant bispecific T cell engager at a pH less than or equal to 6.0, having a conductivity of 23-45 mS/cm; subjecting the sample to a virus filtration unit operation comprising a viral filter alone or in combination with a depth filter or surface modified membrane prefilter; and collecting the viral filter eluate comprising the recombinant bispecific T cell engager, in a pool or as a stream. In one embodiment the bispecific T-cell engager is a half-life extended bispecific T cell engager. In one embodiment the sample comprises a chromatography column pool or effluent stream. In one embodiment the pH of the pool or stream is 4.2-6.

The invention also provides a purified, recombinant half-life extended bispecific T cell engager produced according to the method described herein.

The invention also provides a method for decreasing high molecular weight species during manufacture of a recombinant bispecific T cell engager comprising providing a sample comprising less than 7 g/L recombinant bispecific T cell engager, at a pH less than or equal to 6.0, having a conductivity of 23-45 mS/cm; subjecting the sample to a virus filtration unit operation comprising a viral filter in combination with a depth filter; and collecting the viral filter eluate in a pool or as a stream; wherein the percentage of high molecular weight species in the filter eluate pool is decreased compared to use of a virus filtration unit operation comprising a viral filter alone or in combination with a surface modified membrane prefilter. In one embodiment the bispecific T-cell engager is a half-life extended bispecific T cell engager.

The invention also provides a method for decreasing flux decay and reducing high molecular weight species in a virus filtration unit operation during manufacture of a recombinant bispecific T cell engager comprising providing a sample comprising less than or equal to 1.75 g/L of a recombinant bispecific T cell engager at a pH of 4.2-6.0, the conductivity is 23-45 mS/cm; subjecting the purified recombinant bispecific T cell engager to a virus filtration unit operation comprising a viral filter in combination with a depth filter; and collecting the filter eluate in a pool or as a stream; wherein the percentage of high molecular weight species in the filter eluate pool or stream is decreased compared to a virus filtration unit operation comprising a viral filter alone or in combination with a surface modified membrane prefilter. In one embodiment the bispecific T-cell engager is a half-life extended bispecific T cell engager.

The invention also provides a method for producing a purified, formulated recombinant bispecific T cell engager, the method comprising purifying a harvested recombinant bispecific T cell engager through one or more chromatography unit operations; subjecting the purified recombinant bispecific T cell engager to an ultrafiltration and diafiltration unit operation resulting in a formulated bispecific T cell engager at a concentration of ≤5 g/L and subjecting the formulated bispecific T cell engager to a viral filtration unit operation; obtaining a purified, formulated recombinant bispecific T cell engager. In one embodiment in the formulated bispecific T cell engager is at a concentration of ≤3.2 g/L. In one embodiment the formulated bispecific T cell engager is at a concentration of ≤1.79 g/L. In one embodiment the bispecific T-cell engager is a half-life extended bispecific T cell engager. In one embodiment the ultrafiltration diafiltration unit operation is performed with a stabilized cellulose based hydrophilic membrane or a regenerated cellulose membrane. In one embodiment the ultrafiltration diafiltration unit operation is performed with a stabilized cellulose based hydrophilic membrane loaded up to 71.4 $g/m^2$ of membrane area at an initial ultrafiltration target concentration up to 3.20 g/L. In one embodiment the ultrafiltration diafiltration unit operation is performed with a regenerated cellulose membrane loaded up to 170 $g/m^2$ of membrane area with an intermediate target overconcentration up to 9 g/L with up to 13 diavolumes. In one embodiment the viral filtration unit operation is performed with a hydrophilized polyvinylidene fluoride (PVDF) hollow fiber filter, cuprammonium-regenerated cellulose hollow fiber filter, or a polyethersulfone (PES) parvovirus retentive filter. In one embodiment the viral filtration unit operation is performed using a cuprammonium-regenerated cellulose hollow fiber filter and a formulated bispecific T cell engager at a concentration of ≤3.2 g/L. In one embodiment the formulated bispecific T cell engager is at a concentration of ≤1.79 g/L. In one embodiment the viral filtration unit operation is performed using a hydrophilized polyvinylidene fluoride (PVDF) hollow fiber filter and a formulated bispecific T cell engager at a concentration of ≤1.79 g/L.

BRIEF DESCRIPTION OF THE DRAWINGS

FIG. 4: Product quality data cuprammonium-regenerated cellulose filter pH 4.2 centerpoint [black bars], pH 4.2 high concentration [grey bars], pH 4.2 extended hold [white no fill bars], pH 4.2 high volume [solid diamond grid bars], pH 4.2 PVDF filter [patterned circle bars], pH 5.0 low concentration [square grid bars].

FIG. 6: Product quality data for Molecule A in chromatography buffer matrix runs—1.77 g/L, pH 5, 23 High pressure [black bars], 3.2 g/L, pH 5, 23 [grey bars], 1.77 g/L, pH 5, 28 [white no fill bars], 1.77 g/L, pH 5, 23 Low pressure [dotted circle bars], 6.82 g/L, pH 5.3, 28 [square grid bars], 6.82 g/L, pH 4.5, 28 [light grey bars], 1.77 g/L, pH 5, 23, Medium pressure [solid diamond grid bars].

B: HMW % Product quality data for Molecule A—7 g/L, pH 6 [black bars], and pH 4.2 [grey bars].

C: Rce (Clips %) Product quality data for Molecule A—1.75 g/L, pH 5 [black bars], pH 4.2 [grey bars] and pH 6.0 [patterned bars]

D: Rce (Clips %) Product quality data for Molecule A—7 g/L, pH 6.0 [black bars], and pH 4.2 [grey bars]

E: CEX Acidic (%) Product quality data for Molecule A—1.75 g/L, pH 5 [black bars], 4.2 [grey bars] and 6.0 [patterned bars].

F: CEX Basic (%) Product quality data for Molecule A—1.75 g/L, pH 5 [black bars], pH 4.2 [grey bars] and pH 6.0 [patterned bars].

G: CEX Acidic (%) Product quality data for Molecule A—7 g/L, pH 6 [black bars], and pH 4.2 [grey bars].

H: CEX Basic (%) Product quality data for Molecule A—7 g/L, pH 6 [black bars], and pH 4.2 [grey bars].

Figure 11:
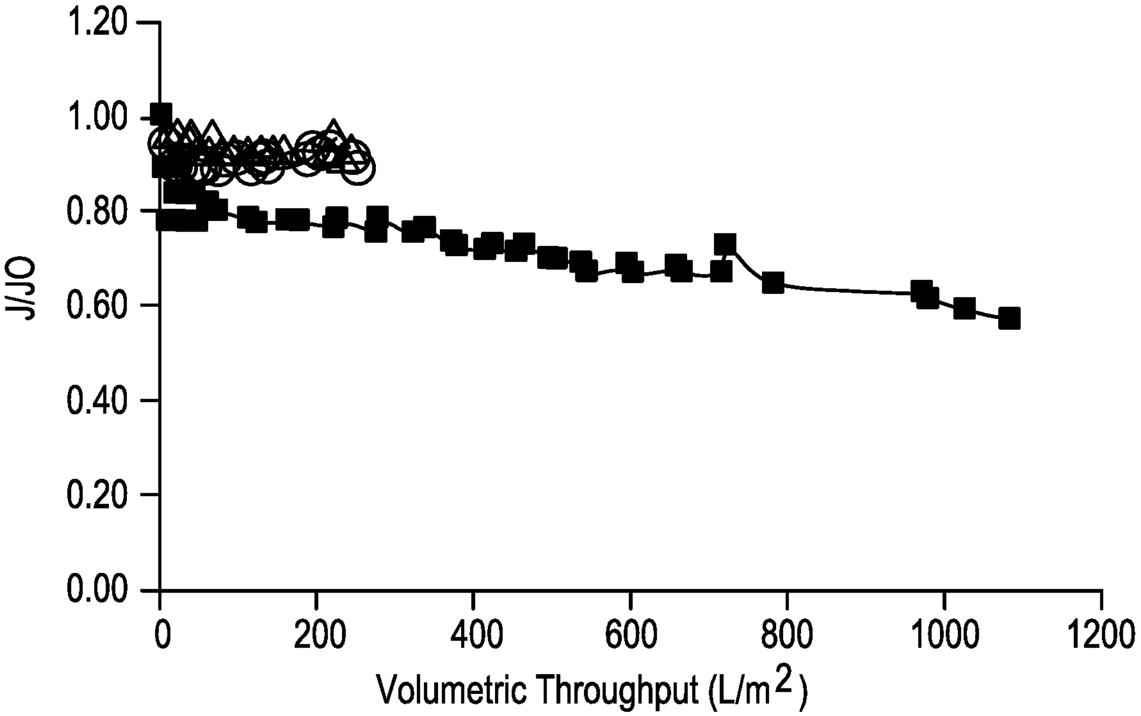

FIG. 11: Hydraulic performance at midpoint pH and concentration between the mAb [solid squares] and 1) BiTE® A X0SP/VPro [grey triangle], 2) BiTE® A VPF/VPro [open black circles].

Figure 12:
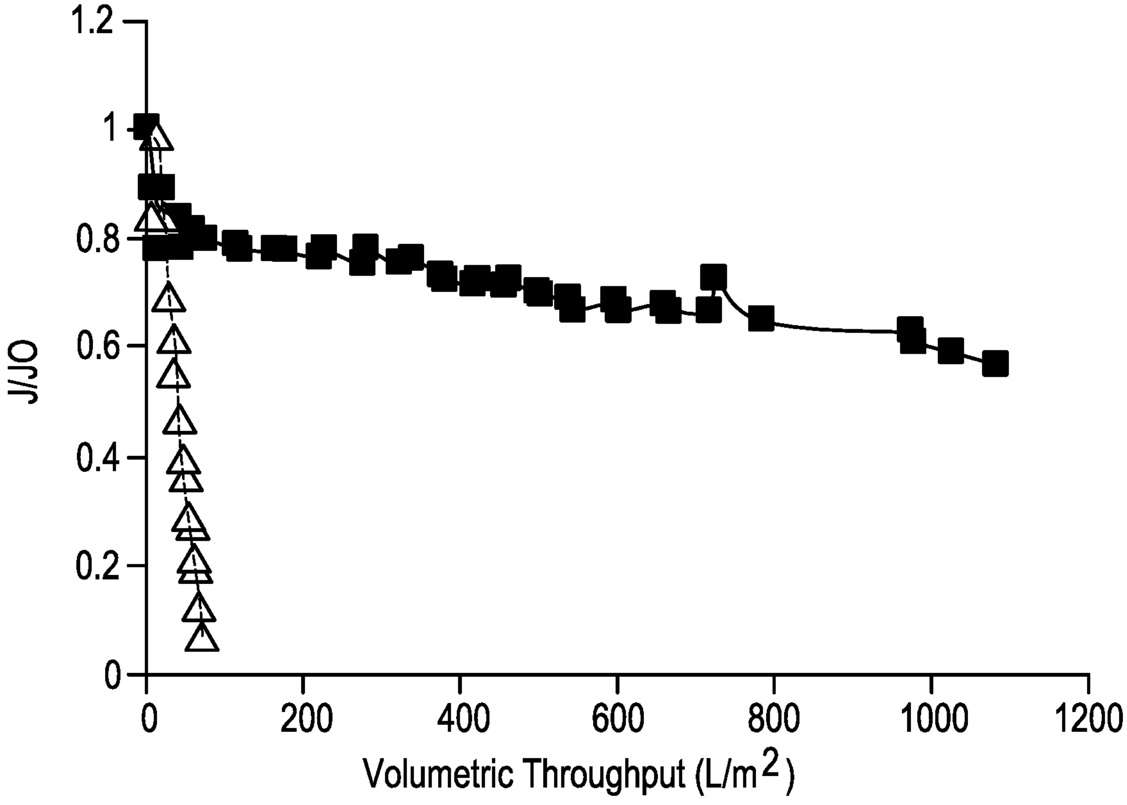

FIG. 12: Hydraulic performance at high pH and high concentration between the mAb [Solid squares] and BiTE® A X0SP/VPro [grey triangle].

Figure 13:
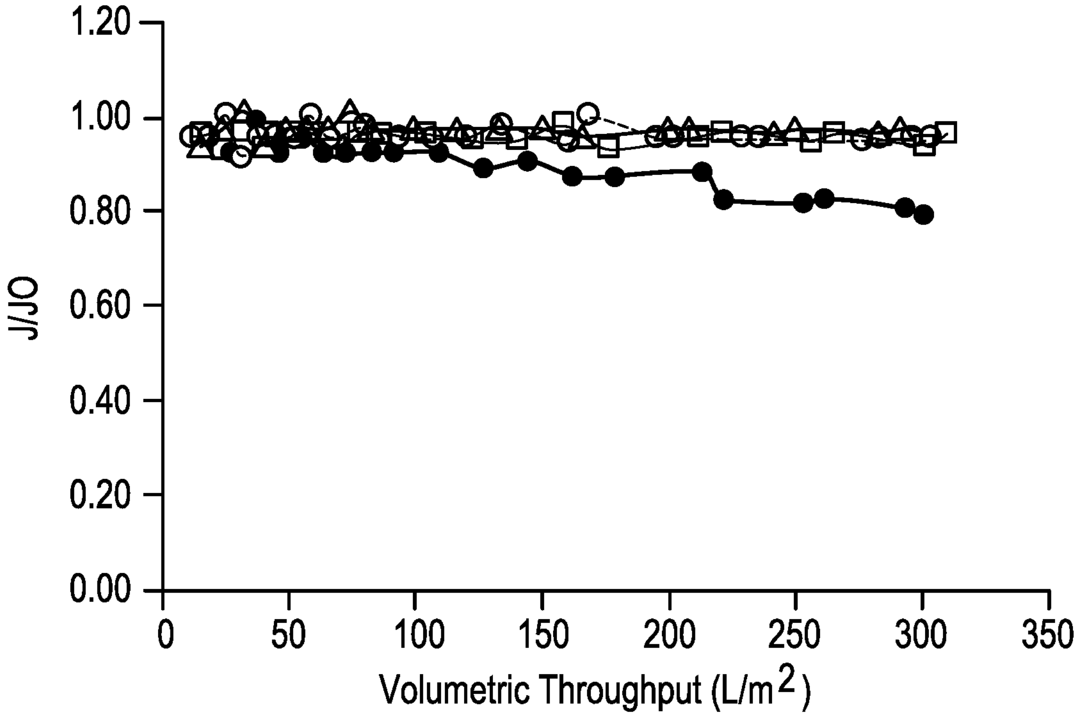

FIG. 13: BiTE® B Hydraulic Performance at pH 5.9, 31 mS/cm, 1.8 g/L, VPro alone [solid black circle], VPro+Shield [solid black triangle], VPro+Shield H [open square], and VPro+VPF [solid grey circles], and VPro+X0SP [open black triangle].

Figure 14:
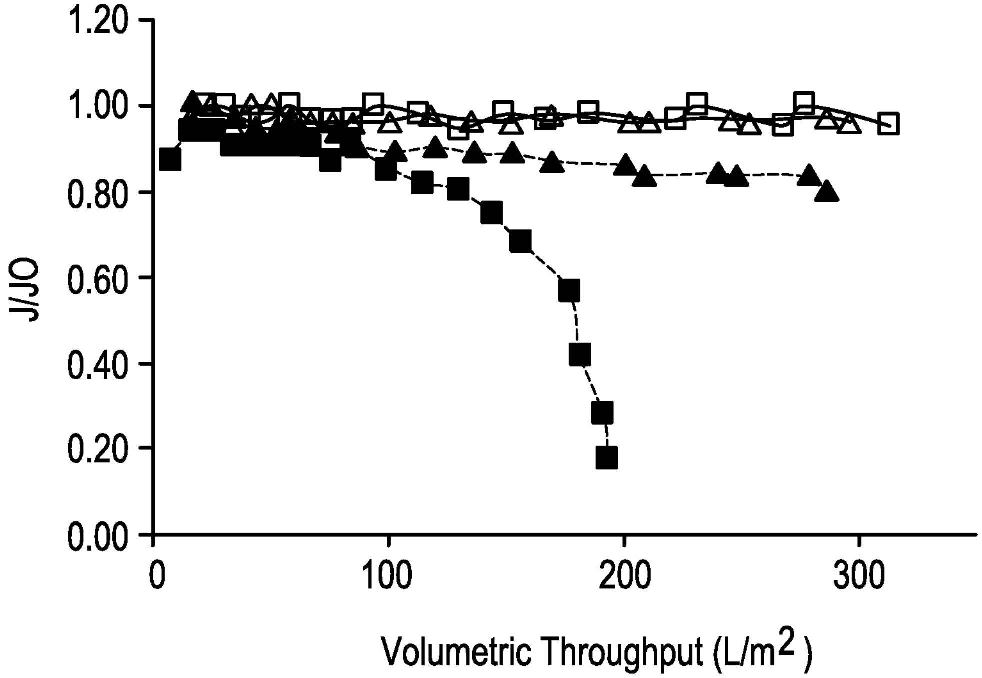

FIG. 14: BiTE® B Hydraulic Performance pH 5.9, 45 mS/cm, 1.81 g/L, VPro+Shield H, [open black square], VPro+X0SP [solid grey triangle]. Hydraulic Performance pH 4.2, 31 mS/cm, VPro+Shield H, [solid black square], VPro+X0SP [solid black triangle].

Figure 15:
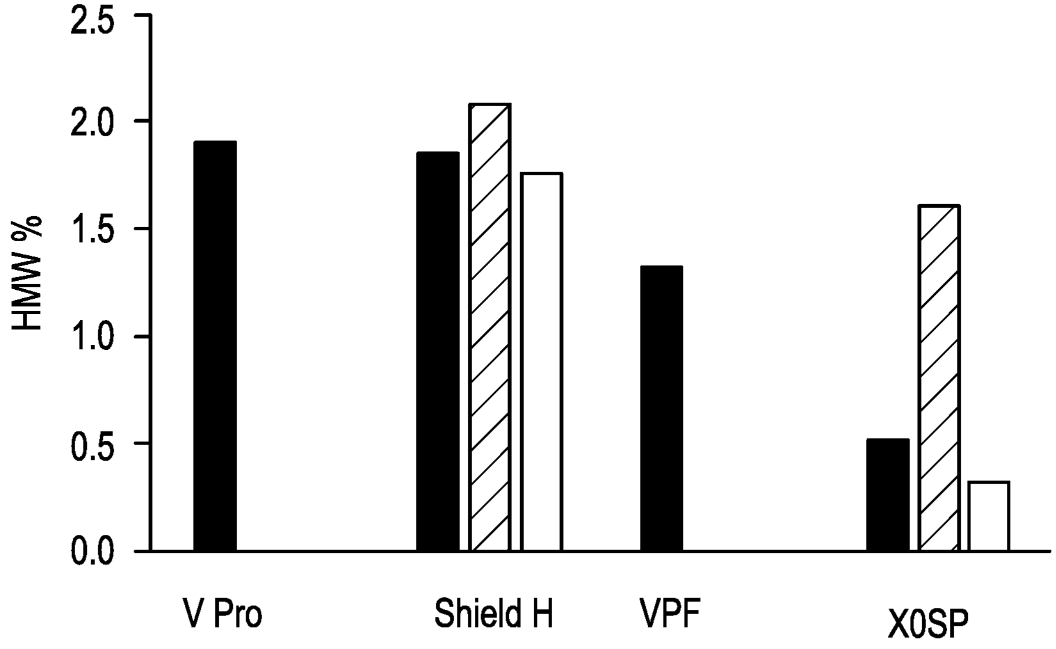

FIG. 15: BiTE® B Product Quality HMW % Setpoint pH 5.9 [black bars], low pH 4.2 [grey bars], and high conductivity-45 mS/cm [patterned bars].

DETAILED DESCRIPTION OF THE INVENTION

Described herein is a process for biologics manufacture that is advantageous in that it eliminates or combines steps required in the manufacture of Drug Substance (DS) and Drug Product (DP), enabling a fully integrated, end-to-end, continuous manufacturing process for biologics production. This process requires only one bioburden-reduction filtration step and one sterile filtration step following the UFDF operation through drug product fill/finish. Stabilizing excipients, such as Polysorbate 80 (PS80), which are typically added after a first bioburden-reducing filtration of the UFDF pool are now combined directly into the UFDF operation, thereby eliminating an entire unit operation dedicated to the excipient addition and second bioburden-reducing filtration. The filtered bulk drug product is then transferred to a filling location where it is subjected to sterile filtration and used to fill primary drug product containers, which are then sealed, labeled and packaged. Transfer of material from the drug substance manufacturing location to the drug product processing location and the subsequent drug product fills occur within the hold times and hold temperatures supported by the process operating ranges. This eliminates time-consuming freezing and thawing unit operations.

Figure 1A:
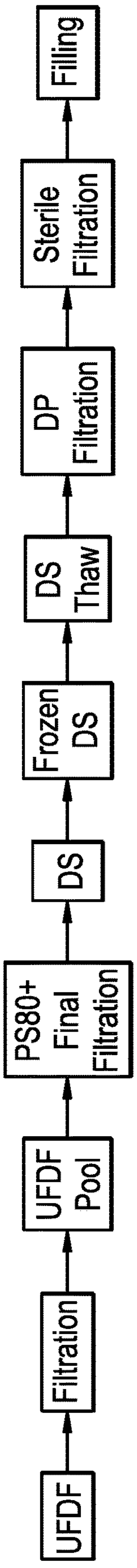
FIG. 1: (A) show the typical conventional processing steps from UFDF operation in DS process to DP filling. The conventional process can be broken down into ten steps or stages. The invention described herein reduces the number of steps or stages to five, as shown in (B).
Figure 1B:
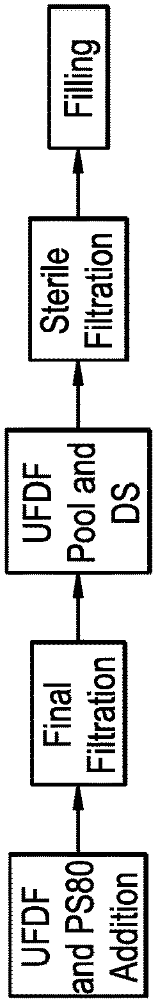

The invention reduces the number of steps or stages in a typical manufacturing process from ten to five, as shown in FIG. 1. The invention described herein also eliminates the need for pooling of drug substance from multiple freeze containers, formulation dilution, excipient addition, and similar operations following thawing of the drug substance. Also eliminated is the need for a formulation hold tank prior to sterile filtration. The invention allows for use of the same drug substance collection vessel, or direct transfer, to deliver to and/or connect to the drug product fill/finish location and for use when collecting bulk drug product samples for release assays.

The invention also allows for elimination of redundant release sampling of the formulated protein and/or drug substance and the drug product and allows for assay of attributes that are common to both to be done only once, such as at the drug product fill/finish stage, where they can be combined with other drug product attribute testing.

The invention also reduces costs associated with labor and equipment by eliminating redundant unit operations, unnecessary collection and/or storage containers, and the need for freezing and thawing and storage of frozen bulk drug substance. The invention supports modular and flexible facility design and the use of downsized equipment. Upstream and downstream unit operations can be done at smaller scale in a continuous or semi-continuous manner. The invention also enables just-in-time manufacturing, greater flexibility for manufacturing campaigns, useful in situations where the product has a low inventory demand or is subject to seasonal or other variations in demand. The invention enables minimizing the process footprint due to elimination, combining and/or connecting of various unit operations, reduction in size of equipment needed, eliminating need for physical segregation of unit operations, freeing facility design, eliminating the need for separate gowning spaces and air handlers for pre and post viral filtration manufacturing spaces. The invention provides a continuous manufacturing process that moves product from cell culture to drug substance, which can take advantage of sterile single use components. The continuous manufacturing process can be a closed process.

The invention provides an integrated, continuous method for producing a recombinant biologic therapeutic comprising providing a purified recombinant protein of interest; concentrating or diluting the purified recombinant protein by ultrafiltration; buffer exchanging the purified recombinant protein into a desired formulation by diafiltration; further diluting or concentrating the formulated recombinant protein by ultrafiltration until a target concentration is achieved; adding or combining at least one stability-enhancing excipient once the target concentration is achieved; subjecting the resulting bulk drug substance to filtration to reduce bioburden; subjecting the resulting bulk drug product to sterile filtration; and subjecting the sterile bulk drug product to a fill and finish operation; wherein neither the purified recombinant protein nor the bulk drug substance is subjected to freezing and thawing unit operations.

The invention provides a method for producing a recombinant protein drug product comprising expanding cells expressing a protein of interest to the N−1 stage; cultivating cells expressing the recombinant protein; recovering the recombinant protein through a harvest unit operation; purifying the harvested recombinant protein through at least one capture chromatography unit operation; purifying the recombinant protein through at least one polish chromatography unit operation; concentrating or diluting the purified recombinant protein by ultrafiltration; buffer exchanging the purified recombinant protein into a desired formulation by diafiltration; further concentrating or diluting the formulated purified recombinant protein by ultrafiltration until a target concentration is achieved, then adding one or more stability-enhancing excipients; subjecting the formulated drug substance to a single unit operation to reduce bioburden resulting in filtered bulk drug product; sterile filtering the bulk drug product; filling a primary drug product container with sterile bulk drug product; and sealing, labeling and packaging the primary drug product container; wherein neither the recombinant protein nor the drug substance is subjected to freezing and thawing unit operations.

As used herein "drug substance" refers to a purified recombinant protein that is intended to furnish pharmacological activity or other direct effect in the diagnosis, cure, mitigation, treatment, or prevention of disease or to affect the structure or any function of any part of the human body. Typically, the drug substance comprises the formulated protein from the UFDF unit operation with the addition of one or more stability-enhancing excipients. "Purified recombinant protein" or "purified protein" are used interchangeable and refer to a recombinant protein that is purified away from undesirable proteins, polypeptides, impurities and/or other contaminants that would interfere with its therapeutic, diagnostic, prophylactic or other use.

As used herein, "drug product" refers to the finished dosage form that may contain one or more drug substances, in association with one or more pharmaceutically or physiologically acceptable carriers, diluents and/or excipients. "Bulk drug product" or filtered bulk drug product are used interchangeably and are used to refer to the drug substance following bioburden-reducing filtration.

In one embodiment, the invention provides drug substances and drug products made by the methods described herein.

A purified recombinant protein is typically subjected to a UFDF unit operation prior to conversion to drug substance. The ultrafiltration is typically split into two parts, an initial ultrafiltration step where the recombinant protein is partially concentrated or diluted, followed by formulating the recombinant protein with one or more pharmaceutically or physiologically acceptable carriers, diluents and/or excipients through buffer exchange using diafiltration, and a second ultrafiltration step that takes the formulated recombinant protein to a target concentration desired for the final drug product.

For modalities where the recombinant protein typically needs to be concentrated to achieve a desired target concentration desired for the final drug product, such as for monoclonal antibodies, the degree of concentration in the initial ultrafiltration step depends on the desired target value for the drug product. Typically, the initial ultrafiltration step brings the concentration to about half of the desired final target value. The degree of concentration during this first step can be greater or less depending the situation, the desired final target dose, the nature of the recombinant protein, and/or other factors. For the second ultrafiltration step, the target concentration may be anywhere from 20 mg/ml to 40 mg/ml or higher than the desired final concentration of the drug product to account for any holdup in the second ultrafiltration system; for example, the higher the holdup volume, the higher the concentration is set, and the lower the holdup volume, the lower, or closer to the desired drug product concentration, it is set.

For highly potent modalities, such as bispecific T cell engagers, where the recombinant protein concentration may be higher than the desired final concentration for the drug product, the recombinant protein may be diluted to the desired final concentration during the UFDF unit operation.

UFDF filters are well known and common in the art and are commercially available from many sources. There are many types of materials available, regenerated cellulose Pellicon (MilliporeSigma, Danvers, Mass.), stabilized cellulose, Sartocon® Slice, Sartocon® ECO Hydrosart® (Sartorius, Goettingen, Germany), polyethersulfone (PES) membrane, Omega (Pall Corporation, Port Washington, N.Y.). Depending on the scale of purification, typical filter sizes range from below 0.11 $m^2$ area to 1.14 $m^2$ area and above. Multiple filters can be used to the capacity that holders, skids, or the physical set up of the UFDF system will allow or are needed to achieve the desired objectives of a production process. For example, in clinical production situations, filter combinations that range to 11.4 $m^2$ area or greater and for commercial production scale, the range can go to >40 $m^2$ area.

Bispecific T cell engagers, BiTE®s, are highly potent and susceptible to aggregation during the purification process. BiTE®s are susceptible to aggregation which can impact concentration during the UFDF operation. It was found that loading regenerated cellulose membranes with an half-life extended BiTE® at concentrations as high as 170 g/$m^2$ of membrane area with thirteen diavolumes was still within the product profile. In addition, rinsing stabilized cellulose-based membranes with buffer after each cycle loading of up to 71.4 g/$m^2$ of an HLE BiTE® was sufficient for cleaning and did not impact future membrane performance, irrespective of higher loading and high initial concentration, for at least three cycles. This allowed for optimum recycling of TFF filters with buffer rinsing between cycles without the use of caustic chemical cleaning solutions (sodium hydroxide) and allowed for quicker processing.

For bispecific T cell engagers, the stabilized cellulose-based membranes may be loaded to an initial target overconcentration that is 2.5× the target concentration. In one embodiment, the target overconcentration is 1.1× to 2.5×. In one embodiment, the target overconcentration is 1.1× to 1.5×. In one embodiment, the target over concentration is 1.5× to 2.5×.

Buffer exchange by diafiltratration into a desired formulation buffer is typically performed prior to the second ultrafiltration step. The buffer comprising the purified recombinant protein from the first ultrafiltration concentration is exchanged for one that comprises one or more pharmaceutically or physiologically acceptable carriers, diluents and/or excipients that is desired for the drug product formulation and will act to achieve certain desired results in the final drug product, such as maintaining product quality, stability, and/or integrity during subsequent steps, including, but not limited to, filtration, filling, lyophilization, freezing, packaging, storage, transportation, delivery, thawing, and/or administration. The buffer may also be used to adjust attributes such as osmolality, conductivity and/or protein concentration of the final drug product. The components of the formulation may provide protection for the drug product and may be desired to enhance and/or diminish particular attributes of the drug product, such as protecting against degradation pathways; facilitating aqueous solubility; reducing toxicity and/or reactivity; providing for rapid clearance; reducing immunogenicity; acting as cryoprotectants or lyoprotectants; stabilizing native conformations to maintain efficacy, potency, safety; protecting against chemical and physical degradation; protein stabilization to reduce surface tension, protein-surface and protein-protein interactions; reducing hydrophobic interactions; optimizing conditions such as pH, ionic strength; and buffering, and stabilizing. Excipients are usually prepared in the form of one or more buffer solutions.

Pharmaceutically or physiologically acceptable carriers, diluents and/or excipients can include, but are not limited to, one or more of the following: sterile diluents such as water for injection; saline solutions such as neutral buffered saline, phosphate buffered saline, physiological saline, Ringer's solution, isotonic sodium chloride; fixed oils such as synthetic mono- or diglycerides which may serve as the solvent or suspending medium; polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid or glutathione; carbohydrates such as glucose, mannose, sucrose or dextrans, mannitol; proteins; nonionic surfactants; detergents; emulsifiers; polypeptides or amino acids such as glycine; buffers such as acetates, citrates or phosphates, agents for the adjustment of tonicity such as sodium chloride or dextrose; adjuvants (e.g., aluminum hydroxide); and preservatives. Excipients that are concentration or filtration sensitive or for any other reason may require special handling or consideration, may be added during the second ultrafiltration step or following the UFDF unit operation.

Typically, following the UFDF unit operation, the UFDF pool is filtered to reduce bioburden and then collected into an external hold tank where a unit operation for the addition of stability-enhancing excipients to the UFDF pool followed by another filtration to reduce the bioburden of the formulated drug substance is performed.

As described herein, the invention eliminates the need for the separate unit operation to add stability-enhancing excipients, such as polysorbate 80, to an external hold tank containing bioburden-reduced UFDF pools and filtering again. The invention provides adding or combining such stability-enhancing excipients directly into the UFDF retentate tank. When adding the excipient to the UFDF retenant tank it does not need to pass through the UFDF filters. Access to the filters can be closed such that the excipient does not interact with the UFDF filters. In one embodiment, one or more stability-enhancing excipients are added to or combined with the formulated recombinant protein. In one embodiment, one or more stability-enhancing excipients are added in-line to the formulated recombinant protein. In a related embodiment, one or more stability-enhancing excipients are added directly to the ultrafiltration and diafiltration (UFDF) retentate tank. In one embodiment, one or more excipients are added to or combined with the formulated recombinant protein once a target concentration is achieved. In one embodiment, one or more excipients are added to in-line to the formulated recombinant protein once a target concentration is achieved. The excipient(s) may also be added in-line with the UFDF pool flowing directly into a hold vessel. In one embodiment, the stability-enhancing excipient and the UFDF pool are added separately to a storage vessel.

Stability-enhancing excipients include, but are not limited to, nonionic surfactants, detergents, and/or emulsifiers. Nonionic surfactants include, but are not limited to, poly-oxy-ethylene (PEO) based surfactants, block copolymers of polyethylene oxide-polypropylene oxide; polyoxyethylene (20) sorbitan monooleate; polysorbates 20 and 80, Tween® 20 and Tween® 80; polyethylene glycol (PEG), Pluronics; poloxamers, such as Poloxamer 188, Poloxamer 407.

In one embodiment the stability-enhancing excipient is a non-ionic detergent or surfactant. In one embodiment, the stability-enhancing excipient is a poly-oxy-ethylene (PEO) based surfactant. In one embodiment, the stability-enhancing excipient is selected from polysorbate 80 or polysorbate 20.

The amount of stability-enhancing excipient depends on the desired final formulation of the drug product. For example, a typical range for polysorbate 80 is 0.001 to 0.1% (weight/volume). In one embodiment the concentration of polysorbate 80 is 0.01% (weight/volume) in the drug substance formulation buffer. For excipients such as polysorbate 80, where the solution may be viscous, dilution to 0.01% in the formulation buffer lowers the viscosity and simplifies flushing the line and the bioburden-reducing filter.

In one embodiment of the invention, one or more additional formulated recombinant proteins and/or drug substances may be added prior to bioburden-reduction filtration and/or sterile filtration, to ultimately form a combination drug product.

Following the UFDF unit operation and the addition of any stability-enhancing excipients, the drug substance is filtered to reduce bioburden and the pool collected into a hold vessel, such as a sterilized, single use storage bag. Prior to adding the drug substance to the bioburden reducing filter, the line connecting the UFDF unit to the bioburden reducing unit may be flushed with the formulation buffer containing the stabilizing excipient at the target concentration followed by saturating the bioburden reducing filter with the same buffer. This helps in achieving an accurate concentration of stabilizing-excipient in the formulated recombinant protein. As used herein, bioburden reduction refers freeing the drug substance of microorganisms that are not desired in the final drug product. Suitable filters are known and widely used for bioburden reduction such as SHC and PVDF filters and general 0.2-micron filters and are commercially available from many sources.

In a typical biologics manufacturing process, the drug substance would be frozen for storage or ease of transportation to a drug processing facility. The invention eliminates the freezing and thawing unit operations, the drug substance conversion to drug product is immediate and continuous. This is useful for a continuous, integrated, end-to-end therapeutic biologics manufacturing platform, platforms that are automated, platforms that operate with minimal or no operator intervention, just-in-time manufacturing platforms, production platforms where drug product demand is variable or limited, or where it is not desired or possible to maintain an inventory of frozen drug substance. It also reduces amount and timing of attribute testing since attributes common between the drug substance and the drug product could be performed only once at the drug product fill/finish phase. Also eliminated is any additional processing of the drug substance following freeze/thaw that are needed to convert to the bulk drug product.

Following the UFDF unit operation, one or more additional unit operations may be performed, such as virus filtration. Multispecific modalities, due in part to their highly specific design and function, can achieve desired therapeutic potency at low concentrations, unlike monoclonal antibodies that require much higher concentrations to achieve desired potency. In particular, some bispecific antibodies, such as bispecific T cell engagers, achieve desired potency at very low concentrations and therefore can have a drug substance formulation concentration of <10 g/L while for most therapeutic monoclonal antibodies, the drug substance formulation concentration is much higher, 70 g/L or more. At such high concentrations, formulated antibody solutions can quickly plug a viral filter.

Because viral filter pore size is so small, high concentration formulations, such as those comprising monoclonal antibodies, foul the filter at a much lower volume. For high concentration antibody formulations, >10 g/L, the filter or membrane area needed to process such solutions would make it impractical for manufacturing use. In a typical order of operations for monoclonal antibody processing, viral filtration typically follows a polishing step, at a point in the manufacturing process where the antibody pool is at the most dilute state. The subsequent UFDF operation concentrates the antibody formulation. For potency high potency bispecific T cell engagers, which are at a low concentration both prior to and following UFDF, it was found that the filter or membrane area needed to process the formulated bispecific T cell engager was reasonable for viral filtration regardless of the order of the viral filter and UFDF operations, and viral filtration of formulated BiTE®s, was possible, as described herein.

The invention also provides a method for reducing viral contaminants in a composition comprising a recombinant bispecific T cell engager comprising providing a sample comprising less than 7.0 g/L of a recombinant bispecific T cell engager at a pH less than or equal to 6.0, having a conductivity of 23-45 mS/cm; subjecting the sample to a virus filtration unit operation comprising a viral filter alone or in combination with a depth filter or surface modified membrane prefilter; and collecting the viral filter eluate comprising the recombinant bispecific T cell engager, in a pool or as a stream.

The also invention provides a method for decreasing high molecular weight species during manufacture of a recombinant bispecific T cell engager comprising providing a sample comprising less than 7 g/L recombinant bispecific T cell engager, at a pH less than or equal to 6.0, having a conductivity of 23-45 mS/cm; subjecting the sample to a virus filtration unit operation comprising a viral filter in combination with a depth filter; and collecting the viral filter eluate in a pool or as a stream; wherein the percentage of high molecular weight species in the filter eluate pool is decreased compared to use of a virus filtration unit operation comprising a viral filter alone or in combination with a surface modified membrane prefilter.

The invention also provides a method for producing a purified, formulated recombinant bispecific T cell engager, the method comprising purifying a harvested recombinant bispecific T cell engager through one or more chromatography unit operations; subjecting the purified recombinant bispecific T cell engager to an ultrafiltration and diafiltration unit operation resulting in a formulated bispecific T cell engager at a concentration of ≤5 g/L and subjecting the formulated bispecific T cell engager to a viral filtration unit operation; obtaining a purified, formulated recombinant bispecific T cell engager.

As described herein, low concentration drug substance formulations comprising bispecific T cell engager drug substances were successfully processed through a viral filtration operation. Formulated bispecific T cell engagers having a concentration of <10 g/L, preferably ≤5 g/L are within in the invention. Preferably formulated bispecific T cell engagers having a concentration of ≤0.10 g/L, ≤0.5 g/L, ≤1 g/L, ≤2 g/L, ≤3 g/L, ≤4 g/L. In one embodiment, the concentration ≤3.5 g/L. In one embodiment the concentration is ≤1.79 g/L. In one embodiment the concentration is 1.59 g/L-3.16 g/L. In one embodiment, the concentration of the formulated bispecific T cell engager is 1.59 g/L-1.79 g/L. In one embodiment, the concentration of the formulated bispecific T cell engager is 1.79 g/L-3.16 g/L. In one embodiment, the concentration of the formulated bispecific T cell engager is 1.59 g/L. In one embodiment, the concentration of the formulated bispecific T cell engager is 1.79 g/L. In one embodiment, the concentration of the formulated bispecific T cell engager is 3.2 g/L.

In one embodiment, the invention provides subjecting formulated multispecific proteins, formulated multispecific proteins including stability enhancing agents, bulk drug substance comprising a multispecific protein, and/or the bulk drug product comprising a multispecific protein to virus filtration. In one embodiment, the multispecific protein in a bispecific antibody. The virus filtration step can be followed by a bioburden reduction and/or sterile filtration. Stability enhancing agents may be added to the virus filtration pool. Optionally, the viral filtration pool may be stored short term at 2-8° C. or long term at −70° C.

The unit operations could be continuously or semi-continuously connected through the viral filtration step, bioburden reduction filtration or sterile filtration step, or through the fill/finish operation. The viral filtration and post-viral filtration steps may take place in the same space as the pre-viral filtration steps.

Non-enveloped viruses are difficult to inactivate without risk to the protein therapeutic being manufactured, however such viruses can be removed by size-based filtration methods, removing virus particles using filters with small pore sizes. Viral filtration can be performed using micro- or nano-filters, such as those available from Plavona® (Asahi Kasei, Chicago, Ill.), Virosart® (Sartorius, Goettingen, Germany), Viresolve® Pro (MilliporeSigma, Burlington, Mass.), Pegasus™ Prime (Pall Biotech, Port Washington, N.Y.), CUNO Zeta Plus VR, (3M, St. Paul, Mn) and may occur at one or more steps in the downstream operations of a biomanufacturing process. Typically, viral filtration precedes the UFDF operation, but may also take place following UFDF.

Bispecific T cell engagers, such as HLE BiTE®s, are highly potent and susceptible to aggregation during the purification process. Bispecific T cell engagers can be sensitive to purification conditions and susceptible to aggregation which can result in reduced throughput and increasing flux decay during virus filtration operations. Pre-filters can be used in combination with viral filters to help eliminate certain contaminants in the product pool or eluate stream before applying the pool or eluate to the viral filter, maintaining continuity flow during the virus filtration operation and extending the life of the filter. Pre-filters are commercially available and include surface modified polyethersulfone membrane filters such as Viresolve® Pro Shield, Viresolve® Pro Shield H) and depth filters such as Viresolve® Prefilter and Millistak+® HC Pro X0SP, all from MilliporeSigma (Burlington, Mass.). As described herein, depth filter pre-filters were found to be particularly effective in virus filtration operations for bispecific T cell engagers.

There is not much information related to downstream processing of bispecific antibodies, so platforms developed for monoclonal antibodies are often applied (Shulka and Norman, Chapter 26 Downstream Processing of Fc Fusion Proteins, Bispecific Antibodies, and Antibody-Drug Conjugates, in Process Scale Purification of Antibodies Second Edition, Uwe Gottswchalk editor, p 559-594, John Wiley & Sons, 2017). However, these processes don't necessarily perform in the same way for bispecific proteins, such as recombinant bispecific T cell engagers, as they do for monoclonal antibodies. As described herein, the mere addition of a pre-filter to a viral filter did not uniformly improve performance when processing recombinant half-life extended bispecific T cell engager proteins, particularly half-life extended bispecific T cell engagers. It was found that by limiting the concentration of the half-life extended bispecific T cell engager protein to less than 7.0 g/L, at a pH less than or equal to 6.0, having a conductivity of 23-45 mS/cm, that subjecting the protein to a virus filtration unit operation comprising a viral filter alone or in combination with a depth filter prefilter or surface modified membrane prefilter improved performance. In particular, the use of a depth filter prefilter in combination with a viral filter reduced flux decay and/or decreased % HMW in comparison to the use of a viral filter alone or in combination with a surface modified membrane prefilter.

The invention also provides a method for decreasing flux decay and reducing high molecular weight species in a virus filtration unit operation during manufacture of a recombinant bispecific T cell engager comprising providing a sample comprising less than or equal to 1.75 g/L of a recombinant bispecific T cell engager at a pH of 4.2-6.0, the conductivity is 23-45 mS/cm; subjecting the purified recombinant bispecific T cell engager to a virus filtration unit operation comprising a viral filter in combination with a depth filter; and collecting the filter eluate in a pool or as a stream; wherein the percentage of high molecular weight species in the filter eluate pool or stream is decreased compared to a virus filtration unit operation comprising a viral filter alone or in combination with a surface modified membrane prefilter.

In one embodiment the pH of the pool or stream is 4.0 to 6.0. In one embodiment the pH of the pool or stream is 4.2 to 6.0. In a related embodiment the pH of the pool or stream is 4.2 to 5.9. In a related embodiment the pH of the pool or stream is 4.2 to 5.0. In one embodiment the pH of the pool or stream is 5.0 to 6.0. In one embodiment he pH of the pool or stream is 5.0 to 5.9. In a one embodiment the conductivity of the pool or stream is 23 to 45. In one embodiment the conductivity of the pool or stream is 23 to 32. In one the conductivity of the pool or stream is 23 to 28. In one embodiment the concentration of the half-life extended bispecific T cell engager is 1.75 to 7.0 g/L. In one embodiment the concentration of the half-life extended bispecific T cell engager is 7.0 g/L. In one embodiment the concentration of the half-life extended bispecific T cell engager is 1.75 g/L. In a related embodiment the concentration of the half-life extended bispecific T cell engager is 1.75 to 1.18 g/L.

In one embodiment the pH is 5.0, the concentration of the concentration of the half-life extended bispecific T cell engager is 1.75 g/L. In a related embodiment the pH is 6.0, the concentration of the half-life extended bispecific T cell engager is 7.0 g/L and the conductivity is 28 mS/cm. In one embodiment the pH is 5.9, the concentration of the half-life extended bispecific T cell engager is 1.81 g/L and the conductivity is 31.36 to 45 mS/cm. In one embodiment the pH is 4.2 to 5.9, the concentration of the half-life extended bispecific T cell engager is 1.75 to 1.81 g/L, and the conductivity is 23 to 45 mS/cm. In one embodiment the pH is 4.2 to 5.0, the concentration of the concentration of the half-life extended bispecific T cell engager is 1.75 g/L, and the conductivity is 23 mS/cm. In one embodiment the pH is 5.9, the concentration of the concentration of the half-life extended bispecific T cell engager is 1.81 g/L, and the conductivity is 31.36 to 45 mS/cm. In one embodiment the purified recombinant half-life extended bispecific T cell engager is less than or equal to 7.0 g/L, with a pH less than or equal to 6.0, having a conductivity of 23 to 45 mS/cm In one embodiment the virus filtration unit operation comprises a viral filter in combination with a depth filter pre-filter. In a related embodiment the depth filter pre-filter is an absorptive depth filter or a synthetic depth filter. In one embodiment the virus filtration unit operation comprises a viral filter in combination with a surface modified membrane pre-filter. In a related embodiment the virus filtration unit operation comprises a viral filter in combination with a surface modified polyethersulfone membrane prefilter. In one embodiment the virus filtration unit operation comprises only a viral filter.

The filtered bulk drug product is also subjected to a bioburden reduction filtration and/or sterile filtration to ensure it is free of viable microorganisms and then introduced to an aseptic processing facility where it is used to fill primary drug product containers, which are then sealed, labeled and packaged.

An aseptic processing facility is a facility maintained with minimized sources of contaminants that could impact the sterility of the drug product. Such a facility can be a dedicated clean room having one or more filling stations for drug product fill/finish, each filling station comprising one or more automatic fill machines with multiple needles to fill multiple drug product containers at one time. An aseptic processing facility may also be a self-contained gloveless, sterile isolator station. Such a station may be located in an open ball-room manufacturing facility, in particular, such a station may be located at or near a drug substance preparation area. Such modular gloveless, sterile, isolators for liquid and lyophilized drug products include, but are not limited to, Vanrx (Barnaby, British Columbia, Canada). Such systems allow for development of continuous systems that do not require operator intervention. Small scale, modular workstations with robotics for performing the material handling, filling and closing activities within a completely closed isolator allow for reduction in size of manufacturing plants and greater flexibility for modular and reconfigurable use of the space may also be used, but may require some operator intervention. The present invention allows for leveraging existing single-use assemblies for creating a new flow paths that are fully robotic, with aseptic filling inside of a gloveless insolator, having a smaller footprint than traditional built in place facilities with low capital expense.

The invention provides a method for reducing the manufacturing footprint for drug product production process comprising subjecting a purified recombinant protein of interest to a UFDF unit operation until a target concentration has been achieved; adding at least one stability-enhancing excipient directly to the UFDF retentant tank; subjecting the bulk drug substance to a single unit operation to reduce bioburden followed by sterile filtration; subjecting the bulk drug product to a fill and finish unit operation; wherein neither the recombinant protein nor the drug substance is subjected to freezing and thawing unit operations. A virus filtration unit operation may precede or follow a UFDF operation.

In one embodiment of the invention the bulk drug product is delivered to an aseptic processing facility where it is sterile filtered prior to fill/finish. In one embodiment the aseptic processing facility comprises at least one filling station. In one embodiment, the filtered bulk drug product is in a storage vessel that can be delivered to the aseptic processing facility. In another embodiment, the storage vessel can be connected directly to the aseptic processing facility. In one embodiment the drug product is filtered into a storage bag that is directly delivered and/or connected to the aseptic processing facility. In one embodiment the bulk drug product can be delivered directly from bioburden reduction filtration to the aseptic processing facility via tubing or other connections.

In one embodiment the bulk drug product is delivered to the aseptic processing facility, which may be a robotic unit, such as, for example, a gloveless, sterile isolator. In one embodiment, the robotic unit has a connection with a storage vessel or filter containing or processing the bulk drug product. The ability to interconnect drug substance processing directly with drug product processing, particularly by connecting directly to a robotic filler, offers the opportunity to reduce the process footprint. By compressing the process, removing redundant or unnecessary equipment or process steps, elimination of drug substance freeze/thaw, allows for design and implementation of a process having a footprint of 3,000 square feet or less.

In one embodiment of the invention a primary drug product container is filled with sterile bulk drug product. In another embodiment the primary drug product container is sealed, labeled and packaged. In one embodiment the primary drug product container is a vial, ampoule, cartridge, syringe or syringe-containing device, or other suitable storage or delivery device, apparatus, or system.

The invention provides a method for reducing drug substance loss and/or destabilization during recombinant therapeutic protein manufacturing comprising subjecting a purified recombinant protein of interest to a UFDF unit operation; adding at least one stability-enhancing excipient to the UFDF retenate tank once a target concentration has been achieved; subjecting the UFDF pool to a single filtration to reduce bioburden resulting in bulk drug substance; wherein neither the recombinant protein nor the drug substance is subjected to freezing and thawing unit operations. A virus filtration unit operation may precede or follow a UFDF operation.

Proteins that make up the drug substance are a result of a delicate balance between various interactions including covalent linkages, hydrophobic interactions, electrostatic interactions, hydrogen bonding, van der Waals forces that shape and maintain their folded, three-dimensional structure. The folded state of a protein is only marginally more stable than unfolded state and changes in protein's environment may trigger degradation or inactivation, which directly impact product quality.

The present invention reduces the number of bioburden-elimination filtration steps, which is beneficial for reducing product loss due to volume hold-up during filtration as well as avoiding any impact on product quality and protein structure due to shear-induced PQ changes that may result from multiple filtrations. It is also beneficial in that it streamlines the manufacturing process, making it more compatible with continuous manufacturing platforms; reduces the footprint of a drug substance manufacturing facility, and potentially reduces manufacturing timelines making it quicker to get to packaged drug product. There is also a cost savings and waste reduction compared with a typical biologics manufacturing platform where three or more bioburden reducing filters and associated hold tanks or collection vessels, may be used from the UFDF unit operation to drug product fill/finish.

The methods of the invention eliminate freezing, frozen storage, thawing, mixing and pooling of thawed drug substance, the "freezing and thawing unit operations". The freezing and thawing of bulk drug substance during manufacture can be detrimental to protein stability and affect product quality. Ice-liquid interface, cryoconcentration (concentration of proteins as the liquid freezes can result in changes in protein structure), excipient crystallization, ph shifts (due to selective precipitation of buffer components, destabilization of proteins), increased protein concentration may result in aggregation or precipitation, cold denaturation (spontaneous unfolding at cold temps), container surface interactions, leachables and extractables from the container. (Rathore and Rajan, Biotechnol. Prog. 24: 504-514, 2008).

The terms "polynucleotide" or "nucleic acid molecule" are used interchangeably throughout and include both single-stranded and double-stranded nucleic acids and includes genomic DNA, RNA, mRNA, cDNA, or synthetic origin or some combination thereof which is not associated with sequences normally found in nature. The terms "isolated polynucleotide" or "isolated nucleic acid molecule" specifically refer to sequences of synthetic origin or those not normally found in nature. Isolated nucleic acid molecules comprising specified sequences may include, in addition to the sequences expressing the protein of interest, coding sequences for up to ten or even up to twenty other proteins or portions thereof or may include operably linked regulatory sequences that control expression of the coding region of the recited nucleic acid sequences, and/or may include vector sequences. The nucleotides comprising the nucleic acid molecules can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

As used herein, the term "isolated" means (i) free of at least some other proteins or polynucleotides with which it would normally be found, (ii) is essentially free of other proteins or polynucleotides from the same source, e.g., from the same species, (iii) separated from at least about 50 percent of polypeptides, polynucleotides, lipids, carbohydrates, or other materials with which it is associated in nature, (iv) operably associated (by covalent or noncovalent interaction) with a polypeptide or polynucleotide with which it is not associated in nature, or (v) does not occur in nature.

The terms "polypeptide" or "protein" are used interchangeably throughout and refer to a molecule comprising two or more amino acid residues joined to each other by peptide bonds. Polypeptides and proteins also include macromolecules having one or more deletions from, insertions to, and/or substitutions of the amino acid residues of the native sequence, that is, a polypeptide or protein produced by a naturally-occurring and non-recombinant cell; or is produced by a genetically-engineered or recombinant cell, and comprise molecules having one or more deletions from, insertions to, and/or substitutions of the amino acid residues of the amino acid sequence of the native protein. Polypeptides and proteins also include amino acid polymers in which one or more amino acids are chemical analogs of a corresponding naturally-occurring amino acid and polymers. Polypeptides and proteins are also inclusive of modifications including, but not limited to, glycosylation, lipid attachment, sulfation, gamma-carboxylation of glutamic acid residues, hydroxylation and ADP-ribosylation. The terms "isolated protein", "isolated recombinant protein", or "purified recombinant protein" may be used interchangeably and refer to a polypeptide or protein of interest, that is purified away from proteins or polypeptides or other contaminants that would interfere with its therapeutic, diagnostic, prophylactic, research or other use. In particular, drug substances and drug products made from recombinant proteins of interest processed using the invention as described herein may be referred to as "recombinant protein drug products", "recombinant biologic therapeutics".

Polypeptides and proteins can be of scientific or commercial interest, including protein therapeutics. Proteins of interest include, among other things, secreted proteins, non-secreted proteins, intracellular proteins or membrane-bound proteins. Proteins of interest can be produced by recombinant animal cell lines using methods described herein and may be referred to as "recombinant proteins" or "recombinant protein therapeutics". The expressed protein(s) may be produced intracellularly or secreted into the culture medium from which it can be recovered and/or collected. Proteins of interest may include proteins that exert a therapeutic effect, for example, by binding a target, particularly a target among those listed below, including targets derived therefrom, targets related thereto, and modifications thereof.

Proteins of interest may include "antigen-binding proteins". Antigen-binding protein refers to proteins or polypeptides that comprise an antigen-binding region or antigen-binding portion that has a strong affinity for another molecule to which it binds (antigen). Antigen-binding proteins encompass antibodies, peptibodies, antibody fragments, antibody derivatives, antibody analogs, fusion proteins (including single-chain variable fragments (scFvs) and double-chain (divalent) scFvs, DARPins®, muteins, multispecific proteins, bispecific proteins, xMAbs, and chimeric antigen receptors (CARs or CAR-Ts) and T cell receptors (TCRs).

"Multispecific", "multispecific protein", and "multispecific antibody" are used herein to refer to proteins that are recombinantly engineered to simultaneously bind and neutralize at least two different antigens or at least two different epitopes on the same antigen. For example, multispecific proteins may be engineered to target immune effectors in combination with targeting cytotoxic agents to tumors or infectious agents. These multispecific proteins have been found useful for a variety of applications, such as in cancer immunotherapy, by redirecting immune effector cells to tumor cells, modifying cell signaling by blocking signaling pathways, targeting tumor angiogenesis, blocking cytokines, and as pre-targeted delivery vehicles for drugs, such as delivery of chemotherapeutic agents, radiolabels (to improve detection sensitivity) and nanoparticles (directed to specific cells/tissues, such as cancer cells).

The most common and most diverse group of multispecific proteins are those that bind two antigens, referred to herein as "bispecific", "bispecific proteins", and "bispecific antibodies". Bispecific proteins can be grouped in two broad categories: immunoglobulin G (IgG)-like molecules and non-IgG-like molecules. IgG-like molecules retain Fc-mediated effector functions, such as antibody-dependent cell mediated cytotoxicity (ADCC), complement-dependent cytotoxicity (CDC), and antibody-dependent cellular phagocytosis (ADCP), the Fc region helps improve solubility and stability and facilitate some purification operations. Non-IgG-like molecules are smaller, enhancing tissue penetration (see Sedykh et al., Drug Design, Development and Therapy 18(12), 195-208, 2018; Fan et al., J Hematol & Oncology 8:130-143, 2015; Spiess et al., Mol Immunol 67, 95-106, 2015; Williams et al., Chapter 41 Process Design for Bispecific Antibodies in Biopharmaceutical Processing Development, Design and Implementation of Manufacturing Processes, Jagschies et al., eds., 2018, pages 837-855. Bispecific proteins are sometimes used as a framework for additional components having binding specificities to different antigens or numbers of epitopes, increasing the binding specificity of the molecule.

The formats for bispecific proteins, which include bispecific antibodies, are constantly evolving and include, but are not limited to, quadromas, knobs-in-holes, cross-Mabs, dual variable domains IgG (DVD-IgG), IgG-single chain Fv (scFv), scFv-CH3 KIH, dual action Fab (DAF), half-molecule exchange, κλ-bodies, tandem scFv, scFv-Fc, diabodies, single chain diabodies (scDiabodies), scDiabodies-CH3, triple body, miniantibody, minibody, TriBi minibody, tandem diabodies, scDiabody-HAS, Tandem scFv-toxin, dual-affinity retargeting molecules (DARTs), nanobody, nanobody-HSA, dock and lock (DNL), strand exchange engineered domain SEEDbody, Triomab, leucine zipper (LUZ-Y), XmAb®; Fab-arm exchange, DutaMab, DT-IgG, charged pair, Fcab, orthogonal Fab, IgG(H)-scFv, scFV-(H) IgG, IgG(L)-scFV, IgG(L1H1)-Fv, IgG(H)-V, V(H)—IgG, IgG(L)-V V(L)-IgG, KIH IgG-scFab, 2scFV-IgG, IgG-2scFv, scFv4-Ig, Zybody, DVI-Ig4 (four-in-one), Fab-scFv, scFv-CH-CL-scFV, F(ab')2-scFv2, scFv-KIH, Fab-scFv-Fc, tetravalent HCAb, scDiabody-Fc, diabody-Fc, intrabody, ImmTAC, HSABody, IgG-IgG, Cov-X-Body, scFv1-PEG-scFv2, bi-specific T cell engagers (BiTEso) and half-life extended bispecific T cell engagers (HLE BiTEs) (Fan supra; Spiess supra; Sedykh supra; Seimetz et al., Cancer Treat Rev 36(6) 458-67, 2010; Shulka and Norman, Chapter 26 Downstream Processing of Fc Fusion Proteins, Bispecific Antibodies, and Antibody-Drug Conjugates, in Process Scale Purification of Antibodies Second Edition, Uwe Gottswchalk editor, p 559-594, John Wiley & Sons, 2017; Moore et al., MAbs 3:6, 546-557, 2011).

In some embodiments are included bispecific T cell engagers (BiTE®) antibody constructs, recombinant protein constructs made from two flexibly linked antibody derived binding domains (see WO 99/54440 and WO 2005/040220). One binding domain of the construct is specific for a selected tumor-associated surface antigen on target cells, such as EGFRvIII, MSLN, CDH19, DLL3, CD19, CD33, CD38, FLT3, CDH3, BCMA, PSMA, MUC17, CLDN18.2, or CD70; the second binding domain is specific for CD3, a subunit of the T cell receptor complex on T cells. The BiTE® constructs may also include the ability to bind to a context independent epitope at the N-terminus of the CD3s chain (WO 2008/119567) to more specifically activate T cells. Half-life extended BiTE® constructs are BiTE® antibody constructs that include fusion of the small bispecific antibody construct to larger proteins, which preferably do not interfere with the therapeutic effect of the BiTE® antibody construct. Examples include bispecific T cell engagers comprising bispecific Fc-molecules e.g. described in US 2014/0302037, US 2014/0308285, WO 2014/151910 and WO 2015/048272. An alternative strategy is the use of human serum albumin (HAS) fused to the bispecific molecule or the mere fusion of human albumin binding peptides (see e.g. WO 2013/128027, WO2014/140358). Another HLE BiTE® strategy comprises fusing a first domain binding to a target cell surface antigen, a second domain binding to an extracellular epitope of the human and/or the Macaca CD3e chain and a third domain, which is the specific Fc modality (WO 2017/134140).

In some embodiments, bispecific proteins may include blinatumomab, catumaxomab, ertumaxomab, solitomab, targomiRs, lutikizumab (ABT981), vanucizumab (RG7221), remtolumab (ABT122), ozoralixumab (ATN103), floteuzmab (MGD006), pasotuxizumab (AMG112, MT112), lymphomun (FBTA05), (ATN-103), AMG103 (anti-CD19×anti-CD3 BiTE® antibody) AMG211 (MT111, Medi-1565)

(anti-cacinoembyronic antigen×anti-CD3 antibody), AMG330 (anti-CD33×anti-CD3 BiTE® antibody), AMG212 (anti-PSMA×anti-CD3 BiTE® antibody), AMG160 (anti-PSMA×anti-CD3 BiTE® antibody), AMG420 (B1836909), (anti-BCMA×anti-CD3 BiTE® antibody), AMG-110 (MT110), AMG562 (anti-CD19×anti-CD3 BiTE® antibody), AMG596 (anti-EGFRvIII×anti-CD3 BiTE® antibody), AMG427 (half-life extended anti-FLT3× anti-CD3 BiTE® antibody), AMG673 (half-life extended anti-CD33×anti-CD3 BiTE® antibody), AMG675 (half-life extended anti-DLL3×anti-CD3 BiTE® antibody), AMG701 (half-life extended anti-BCMA×anti-CD3 BiTE® antibody), AMG 424 (anti-CD38 anti-CD3 Xmab), MDX-447, TF2, rM28, HER2Bi-aATC, GD2Bi-aATC, MGD006, MGD007, MGD009, MGDO10, MGDO11 (JNJ64052781), IMCgp100, indium-labeled IMP-205, xm734, LY3164530, OMP-305BB3, REGN1979, COV322, ABT112, ABT165, RG-6013 (ACE910), RG7597 (MEDH7945A), RG7802, RG7813(RO6895882), RG7386, BITS7201A (RG7990), RG7716, BFKF8488A (RG7992), MCLA-128, MM-111, MM141, MOR209/ES414, MSB0010841, ALX-0061, ALX0761, ALX0141; B11034020, AFM13, AFM11, SAR156597, FBTA05, PF06671008, GSK2434735, MEDI3902, MEDI0700, MEDI7352, as well as the molecules or variants or analogs thereof and biosimilars of any of the foregoing.

Multispecific proteins also include trispecific antibodies, tetravalent bispecific antibodies, multispecific proteins without antibody components such as dia-, tria- or tetrabodies, minibodies, and single chain proteins capable of binding multiple targets. Coloma, M. J., et. al., Nature Biotech. 15 (1997) 159-163

An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen.

The term "antibody" includes reference to both glycosylated and non-glycosylated immunoglobulins of any isotype or subclass or to an antigen-binding region thereof that competes with the intact antibody for specific binding. Unless otherwise specified, antibodies include human, humanized, chimeric, multi-specific, monoclonal, polyclonal, heteroIgG, bispecific, and oligomers or antigen binding fragments thereof. Antibodies include the IgG1-, IgG2-IgG3- or IgG4-type. Also included are proteins having an antigen binding fragment or region such as Fab, Fab', F(ab')2, Fv, diabodies, Fd, dAb, maxibodies, single chain antibody molecules, single domain $V_HH$, complementarity determining region (CDR) fragments, scFv, diabodies, triabodies, tetrabodies and polypeptides that contain at least a portion of an immunoglobulin that is sufficient to confer specific antigen binding to a target polypeptide.

Also included are human, humanized, and other antigen-binding proteins, such as human and humanized antibodies, that do not engender significantly deleterious immune responses when administered to a human.

Also included are modified proteins, such as are proteins modified chemically by a non-covalent bond, covalent bond, or both a covalent and non-covalent bond. Also included are proteins further comprising one or more post-translational modifications which may be made by cellular modification systems or modifications introduced ex vivo by enzymatic and/or chemical methods or introduced in other ways.

Proteins of interest may also include recombinant fusion proteins comprising, for example, a multimerization domain, such as a leucine zipper, a coiled coil, an Fc portion of an immunoglobulin, and the like. Also included are proteins comprising all or part of the amino acid sequences of differentiation antigens (referred to as CD proteins) or their ligands or proteins substantially similar to either of these.

In some embodiments, proteins may include colony stimulating factors, such as granulocyte colony-stimulating factor (G-CSF). Such G-CSF agents include, but are not limited to, Neupogen® (filgrastim) and Neulasta® (pegfilgrastim). Also included are erythropoiesis stimulating agents (ESA), such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, epoetin omega, epoetin iota, tissue plasminogen activator, GLP-1 receptor agonists, as well as the molecules or variants or analogs thereof and biosimilars of any of the foregoing.

In some embodiments, proteins may include proteins that bind specifically to one or more CD proteins, HER receptor family proteins, cell adhesion molecules, growth factors, nerve growth factors, fibroblast growth factors, transforming growth factors (TGF), insulin-like growth factors, osteoinductive factors, insulin and insulin-related proteins, coagulation and coagulation-related proteins, colony stimulating factors (CSFs), other blood and serum proteins blood group antigens; receptors, receptor-associated proteins, growth hormones, growth hormone receptors, T-cell receptors; neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins.

In some embodiments proteins bind to one of more of the following, alone or in any combination: CD proteins including but not limited to CD3, CD4, CD5, CD7, CD8, CD19, CD20, CD22, CD25, CD30, CD33, CD34, CD38, CD40, CD70, CD123, CD133, CD138, CD171, and CD174, HER receptor family proteins, including, for instance, HER2, HER3, HER4, and the EGF receptor, EGFRvIII, cell adhesion molecules, for example, LFA-1, Mol, p150,95, VLA-4, ICAM-1, VCAM, and alpha v/beta 3 integrin, growth factors, including but not limited to, for example, vascular endothelial growth factor ("VEGF"); VEGFR2, growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), Cripto, transforming growth factors (TGF), including, among others, TGF-α and TGF-β, including TGF-β1, TGF-β2, TGF-β3, TGF-β4, or TGF-β5, insulin-like growth factors-I and -II (IGF-I and IGF-II), des(1-3)-IGF-I (brain IGF-I), and osteoinductive factors, insulins and insulin-related proteins, including but not limited to insulin, insulin A-chain, insulin B-chain, proinsulin, and insulin-like growth factor binding proteins; (coagulation and coagulation-related proteins, such as, among others, factor VIII, tissue factor, von Willebrand factor, protein C, alpha-1-antitrypsin, plasminogen activators, such as urokinase and tissue plasminogen activator ("t-PA"), bombazine, thrombin, thrombopoietin, and thrombopoietin receptor, colony stimulating factors (CSFs), including the following, among others, M-CSF, GM-CSF, and G-CSF, other blood and serum proteins, including but not limited to albumin, IgE, and blood group antigens, receptors and receptor-associated proteins, including, for example, flk2/flt3 receptor, obesity (OB) receptor, growth hormone receptors, and T-cell receptors; (x) neurotrophic factors, including but not limited to, bone-derived neurotrophic factor (BDNF) and neurotrophin-3, -4, -5, or -6 (NT-3, NT-4, NT-5, or NT-6); (xi) relaxin A-chain, relaxin B-chain, and prorelaxin, interferons, including for example, interferon-alpha, -beta, and -gamma, interleukins (ILs), e.g., IL-1 to IL-10, IL-12, IL-15, IL-17, IL-23, IL-12/IL-23, IL-2Ra, IL1-R1, IL-6 receptor, IL-4 receptor and/or IL-13 to the receptor, IL-13RA2, or IL-17 receptor, IL-1RAP, (xiv) viral antigens, including but not limited to, an AIDS envelope viral antigen, lipoproteins, calcitonin, glucagon, atrial natriuretic factor, lung surfactant, tumor necrosis factor-alpha and -beta, enkephalinase, BCMA, IgKappa, ROR-1, ERBB2, mesothelin, RANTES (regulated on activation normally T-cell expressed and secreted), mouse gonadotropin-associated peptide, Dnase, FR-alpha, inhibin, and activin, integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, MIC (MIC-a, MIC-B), ULBP 1-6, EPCAM, addressins, regulatory proteins, immunoadhesins, antigen-binding proteins, somatropin, CTGF, CTLA4, eotaxin-1, MUC1, CEA, c-MET, Claudin-18, GPC-3, EPHA2, FPA, LMP1, MG7, NY-ESO-1, PSCA, ganglioside GD2, glanglioside GM2, BAFF, ICOS, OPGL (RANKL), myostatin, Dickkopf-1 (DKK-1), Ang2, NGF, IGF-1 receptor, hepatocyte growth factor (HGF), TRAIL-R2, c-Kit, B7RP-1, PSMA, NKG2D-1, programmed cell death protein 1 and ligand, PD1 and PDL1, mannose receptor/hCGP, hepatitis-C virus, mesothelin dsFv[PE38 conjugate, *Legionella pneumophila* (lly), IFN gamma, interferon gamma induced protein 10 (IP10), IFNAR, TALL-1, thymic stromal lymphopoietin (TSLP), proprotein convertase subtilisin/Kexin Type 9 (PCSK9), stem cell factors, Flt-3, calcitonin gene-related peptide (CGRP), OX40L, $\alpha4\beta7$, platelet specific (platelet glycoprotein lib/IIIb (PAC-1), transforming growth factor beta (TFGP), Zona pellucida sperm-binding protein 3 (ZP-3), TWEAK, TSLP, platelet derived growth factor receptor alpha (PDGFR$\alpha$), sclerostin, Jagged-1, and biologically active fragments or variants of any of the foregoing.

AMG506 (FAPx4-1BB targeting DARPin®), AMG592 (IL2 mutein Fc fusion), AMG890 (interfering RNA Lp(a)), AMG 119 (DLL3 CART).

In another embodiment, proteins include abciximab, adalimumab, adecatumumab, aflibercept, alemtuzumab, alirocumab, anakinra, atacicept, basiliximab, belimumab, bevacizumab, biosozumab, blinatumomab, brentuximab vedotin, brodalumab, cantuzumab mertansine, canakinumab, cetuximab, certolizumab pegol, conatumumab, daclizumab, denosumab, eculizumab, edrecolomab, efalizumab, epratuzumab, erenumab, etanercept, etelcalcetide, evolocumab, galiximab, ganitumab, gemtuzumab, golimumab, ibritumomab tiuxetan, infliximab, ipilimumab, ixekizumab, lerdelimumab, lumiliximab, mapatumumab, motesanib diphosphate, muromonab-CD3, natalizumab, nesiritide, nimotuzumab, nivolumab, ocrelizumab, ofatumumab, omalizumab, oprelvekin, palivizumab, panitumumab, pembrolizumab, pertuzumab, pexelizumab, ranibizumab, rilotumumab, rituximab, romiplostim, romosozumab, sargamostim, tezepelumab, tocilizumab, tositumomab, trastuzumab, tratuzumap, ustekinumab, vedolizumab, visilizumab, volociximab, zanolimumab, zalutumumab, and biosimilars of any of the foregoing.

Proteins according to the invention encompass all of the foregoing and further include antibodies comprising 1, 2, 3, 4, 5, or 6 of the complementarity determining regions (CDRs) of any of the aforementioned antibodies. Also included are variants that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a protein of interest. Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

Expression systems and constructs in the form of plasmids, expression vectors, transcription or expression cassettes that comprise at least one nucleic acid molecule as described above are also provided herein, as well host cells comprising such expression systems or constructs. As used herein, "vector" means any molecule or entity (e.g., nucleic acid, plasmid, bacteriophage, transposon, cosmid, chromosome, virus, virus capsid, virion, naked DNA, complexed DNA and the like) suitable for use to transfer and/or transport protein encoding information into a host cell and/or to a specific location and/or compartment within a host cell. Vectors can include viral and non-viral vectors, non-episomal mammalian vectors. Vectors are often referred to as expression vectors, for example, recombinant expression vectors and cloning vectors. The vector may be introduced into a host cell to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art.

"Cell" or "Cells" include any prokaryotic or eukaryotic cell. Cells can be either ex vivo, in vitro or in vivo, either separate or as part of a higher structure such as a tissue or organ. Cells include "host cells", also referred to as "cell lines", which are genetically engineered to express a polypeptide of commercial or scientific interest. Host cells are typically derived from a lineage arising from a primary culture that can be maintained in culture for an unlimited time. Genetically engineering the host cell involves transfecting, transforming or transducing the cells with a recombinant polynucleotide molecule, and/or otherwise altering (e.g., by homologous recombination and gene activation or fusion of a recombinant cell with a non-recombinant cell) to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1990, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69.

A host cell can be any prokaryotic cell (for example, *E. coli*) or eukaryotic cell (for example, yeast, insect, or animal cells (e.g., CHO cells)). Vector DNA can be introduced into prokaryotic or eukaryotic cells via conventional transformation or transfection techniques.

In one embodiment, the cell is a host cell. A host cell, when cultured under appropriate conditions, expresses the protein of interest that can be subsequently collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

By "culture" or "culturing" is meant the growth and propagation of cells outside of a multicellular organism or tissue. Suitable culture conditions for mammalian cells are known in the art. Cell culture media and tissue culture media are interchangeably used to refer to media suitable for growth of a host cell during in vitro cell culture. Typically, cell culture media contains a buffer, salts, energy source, amino acids, vitamins and trace essential elements. Any media capable of supporting growth of the appropriate host cell in culture can be used. Cell culture media, which may be further supplemented with other components to maximize cell growth, cell viability, and/or recombinant protein production in a particular cultured host cell, are commercially available and include RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5 A Medium, Leibovitz's L-15 Medium, and serum-free media such as EX-CELL™ 300 Series, among others, which can be obtained from the American Type Culture Collection or SAFC Biosciences, as well as other vendors. Cell culture media can be serum-free, protein-free, growth factor-free, and/or peptone-free media. Cell culture may also be enriched by the addition of nutrients and used at greater than its usual, recommended concentrations.

Various media formulations can be used during the life of the culture, for example, to facilitate the transition from one stage (e.g., the growth stage or phase) to another (e.g., the production stage or phase) and/or to optimize conditions during cell culture (e.g. concentrated media provided during perfusion culture). A growth medium formulation can be used to promote cell growth and minimize protein expression. A production medium formulation can be used to promote production of the protein of interest and maintenance of the cells, with a minimal of new cell growth). A feed media, typically a media containing more concentrated components such as nutrients and amino acids, which are consumed during the course of the production phase of the cell culture may be used to supplement and maintain an active culture, particularly a culture operated in fed batch, semi-perfusion, or perfusion mode. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount.

A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift.

Host cells may be cultured in suspension or in an adherent form, attached to a solid substrate. Cell cultures can be established in fluidized bed bioreactors, hollow fiber bioreactors, roller bottles, shake flasks, or stirred tank bioreactors, with or without microcarriers Cell cultures can be operated in a batch, fed batch, continuous, semi-continuous, or perfusion mode.

Mammalian cells, such as CHO cells, may be cultured in bioreactors at a small scale of less than 100 ml to less than 1000 mls. Alternatively, large scale bioreactors that contain 1000 mls to over 20,000 liters of media can be used. Large scale cell cultures, such as for clinical and/or commercial scale biomanufacturing of protein therapeutics, may be maintained for weeks and even months, while the cells produce the desired protein(s).

The resulting expressed recombinant protein can then be harvested from the cell culture media. Methods for harvesting protein from suspension cells are known in the art and include, but are not limited to, acid precipitation, accelerated sedimentation such as flocculation, separation using gravity, centrifugation, acoustic wave separation, filtration, including membrane filtration, using ultrafilters, microfilters, tangential flow filters, alternative tangential flow, depth, and alluvial filtration filters. Recombinant proteins expressed by prokaryotes are retrieved inclusion bodies in the cytoplasm by redox folding processes known in the art.

The harvested protein can then be purified, or partially purified, away from any impurities, such as remaining cell culture media, cell extracts, undesired components, host cell proteins, improperly expressed proteins and the like, using one or more unit operations. The term "unit operation" is a term of art and means a functional step that can be performed in a process of purifying a recombinant protein from a liquid culture medium. For example, a unit of operation can involve filtering (e.g., removal of contaminant bacteria, yeast, viruses, or mycobacteria, and/or particulate matter from a fluid including a recombinant protein), capturing, epitope tag removal, purifying, holding or storing, polishing, virus inactivating, adjusting the ionic concentration and/or pH of a fluid including the recombinant protein, and removing unwanted salts.

For example, a unit operation can include steps such as, but not limited to, capturing, purifying, polishing, viral inactivating, viral filtering, and/or adjusting the concentration and formulation containing the recombinant protein of interest. Unit operations can also include holding or storing steps between processing steps. A single unit operation may be designed to accomplish multiple objectives in the same operation, such as capture and viral inactivation.

The capture unit operation includes capture chromatography that makes use of resins and/or membranes containing agents that will bind to the recombinant protein of interest, for example affinity chromatography, size exclusion chromatography, ion exchange chromatography, hydrophobic interaction chromatography (HIC), immobilized metal affinity chromatography (IMAC), and the like. Such materials are known in the art and are commercially available. Affinity chromatography may include a Protein A, Protein G, Protein A/G, Protein L-binding capture mechanism and the like, a substrate-binding capture mechanism, an antibody- or antibody fragment-binding capture mechanism, an aptamer-binding capture mechanism, and a cofactor-binding capture mechanism, for example. In particular, a continuous upstream manufacturing process for bispecific T cell engagers using Protein L is described in WO2019118426. The recombinant protein of interest can be tagged with a polyhistidine tag and subsequently purified from IMAC using imidazole or an epitope, such a FLAG® and subsequently purified by using a specific antibody directed to such epitope.

The one or more capture unit operations includes virus inactivation and/or virus filtration. To ensure patient safety, viral inactivation and viral filtration are necessary components of the purification process when manufacturing protein therapeutics. The fluids to be subjected to virus inactivation and virus filtration can be obtained from effluent streams, eluates, pools, hold or storage vessels.

Enveloped viruses are susceptible to inactivation methods, such as heat inactivation/pasteurization, pH inactivation, UV and gamma ray irradiation, use of high intensity broad spectrum white light, addition of chemical inactivating agents, surfactants, and solvent/detergent treatments, such that they can no longer infect cell, replicate and/or propagate. One method for achieving virus inactivation is incubation at low pH or other solution conditions for achieving the inactivation of viruses. Low pH virus inactivation can be followed with a neutralization unit operation that readjusts the viral inactivated solution to a pH more compatible with the requirements of the following unit operations. It may also be followed by filtration, such as depth filtration, to remove any resulting turbidity or precipitation.

The term "polishing" is used herein to refer to one or more chromatographic steps performed to remove remaining contaminants and impurities such as DNA, host cell proteins; product-specific impurities, variant products and aggregates and virus adsorption from a fluid including a recombinant protein that is close to a final desired purity. For example, polishing can be performed in bind and elute mode by passing a fluid including the recombinant protein through a chromatographic column(s) or membrane absorber(s) that selectively binds to either the target recombinant protein or the contaminants or impurities present in a fluid including a recombinant protein. In such an example, the eluate/filtrate of the chromatographic column(s) or membrane absorber(s) includes the recombinant protein.

The polish chromatography unit operation makes use of resins and/or membranes containing agents that can be used in either a flow-through mode (where the protein of interest is contained in the eluent and the contaminants and impurities are bound to the chromatography medium) or bind and elute mode, where the protein of interest is bound to the chromatography medium and eluted after the contaminants and impurities have flowed through or been washed off the chromatography medium. Examples of such chromatography methods include ion exchange chromatography (IEX), such as anion exchange chromatography (AEX) and cation exchange chromatography (CEX); hydrophobic interaction chromatography (HIC); mixed modal or multimodal chromatography (MM), hydroxyapatite chromatography (HA); reverse phase chromatography and gel filtration.

Critical attributes and performance parameters can be measured to better inform decisions regarding performance of each step during manufacture. These critical attributes and parameters can be monitored real-time, near real-time, and/or after the fact. Key critical parameters such as media components that are consumed (such as glucose), levels of metabolic by-products (such as lactate and ammonia) that accumulate, as well as those related to cell maintenance and survival, such as dissolved oxygen content can be measured. Critical attributes such as specific productivity, viable cell density, pH, osmolality, appearance, color, aggregation, percent yield and titer may be monitored during and after the process. Monitoring and measurements can be done using known techniques and commercially available equipment.

The invention eliminates the need for redundant release sampling of the concentrated, formulated drug substance and the drug product and allows for assay of attributes that are common to both to be done only once, such as at the drug product fill/finish stage, where they can be combined with other drug product attribute testing.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference. What is described in an embodiment of the invention can be combined with other embodiments of the invention.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1 Connected DS-DP Operation

A 50 L bioreactor run was performed to produce a recombinant monoclonal antibody and forward-processed through a series of purification unit operations until the viral filter pool was obtained. An Akta flux 6 skid (GE Healthcare, Piscataway, N.J.) was used for UFDF. A Millipore Pellicon cassette holder was used to house the 30 kD UFDF membrane that totaled an area of 1.14 $m^2$ (Millipore Sigma, Burlington, Mass.). Opticap XL 600 Sterile High Capacity filter (Millipore Sigma, Burlington, Mass.) was used as a bioburden-reduction filter. The final drug substance was collected in a Mobius Single-Use Mixing bag (Millipore Sigma, Burlington, Mass.).

The viral filter pool was used as the starting material for UFDF operation, Polysorbate 80 (PS80) addition and final 0.2-micron filtration. The skid and other product-contacting components were held in 0.2 N sodium hydroxide overnight prior to starting the operations. The formulation buffer used for diafiltration as well as the final protein formulation had a composition of 272 mM Proline, 10 mM Acetate at pH 4.1. A 1% PS80 stock was prepared in the formulation buffer and added to the final UFDF flush buffer and the final protein pool in the retentate tank to achieve 0.01% weight/volume of PS80 in the final DS.

Prior to starting the UFDF operation, a DIW flush was employed and pH of the fluid on the permeate side was checked to ensure that the hydroxide was washed out. Following the DIW flush, normalized water permeability (NWP) was measured to ensure that the filter met the passing criteria. Viral filter pool was charged onto the UFDF skid and a concentration of 70 mg/mL was targeted for the ultrafiltration 1 (UF1) operation. Diafiltration (DF) was performed at 70 mg/mL with the formulation buffer equaling 10 Dia Volumes (DVs). Post-DF the diafiltered pool was recirculated for approximately 10 minutes and a sample was tested for protein concentration from the retentate tank using Solo VPE. The protein concentration and amounts were used to calculate the volume reduction needed to achieve upconcentration of protein pool to 175 mg/mL, in the UF2 operation. During upconcentration, feed pressure, TMP and flux were controlled in a way that TMP was maintained at ~15 psi. After UF2 target at 175 mg/mL was obtained, the target volume to be achieved for 145 mg/mL of final DS concentration was calculated. The required amount of flush buffer was added to reach the target final concentration of 140 mg/mL The amount of PS80 stock that was needed to achieve the 0.01% w/v of PS80 in the retentate tank was calculated and added directly to the protein solution in the retentate tank. The 1% PS 80 stock solution that was prepared in the formulation buffer was used for this purpose.

A 0.01% weight/volume of PS80 stock solution in formulation buffer was prepared and the bioburden reduction filter (Opticap XL 600) was flushed at ~ 80 L/$m^2$ to saturate the charge sites on the filter with PS80. The outlet of the filter was connected with a Y in a way that one arm of the Y was connected to the flush buffer bag for collecting flush buffer and the other arm was connected to the Mobius bag used to collect the final DS. The remaining amount of trace buffer in the SHC filter housing was removed by pumping air into the filter. After removing the remaining buffer from the filter, the flush-buffer collection bag was clamped and DS filtration in the product-collection bag was initiated. Prior to filtration, final DS concentration samples were obtained directly from the retentate tank and three concentration measurements were obtained.

Two viral filter pools (sub-lots) were combined to make one UFDF/DS/DP lot. The product quality assays, common between DS and DP, were tested only once. The quality target product profile for the drug substance and drug product processes were compared, all were within specification.

The UFDF/DS/DP lot was then subjected to filtration using a 0.24 bioburden reduction filter and collected into a storage bag. The bag was connected to a Vanrx SA25 unit (Burnaby, British Columbia, Canada) and the bulk drug product sterile filtered prior to fill/finish of the drug product.

Example 2 UFDF Membrane Cycling Following Buffer Cleaning

The experiment assessed ultrafiltration-diafiltration performance using scaled down single use stabilized cellulose based, hydrophilic membranes with membrane reuse after equilibration buffer cleaning representative of single use UFDF skid in manufacturing to determine the effect of cycling and feed conditions on the UFDF process and product quality performance, using a half-life extended bispecific T cell engager feed stream.

Frozen eluate pool material from a multimodal anionic (MMA) column comprising a half-life extended bispecific T cell engager, HLE BiTE®, was thawed before processing. The eluate pool material was then loaded on to three equilibrated stabilized cellulose based, hydrophilic membranes, Sartocon Slice 200 ECO (10 kD MWCO cutoff) (Sartorius, Goettingen, Germany), columns (A, B, C) with membrane area 0.018 $m^2$, feed pressure in the range of 20-36 psi, loading at 71.4 g/$m^2$ for a first run. Samples were concentrated (UF1) to an intermediate target in the range of 0.5 g/L to 4 g/L, see Table 1 for initial concentration targets, the sample was dia-filtered with 10 volumes of a formulation buffer, 10 mM Acetate, 180 mM NaCl, pH 5.0. The samples were recovered in a pool vessel, followed by system chases to recover the pool to a sufficient volume to mix and sample in the recovery vessel. The TFF pool was then diluted to a target concentration of 1-2 g/L, with formulation buffer as needed.

After the first cycle, the membranes were flushed with equilibrium buffer, 100 mM acetate, 180 mM NaCl, pH 5.0, and a normalized water permeability [NWP] test was performed on each membrane to determine membrane consistency. Normalized water permeability (NWP) is a determination of the cleanliness of a membrane following cleaning. The passage of clean water through the membrane was measured under standard pressure and temperature conditions. The rate of clean water flux through each membrane was measured as liters per membrane area per hour (L/$m^2$-h). Water flux divided by the transmembrane pressure is the normalized water permeability or NWP (L/$m^2$-h-bar). The NWP values were compared to initial (pre-process) levels and may be analyzed for trends over time.

UFDF eluates were collected as bulk pools for all runs and analyzed for product quality. Product quality attributes were assessed in the viral filtrate: high molecular weight (HMW) impurities were determined using Size Exclusion Ultra High-Performance Liquid Chromatography (SE-UHPLC), Clips were determined using Capillary Electrophoresis-Sodium Dodecyl Sulfate (CE-SDS or r-CE) analysis under reduced conditions, and charge profile, acidic and basic variants, were determined using Cation-Exchange High Performance Liquid Chromatography (CEX-HPLC).

Membranes B and C were then subjected to two more cycles, as outlined in Table 1.

All membranes were challenged at high loads, loading to 71.4 g/$m^2$ of membrane area instead of a typical 55 g/$m^2$. Run 1 was one full cycle performed on a single Sartocon membrane (A) without any additional cycles for that membrane. Runs 2-4 were performed on a single Sartocon membrane (B) with no caustic chemical cleaning, only a buffer flush, in between cycles, each run performed on a successive day over a period of three days, one cycle per day (pause of 10-12 hours in between runs). Runs 5-7 were performed on a single Sartocon membrane (C) with no caustic chemical cleaning, only a buffer flush, in between cycles and the runs were performed in quick succession without any pauses in-between cycles. All of the experiments were performed using an AKTA crossflow UF/DF skid (GE Healthcare, Chicago, Ill.).

TABLE 1

Experimental details for the membrane runs.

| Run # | Run description | | Experiment condition | Initial [UF1] Concentration target (mg/mL) |
|---|---|---|---|---|
| 1 | Low Con (Low concentration) | A | Single membrane with just one cycle with a buffer flush once the final pool was collected. | 1.95 |
| 2 | High Con (High Concentration) | B | First cycle with buffer flush once the final pool was collected, no caustic cleaning. | 3.20 |
| 3 | Center Point 1 | | Second cycle the following day (10-12 hour pause). Again, a buffer flush once the final pool was collected, no caustic cleaning. | 2.30 |
| 4 | Center Point 2 | | Third cycle the following day (10-12 hour pause). No flush or cleaning after final pool was collected. | 2.30 |
| 5 | Multi-Run Center Point 1 | C | First run with buffer flush once final pool was collected. | 2.30 |
| 6 | Multi-Run Center Point 2 | | Second run started immediately following the completion of Run 5. A buffer flush was performed once final pool was collected. | 2.30 |
| 7 | Multi-Run Center Point 3 | | Third run immediately followed completion of Run 6. No buffer flush or caustic cleaning was performed after collection of final pool. | 2.30 |

Figure 2:
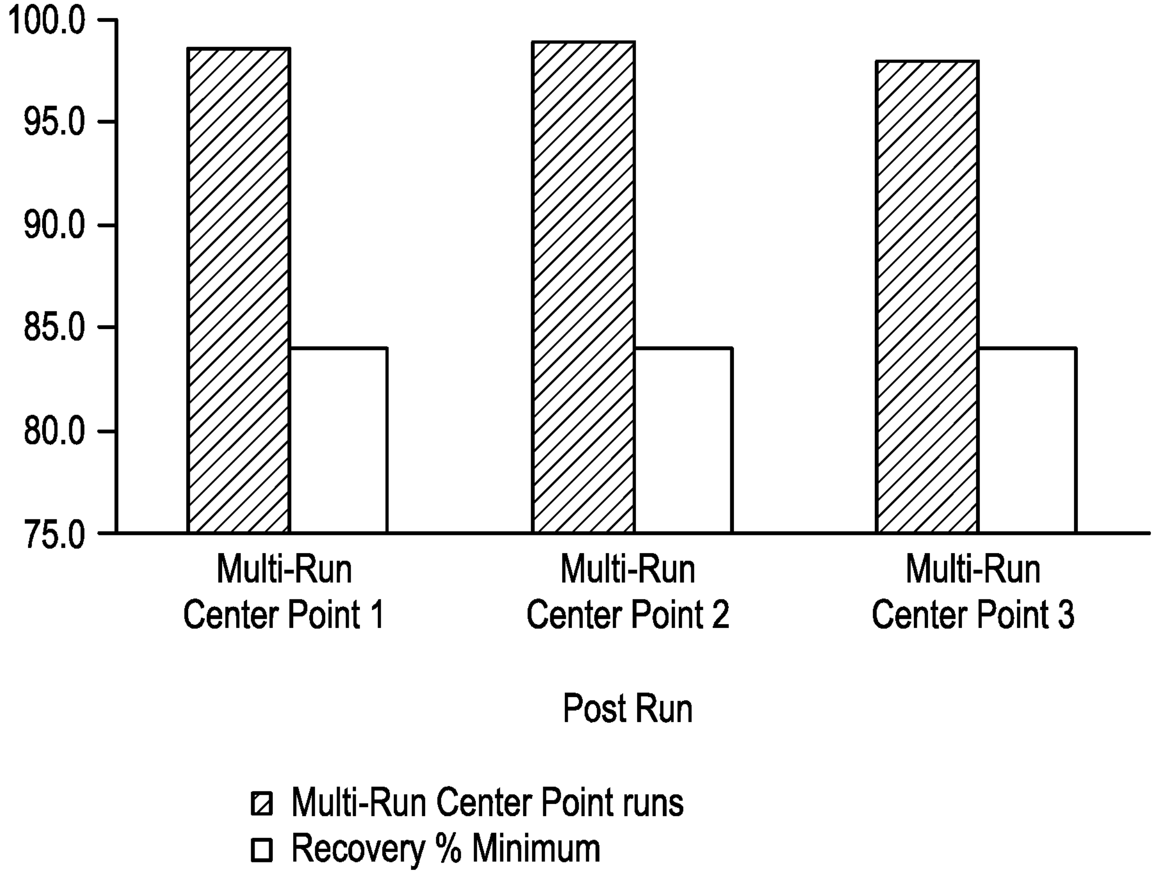
FIG. 2: NWP Recovery % post set of multi-run center point runs 1 to 3 compared to recovery % minimum. Black bars are multi-run center point runs. Gray stippled columns are recovery % minimum.

FIG. 2 shows the NWP recovery percentages values for the Sartocon membrane post each run starting from multi-run center point 1 [Run 5]. Also shown, the minimum NWP recovery % observed after 20 cycles, performed on similar a membrane during process characterization. Post multi-run center point 3 [Run 7] NWP recovery % was higher compared to the recovery % minimum. This observation shows that post three cycles with just buffer cleaning in between the runs was good enough to maintain the NWP recovery % well above the minimum observed for 20 cycles. This further provided data that even without any type of caustic chemical cleaning [no sodium hydroxide CIP for example] the membrane did not lose permeability and was sufficient to use for reprocessing after only a buffer flush, at least for three cycles.

Table 2 summarized the product quality values (HMW %, Clips %, Acidic %, Basic %) of the load and final pools for all runs performed. The final pool HMW % for all runs, irrespective of the higher loading and high initial concentration were comparable. Overall, product quality performance for a stabilized cellulose based, hydrophilic membrane as modeled in these experiments met clinical and commercial process needs and specifications. From a process performance perspective, rinsing the membranes with equilibrium buffer was also sufficient to perform additional cycling loading all the way up to 71.4 g/$m^2$.

TABLE 2

Product quality data for all the runs: HMW %, Clips %, Acidic % and Basic %

| Run description | Load Pool | Final Pool |
|---|---|---|
| **HMW** | | |
| Low Concentration | 2.88% | 0.81% |
| High Concentration | 2.97% | 0.86% |
| Center Point 1 | 3.00% | 0.74% |
| Center Point 2 | 2.23% | 0.25% |
| Multi-Run Center Point 1-3 | 3.15% | 0.34% |
| **Clips %** | | |
| Low Concentration | 3.751 | 2.65 |
| High Concentration | 2.314 | 2.808 |
| Center Point 1 | 2.669 | 3.436 |
| Center Point 2 | 4.747 | 3.047 |
| Multi-Run Center Point 1-3 | 3.843 | 2.435 |
| **Acidic** | | |
| Low Conc | 2.31% | 2.50% |
| High Conc | 2.40% | 2.56% |
| Center Point 1 | 2.42% | 2.56% |
| Center Point 2 | 2.33% | 2.53% |
| Multi-Run Center Point 1-3 | 2.33% | 2.50% |
| **Basic** | | |
| Low Conc | 17.57% | 16.99% |
| High Conc | 17.62% | 17.14% |
| Center Point 1 | 17.59% | 17.14% |
| Center Point 2 | 18.42% | 17.42% |
| Multi-Run Center Point 1-3 | 17.71% | 17.36% |

Example 3 High Membrane Loading and Increased Diavolumes for UFDF

This experiment assessed ultrafiltration-diafiltration performance using a regenerated cellulose membrane specifically challenged with high membrane loading and increased number of diavolumes on product quality performance, using a half-life extended bispecific T cell engager molecule feed stream.

Frozen eluate pool material from a multimodal anionic (MMA) column comprising a half-life extended bispecific T cell engager, was thawed before processing. The eluate pool material was then loaded on to a regenerated cellulose membrane (Pellicon 3 (10 kD MWCO cutoff) (EDM Millipore, Danvers, Mass.)), with membrane area 0.0088 $m^2$. The experimental conditions are summarized Table 3. All the experiments were performed using an AKTA crossflow UF/DF skid (GE Healthcare, Chicago, Ill.).

The filter was equilibrated with 100 mM Acetate, 180 mM NaCl, pH 5.0. Following membrane equilibration, the eluate pool material was concentrated to a desired initial concentration, see Table 3, feed flow was ≥10 L/$m^2$. Following concentration, the pool material was dia-filtered with 10 or 13 diavolumes of a formulation buffer, 10 mM glutamate, 9% sucrose, pH 4.2, see Table 3. The product was recovered into a pool vessel, followed by system chases to recover the pool to a sufficient volume and sample in the recovery vessel. The TFF pool was then diluted to a target concentration with formulation buffer.

TABLE 3

Experimental details for high loading and higher diavolume (DV)

| Run # | Run description | Loading ($g/m^2$) | Diafdtration volume [DV] | Initial [UF1] concentration target (mg/mL) |
|---|---|---|---|---|
| 1 | 85 $g/m^2$_10DV | 85 | 10 | 5.0 |
| 2 | 110 $g/m^2$_10DV | 110 | 10 | 2.5 |
| 3 | 110 $g/m^2$_13DV | 110 | 13 | 7.0 |
| 4 | 170 g/m2_13DV | 170 | 13 | 8.5 |

Run 4 had the highest MHW % in comparison with the other runs, but below an acceptable quality target of <5%, Table 4.

TABLE 4

Product quality data for all the runs: HMW %, Clips %, Acidic % and Basic %

| Run description | Load Pool | Final Pool |
|---|---|---|
| HMW % | | |
| 85 $g/m^2$_10DV | 1.8 | 0.6 |
| 110 $g/m^2$_10DV | 3.3 | 0.5 |
| 110 $g/m^2$_13DV | 3.3 | 1.7 |
| 170 $g/m^2$_13DV | 3.7 | 2.1 |
| Clips % | | |
| 85 $g/m^2$_10DV | 1.12 | 1.03 |
| 110 $g/m^2$_10DV | 1.99 | 2.46 |
| 110 $g/m^2$_13DV | 1.87 | 1.95 |
| 170 $g/m^2$_13DV | 1.70 | 1.4 |
| Acidic % | | |
| 85 $g/m^2$_10DV | 2.8 | 3.1 |
| 110 $g/m^2$_10DV | 2.4 | 2.4 |
| 110 $g/m^2$_13DV | 3.4 | 3.4 |
| 170 $g/m^2$_13DV | 3.3 | 3.4 |
| Basic % | | |
| 85 $g/m^2$_10DV | 14.1 | 14.2 |
| 110 $g/m^2$_10DV | 20.9 | 20.5 |
| 110 $g/m^2$_13DV | 21.1 | 20.4 |
| 170 $g/m^2$_13DV | 21.4 | 20.7 |

Example 4 Viral Filtration of a Formulated Bispecific T Cell Engager

This experiment demonstrated the viral filtration of a half-life extended bispecific T cell engager (HLE BiTE®) in formulation buffer.

Half-life extended bispecific T cell engagers at various concentrations in a formulation buffer, 9% Sucrose, 10 Mm Glutamate, pH 4.2, was evaluated with respect to process and product quality performance using a hydrophilized polyvinylidene fluoride (PVDF) hollow fiber filter (Plavona™ BioEx) and a cuprammonium-regenerated cellulose hollow fiber filter (Planova 20N), 0.001 $m^2$ virus removal filters (Asahi Kasei Bioprocesses, Glenville, Ill.) in a filter train at constant pressure. The filter train consisted of a pressure regulator connected to a pressure reservoir having a valve that was connected to the virus removal filter. The virus removal filter opened directly to a collection vessel attached to a balance. The filter train was connected to a computer for data collection and to a compressed air supply for pressure regulation.

Volumetric Throughput was determined by measuring the amount of filtrate [mL or L] collected at predetermined time intervals then divided by the effective filtration surface area of the filter being used. Flux decay was determined based on what the instantaneous flux is divided by the initial flux and then subtracting that value from 1 (Flux decay=1−flux loss=1−[J/J0]). The initial flux, −J0, was the buffer permeability, so flux decay was normalized with regard to −J0 and is represented as a percent. Viral filtrates were collected as bulk pools for all runs and analyzed for product quality. Particular product quality attributes were assessed in the virus filtrate: high molecular weight (HMW) impurities were determined using Size Exclusion Ultra High-Performance Liquid Chromatography (SE-UHPLC), Clips were determined using Capillary Electrophoresis-Sodium Dodecyl Sulfate (CE-SDS or r-CE) analysis under reduced conditions, and charge profile, acidic and basic variants, were determined using Cation-Exchange High Performance Liquid Chromatography (CEX-HPLC).

The experiments were performed using aliquots of the feed material (thawed or fresh) and run under the conditions for each of Runs 1-6 as provided in Table 5. The feed material was a purified eluate pool containing a bispecific T cell engager formulated with 10 mM glutamate, 9% Sucrose, pH 4.2.

TABLE 5

Experimental run details for formulation buffer matrix

| Run | Filter | Conc. (g/L) | Feed description | Feed Condition | Filtration Pressure (PSI) |
|---|---|---|---|---|---|
| 1 | 20N | 3.12 | High concentration | Fresh, pH 4.2 | 17 |
| 2 | BioEX | 1.79 | BioEx center point | thawed on day of VF run, pH 4.2 | 49.5 |
| 3 | 20N | 1.79 | Center point | thawed on day of VF run, pH 4.2 | 19 |
| 4 | 20N | 1.79 | High volume | thawed on day of VF run, pH 4.2 | |
| 5 | 20N | 1.79 | Extended hold | 36 hours hold sample at room temperature, pH 4.2 | |
| 6 | 20N | 1.59 | Low concentration | Adjusted to pH 5.0 | |

Table 6 show the hydraulic performance of each run separated by feed condition. Results are displayed in terms of normalized flux decay (compared to buffer permeability) as a function of volumetric throughput (L/m$^2$).

TABLE 6

Formulation buffer matrix- Filtration summary results

| Planova Filter Details | | Solution details Conc. | Throughput | Flux decay |
|---|---|---|---|---|
| Run | Type | (g/L) | (L/m$^2$) | (%) |
| 1 | 20N | 3.12 | 36 | 73.3 |
| 2 | BioEX | 1.79 | 171 | 70.7 |
| 3 | 20N | 1.79 | 201 | 47.3 |
| 4 | | 1.79 | 501 | 80 |
| 5 | | 1.79 | 201 | 46.2 |
| 6 | | 1.59 | 77 | 78 |

Figure 3:
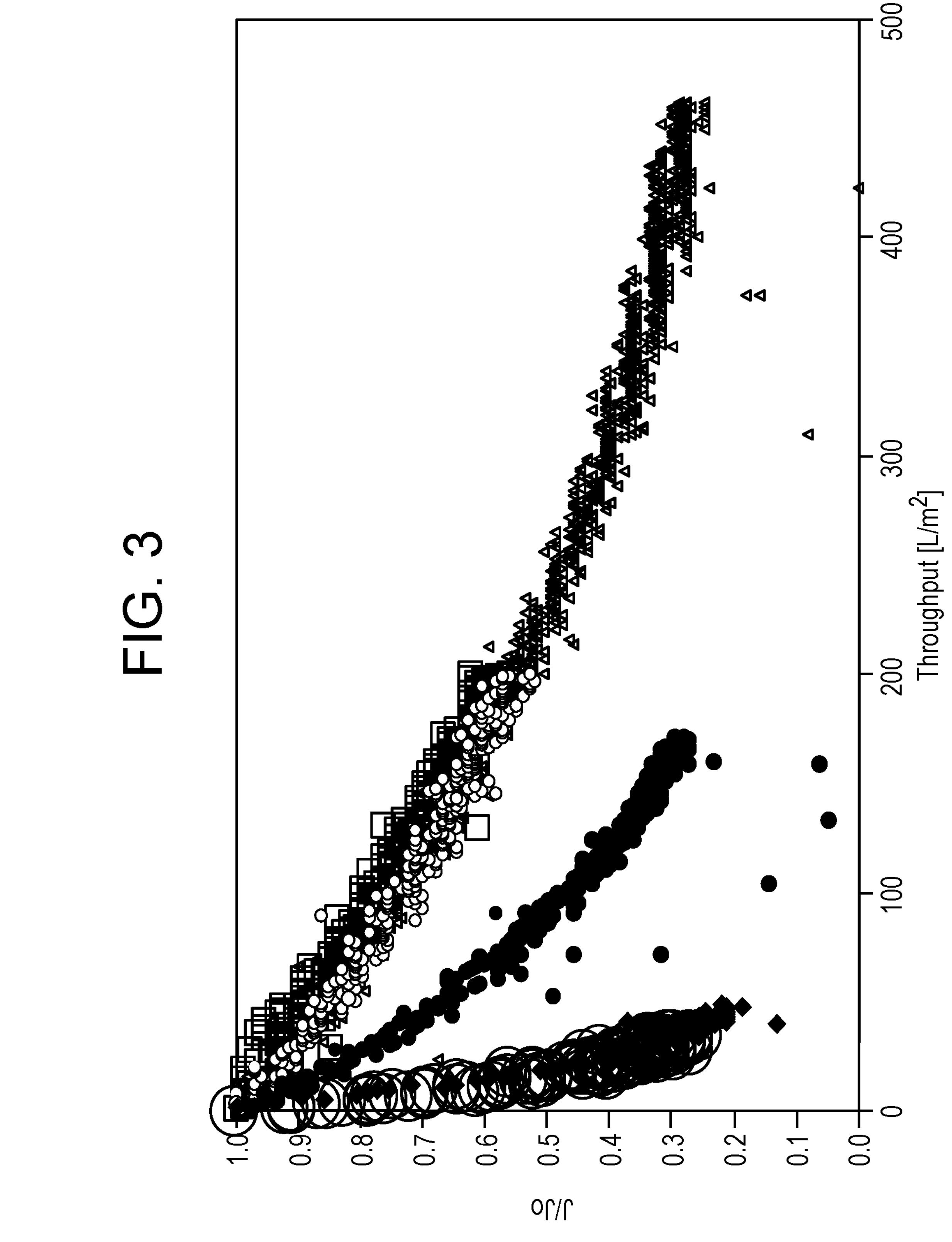
FIG. 3: Flux decay vs throughput for runs in formulation buffer matrix-cuprammonium-regenerated cellulose filter pH 4.2—High concentration [open black circles], pH 4.2—High volume [black open triangle], pH 4.2—Extended hold [black open square], pH 4.2—Centerpoint [grey filled circles], pH 4.2—PVDF filter [black filled circles], and pH 5.0—Low concentration [diamond shape patterned fill]
Figure 4A:
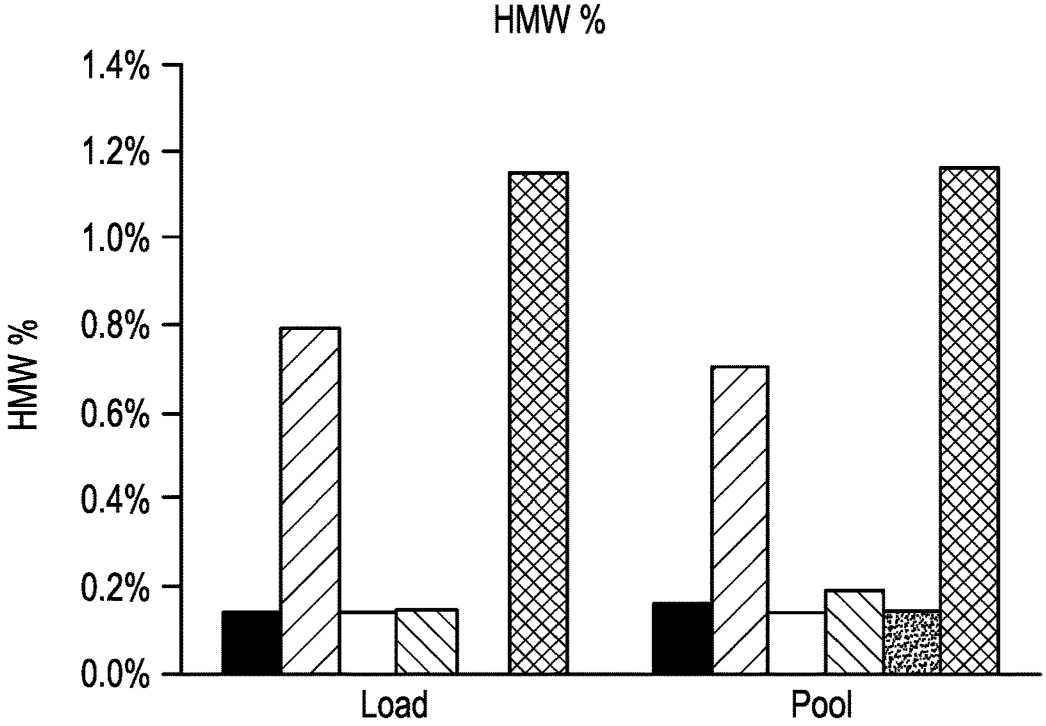
FIG. 4A: HMW %.
Figure 4B:
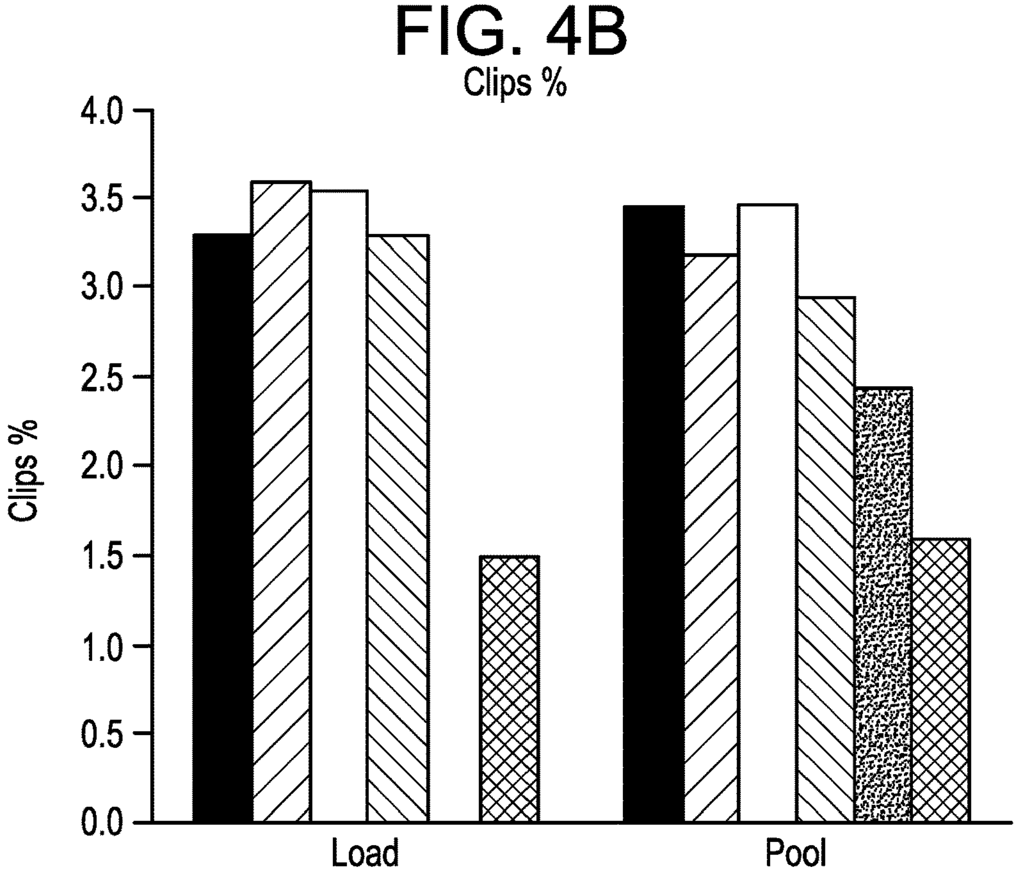
FIG. 4B: CLIPS %.
Figure 4C:
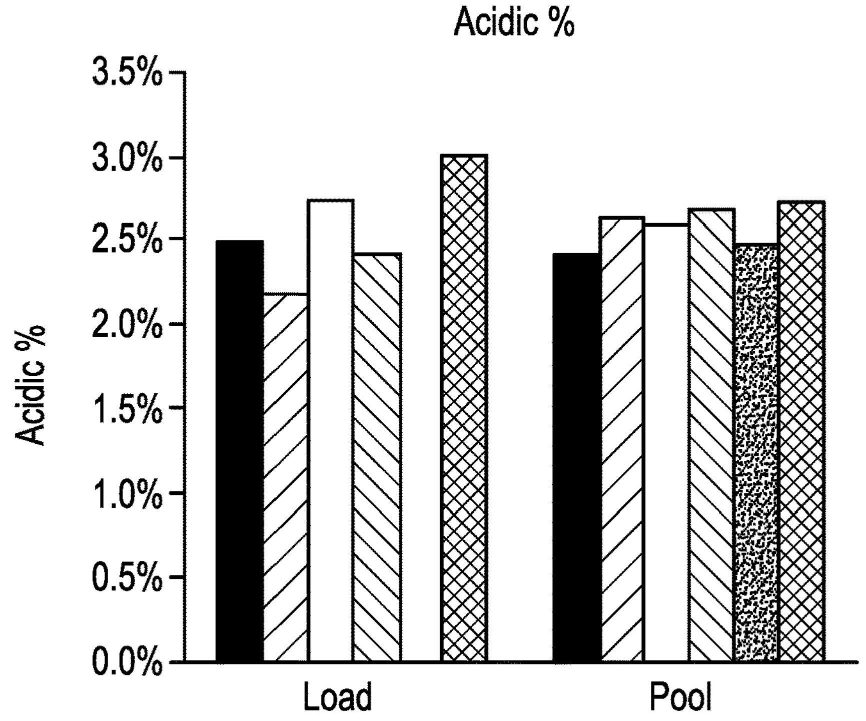
FIG. 4C: Basic %.
Figure 4D:
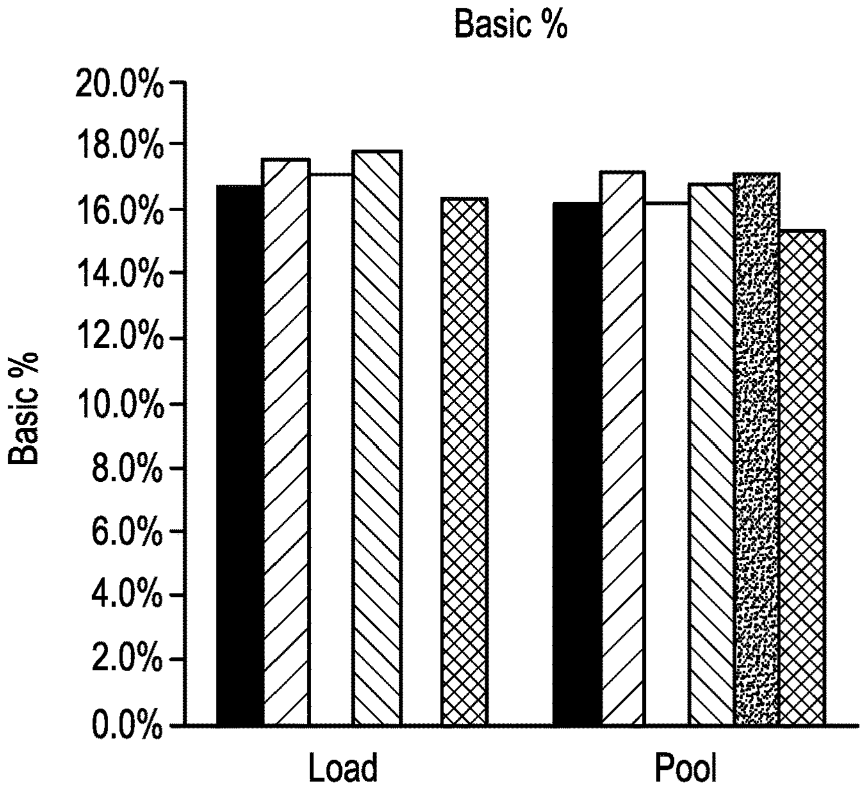
FIG. 4D: Acidic %.

FIG. 3 shows the impact of different feed conditions on volumetric throughput. For all the runs there was no impact of feed condition (fresh, extended hold and high volume) on flux decay except for high concentration and high pH runs.

Product Quality

There was an increase in HMW at higher concentration (Run 1) as well as an increase in pH (Run 6) resulting in a flux decay of 73% and 78% respectively. The filterability for the PVDF filter at 200 L/m$^2$, was lower than the cuprammonium-regenerated cellulose filter with a higher flux decay, see FIG. 4 A HMW %, 4B Clips %, 4C Basic %, and 4D Acidic %.

In a second experiment, a half-life extended bispecific T cell engager formulated in a chromatography pool buffer, 100 mM Acetate, 180 mM Sodium Chloride, pH 5.0, and evaluated with respect to process and product quality performance. A cuprammonium-regenerated cellulose hollow fiber virus removal filter (Plavona™ 20N), 0.001 m$^2$ (Asahi, Glenville, Ill.) was used in the filter train. The experiment was performed using aliquots of the feed material run under the conditions for each of Runs 7-13 as provided in Table 7.

TABLE 7

Experiment details for chromatography pool buffer matrix

| Run # | Concentration (mg/mL) | Feed description | Feed condition (pH, conductivity) | Pressure (psig) |
|---|---|---|---|---|
| 7 | 1.77 | Center point | 5, 23 | 19 |
| 8 | 3.15 | Medium concentration, center point | 5, 23 | 19 |
| 9 | 1.77 | Center point, high conductivity | 5, 28 | 19 |
| 10 | 1.77 | Low pressure | 5, 28 | 14 |
| 11 | 6.82 | High concentration, high pH | 5.3, 28 | 19 |
| 12 | 6.82 | High concentration, low pH, | 4.54, 28 | 19 |
| 13 | 1.77 | Medium pressure | 5, 23 | 17 |

Figure 5:
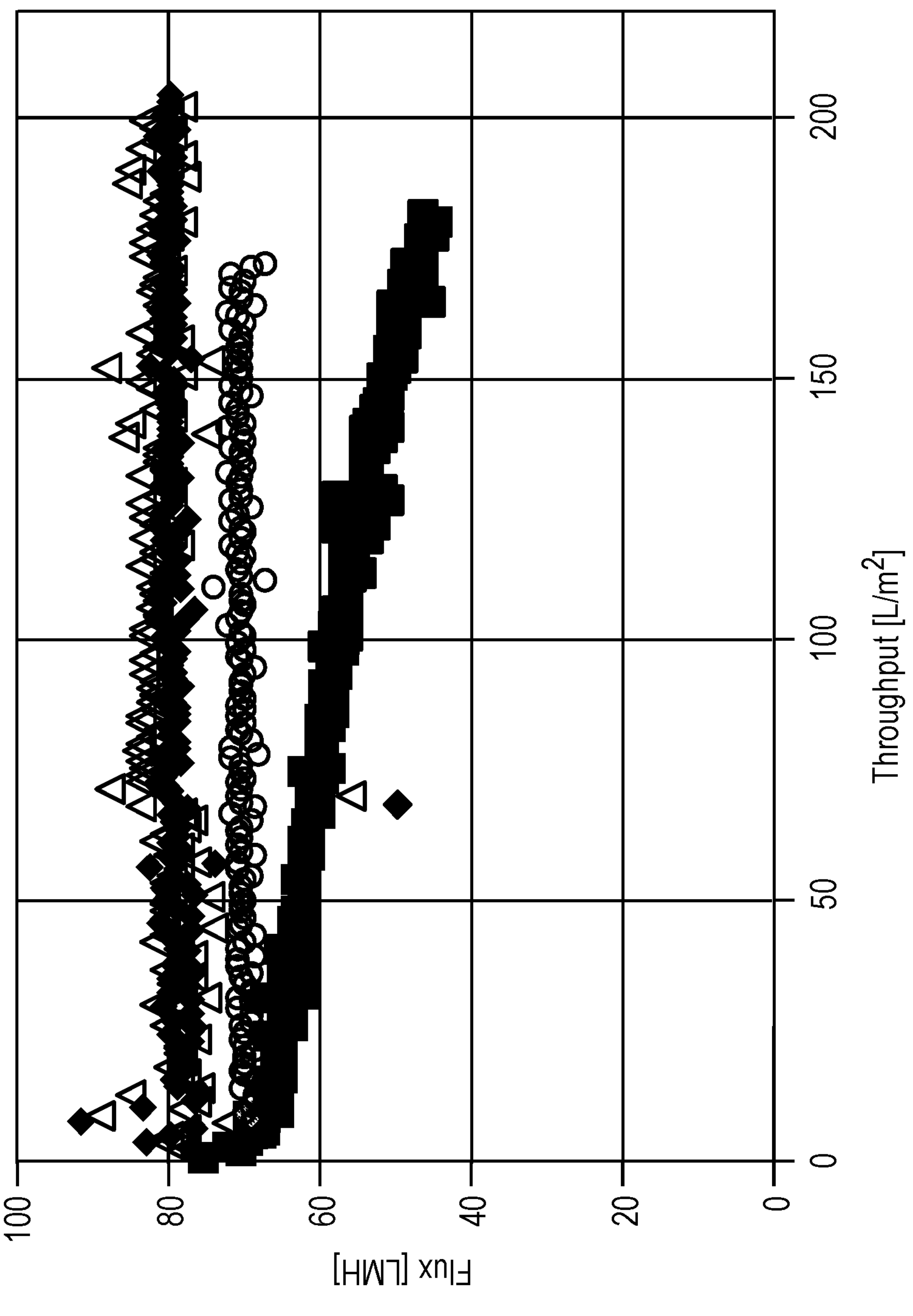
FIG. 5: Flux vs. load challenge for 0.001-m2 20N filtration cuprammonium-regenerated cellulose filter at 1.77 g/L of product [Open black triangle], 3.15 g/L [Grey solid diamond], and 6.82 g/L [open black circle], [solid black square]. All load material was filtered at 19 PSI.
Figure 6A:
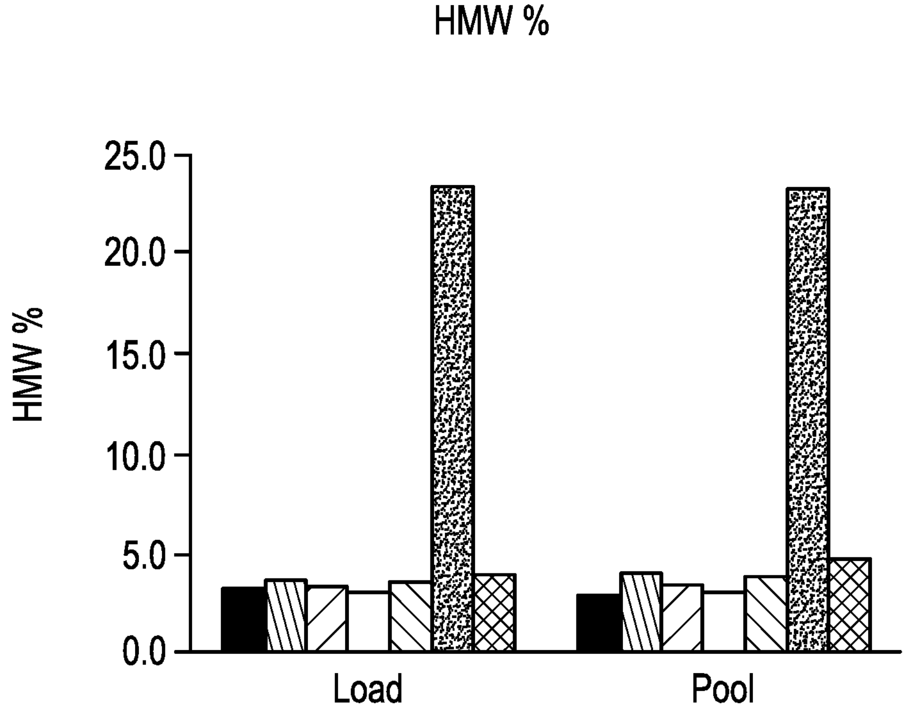
FIG. 6A: HMW %.
Figure 6B:
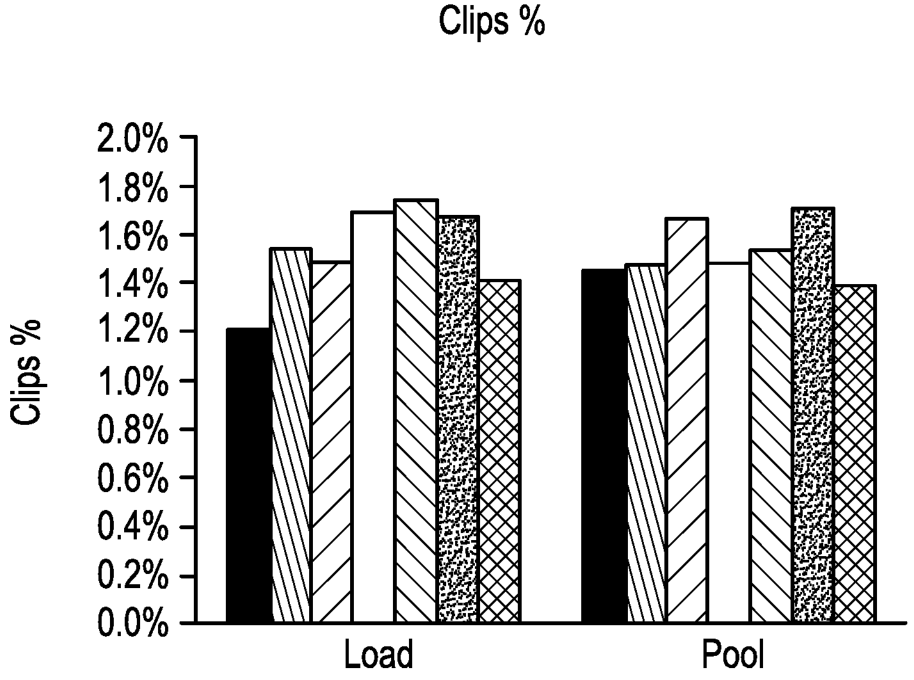
FIG. 6B: CLIPS %.
Figure 6C:
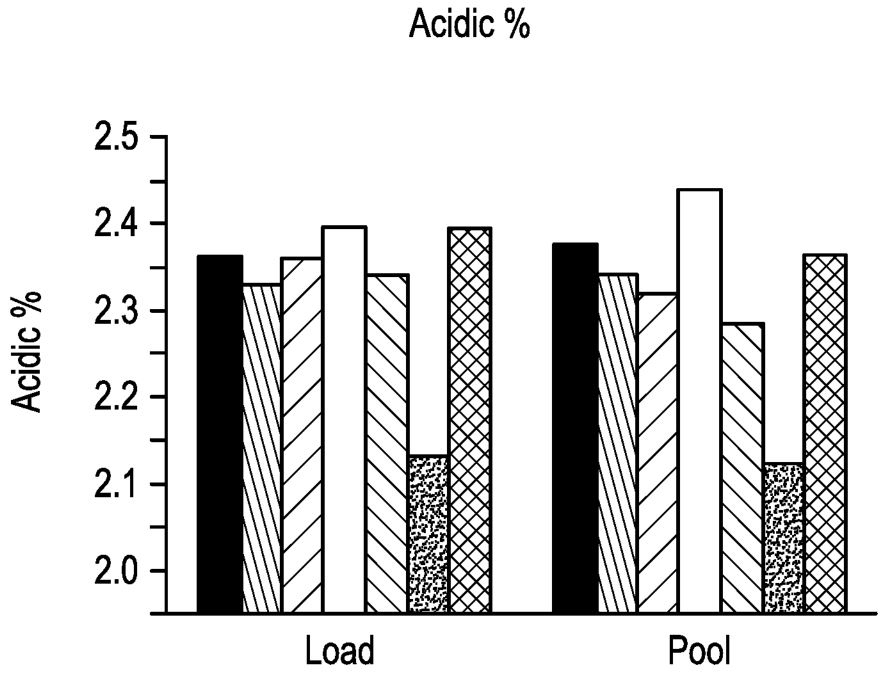
FIG. 6C: Basic %.
Figure 6D:
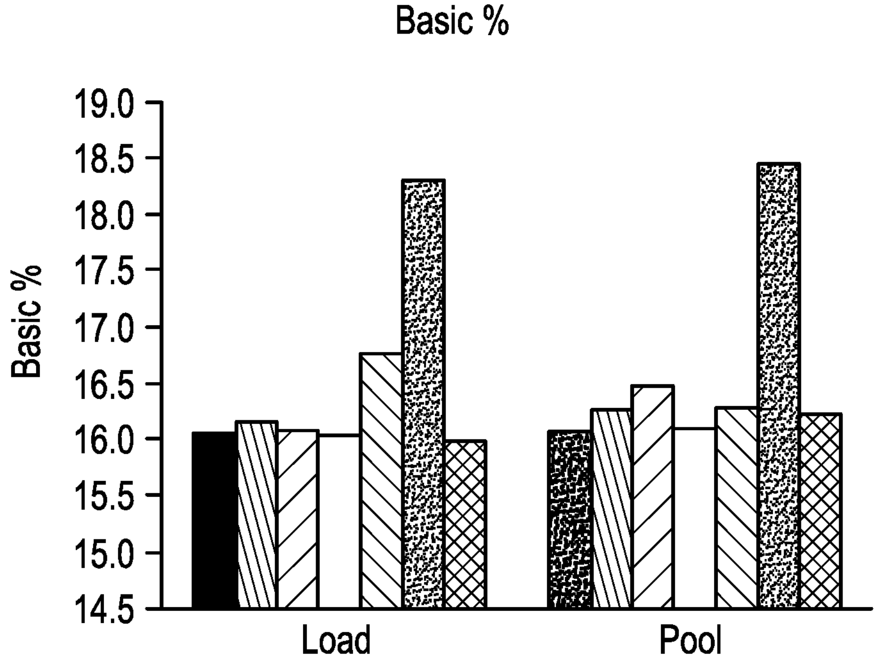
FIG. 6D: Acidic %.

FIG. 5 shows the impact of concentration, pH and conductivity in chromatography buffer matrix. At pH 5.0, both concentrations (1.77 g/L and 3.15 g/L) were within a flux decay of 13% (Table 8 At pH 5.3, with a concentration of 6.82 g/L, flux decay was minimal (3%) whereas at pH 4.5, the flux decay was significant (32%). This could be attributed to an increase in aggregates (>20%, at low pH, FIG. 6 A. Conductivity had no impact on viral filtration for the tested conditions. Irrespective of pressure (14, 17 or 19 psi) there was minimal flux decay (Table 8).

TABLE 8

Filtration results for chromatography buffer matrix

| Run # | Concentration (mg/mL) | Feed condition (pH, conductivity) | Throughput (L/m2) | Flux Decay at 150 L/m2 (%) |
|---|---|---|---|---|
| 7 | 1.77 | 5, 23 | 202 | 10 |
| 8 | 3.15 | 5, 23 | 204 | 13 |
| 9 | 1.77 | 5, 28 | 404 | 1 |
| 10 | 1.77 | 5, 28 | 203 | 3 |
| 11 | 6.82 | 5.3, 28 | 172 | 3 |
| 12 | 6.82 | 4.54, 28 | 182 | 32 |
| 13 | 1.77 | 5, 23 | 204 | 2 |

Although the runs in formulation buffer matrix had poorer flux compared to the runs in a chromatography buffer, they were still within an acceptable range for use.

Example 5 Process and Product Quality Performance of Bispecific T Cell Engagers During Virus Filtration Viral filters are typically operated under one of two modes, the first is a constant pressure mode where incoming pressure is kept constant by using pressure regulators. In this mode, there is flux which drops as time progresses and volumetric throughput increases [L/m$^2$] and is plotted as flux decay vs volumetric throughput [L/m$^2$]. In the second, a constant flow mode, the flux is kept constant by using a pump to push the feed load at a constant flow rate. In this mode the pressure increases over time, as volumetric throughput increases [L/m$^2$]. This is typically plotted as resistance [inverse of permeability] vs volumetric throughput [L/m$^2$].

This experiment assessed viral filtration in normal flow filtration under constant pressure mode and would extend to under constant flow mode and the effect of feed conditions [pH, conductivity and concentration] on the viral filter hydraulic performance and product quality attributes in the presence and absence of various prefilters, for a half-life extended bispecific T cell engager (HLE BiTE® A) feed stream.

Viresolve® Pro (VPro), a polyethersulfone (PES) (3.1 cm$^2$ parvovirus retentive filter) viral filter, was tested alone and in combination with four filters: two surface modified prefilters, Viresolve® Pro Shield (Shield) (3.1 cm$^2$) and Viresolve® Pro Shield H (Shield H) (3.1 cm$^2$), surface modified polyethersulfone membrane filters); and two depth filters Viresolve® Prefilter, (VPF) (5 cm$^2$), an adsorptive depth filter, and Millistak+® HC Pro X0SP (X0SP) (5 cm$^2$/3.1 cm$^2$), a synthetic depth filter composed of a double layer silica filter aid with polyacrylic fiber, all from MilliporeSigma (Burlington, Mass.).

A half-life extended bispecific T cell engager, BiTE® A, feed stream was evaluated with respect to process and product quality performance of these filter combinations.

The experiments were performed using a compressed air supply connected through a pressure regulator connected to a pressurized feed vessel having a valve that connected to either the surface modified membrane prefilter or the depth filter, which in turn was connected to the viral filter. As a control, the feed vessel valve was connected directly to the viral filter device alone. The viral filter opened directly to a collection vessel attached to a balance. The filter train was connected to a computer for data collection and to a compressed air supply for pressure regulation.

The feed side pressure for the viral filter was set to a constant 30 psi and the filtrate volume was measured at pre-determined time intervals. During filter set up, the viral filter device and the surface modified membrane prefilter or the depth filter device were separately flushed with water at 30 psi. The viral filter device and prefilter or depth filter device were then connected, and a buffer flush was performed at 30 psi. Average water and buffer flow rates and permeabilities for each viral filter and prefilter or depth filter device was recorded and were within the recommended limits.

Volumetric Throughput was determined by measuring the amount of filtrate [mL or L] collected at predetermined time intervals then divided by the effective filtration surface area of the filter being used, (3.1 cm2 for the VPro device). Flux decay was determined based on what the instantaneous flux is divided by the initial flux and then subtracting that value from 1 (Flux decay=1−flux loss=1−[J/J0]). The initial flux, −J0, was the buffer permeability, so flux decay was normalized with regard to −J0 and is represented as a percent. Viral filtrates were collected as bulk pools for all runs and analyzed for product quality.

Particular product quality attributes were assessed in the viral filtrate: high molecular weight (HMW) impurities were determined using Size Exclusion Ultra High Performance Liquid Chromatography (SE-UHPLC), Clips were determined using Capillary Electrophoresis-Sodium Dodecyl Sulfate (CE-SDS or r-CE) analysis under reduced conditions, and charge profile, acidic and basic variants, were determined using Cation-Exchange High Performance Liquid Chromatography (CEX-HPLC).

The feed material, a purified eluate pool containing BiTE® A, was thawed before processing. After thawing, aliquots of the feed material were adjusted to the target conditions as described in Table 9 (pH, conductivity, concentration). The conditions for each of Runs 1-16 is provided in Table 10.

TABLE 9

Feed Design conditions

| Process Fluid | pH | Conductivity (mS/cm) | Concentration (g/L) | Buffer Components |
|---|---|---|---|---|
| BiTE ® A (midpoint pH, low concentration) | 5 | 23 | 1.75 | 100 mM Sodium Acetate, 180 mM NaCl |
| BiTE ® A (low pH, low concentration) | 4.2 | 23 | 1.75 | 100 mM Sodium Acetate, 180 mM NaCl |
| BiTE ® A (high pH, low concentration) | 6 | 23 | 1.75 | 100 mM Sodium Acetate, 180 mM NaCl |
| BiTE ® A (high concentration, low pH) | 4.2 | 28 | 7 | 100 mM Sodium Acetate, 180 mM NaCl |
| BiTE ® A (high concentration, high pH) | 6 | 28 | 7 | 100 mM Sodium Acetate, 180 mM NaCl |

TABLE 10

Experimental run conditions based on Table 10

| Run # | Name [Pre-filter + Viral Filter combination] | pH | Conductivity (mS/cm) | Concentration (g/L) |
|---|---|---|---|---|
| 1 | VPro alone (Midpoint pH, low concentration) | 5.0 | 23 | 1.75 |
| 2 | VPro + Shield (Midpoint pH, low concentration) | 5.0 | 23 | 1.75 |
| 3 | VPro + Shield H (Midpoint pH, low concentration) | 5.0 | 23 | 1.75 |
| 4 | VPro alone (Low pH, low concentration) | 4.2 | 23 | 1.75 |
| 5 | VPro + Shield (Low pH, low concentration) | 4.2 | 23 | 1.75 |
| 6 | VPro + VPF (Midpoint pH, low concentration) | 5.0 | 23 | 1.75 |
| 7 | VPro alone (High pH, low concentration) | 6.0 | 23 | 1.75 |
| 8 | VPro + Shield H (High pH, low concentration) | 6.0 | 23 | 1.75 |
| 9 | VPro + X0SP (Midpoint pH, low concentration) | 5.0 | 23 | 1.75 |
| 10 | VPro + X0SP (Low pH, low concentration) | 4.2 | 23 | 1.75 |
| 11 | VPro + X0SP (low pH, High Conc.) | 4.2 | 23 | 7 |
| 12 | VPro + Shield (Low pH, High Conc.) | 4.2 | 28 | 7 |
| 13 | VPro + Shield (High pH, High Conc.) | 6.0 | 28 | 7 |
| 14 | VPro + Shield H (Low pH High Con,) | 4.2 | 28 | 7 |
| 15 | VPro + Shield H (High pH High Conc) | 6.0 | 28 | 7 |
| 16 | VPro + X0SP (High pH, High Conc.) | 6.0 | 28 | 7 |

Figure 7:
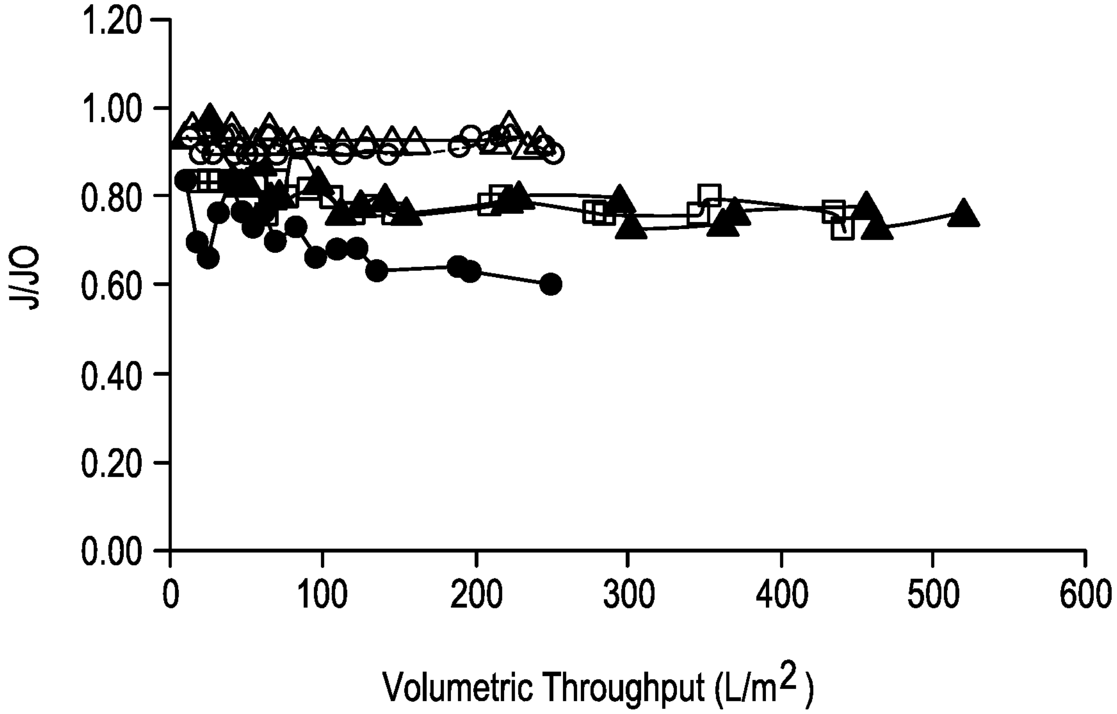
FIG. 7: BiTE® A Hydraulic Performance at midpoint pH, low concentration, low conductivity conditions (pH 5.0, 23 mS/cm, 1.75 g/L). VPro alone [solid black circle], VPro+Shield [solid black triangle], VPro+Shield H [open square], VPro+VPF [solid grey circles], and VPro+X0SP [open black triangle].
Figure 8:
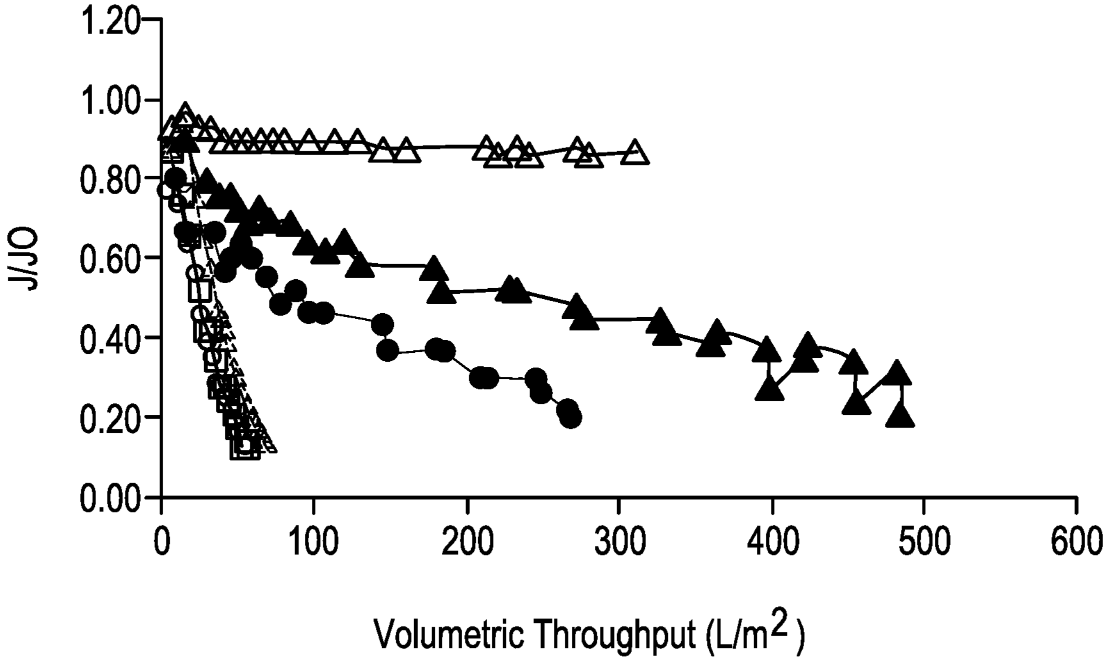
FIG. 8: BiTE A® Hydraulic Performance at low pH, high and low concentration and conductivity conditions (pH 4.2, 23 or 28 mS/cm, 1.75 or 7 g/L). VPro [solid black circle], VPro+X0SP low pH [open black triangle], VPro+Shield low pH [solid black triangle], VPro+X0SP high concentration, low pH [solid grey triangle], VPro+Shield H high concentration, low pH [Open circle], VPro+Shield high concentration, low pH [black open square]
Figure 9:
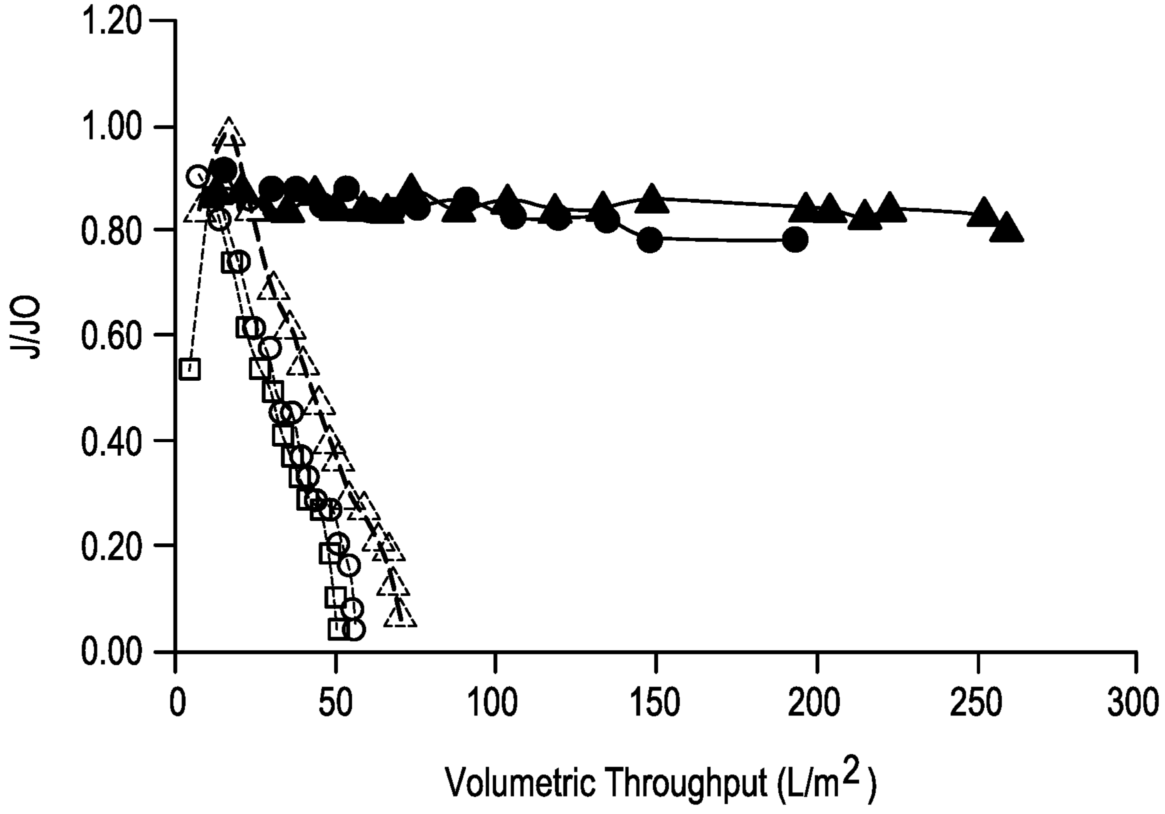
FIG. 9: BiTE A® Hydraulic Performance at high pH, low and high concentration and conductivity conditions (pH 6.0, 23 or 28 mS/cm, 1.8 or 7 g/L). VPro [closed circle], VPro+Shield H high pH, low concentration [closed triangle], VPro+X0SP [gray closed triangle] high pH, high concentration, VPro+Shield H [open circle] high pH, high concentration, VPro+Shield [open square] high pH, high concentration.

FIGS. 7-9 show the hydraulic performance of each run separated by feed condition. Results are displayed in terms of normalized flux decay (compared to buffer permeability) as a function of volumetric throughput (L/$m^2$). Table 11 and FIGS. 7-9 present a summary of the filtration results. Table 12 present a summary of the product quality attributes HMW % (SEC), clips % (rCE) and charge profile, acidic and basic (CEX).

TABLE 11

| Run | Run/ Conditions | Throughput (L/m²) | % Flux decay |
|---|---|---|---|
| | Volumetric Throughput data for all BiTE ® A runs | | |
| 1 | VPro (1.75 g/L, pH 5, 23 mS/cm) | 248.7 | 40.0 |
| 2 | Shield + VPro (1.75 g/L, pH 5, 23 mS/cm) | 519.4 | 23.7 |
| 3 | Shield H + VPro (1.75 g/L, pH 5, 23 mS/cm) | 441.3 | 27.7 |
| 4 | VPro (1.75 g/L, pH 4.2, 23 mS/cm) | 268.7 | 80.0 |
| 5 | Shield + VPro (1.75 g/L, pH 4.2, 23 mS/cm) | 484.5 | 79.3 |
| 6 | VPF + VPro (1.75 g/L, pH 5, 23 mS/cm) | 252.3 | 10.8 |
| 7 | VPro (1.75 g/L, pH 6, 23 mS/cm) | 195.0 | 21.8 |
| 8 | Shield H + VPro (1.75 g/L, pH 6, 23 mS/cm) | 258.7 | 19.5 |
| 9 | X0SP + VPro (1.75 g/L, pH 5, 23 mS/cm) | 242.3 | 7.4 |
| 10 | X0SP + VPro (1.75 g/L, pH 4.2, 23 mS/cm) | 311.9 | 13.4 |
| 11 | X0SP + VPro (7 g/L, pH 4.2, 23 mS/cm) | 67.7 | 85.5 |
| 12 | Shield + VPro (7 g/L, pH 4.2, 23 mS/cm) | 58.7 | 87.9 |
| 13 | Shield + VPro (7 g/L, pH 6, 28 mS/cm) | 50.6 | 95.9 |
| 14 | Shield H + VPro (7 g/L, pH 4.2, 28 mS/cm) | 58.1 | 87.8 |
| 15 | Shield H + VPro (7 g/L, pH 6, 28 mS/cm) | 55.5 | 95.9 |
| 16 | X0SP + VPro (7 g/L, pH 6, 28 mS/cm) | 69.4 | 92.7 |

Product Quality Results:

TABLE 12

| Sample conditions | SEC HMW % | rCE (Clips %) | CEX (Acidic) | CEX (Basic) |
|---|---|---|---|---|
| Product quality for BiTE ® A [SEC, CEX and rCE assays] | | | | |
| (1) VPro (pH 5, 1.75 g/L, 23 mS/cm) | 2.93 | 2 | 3.30 | 18.5 |
| (2) Shield + VPro (1.75 g/L, pH 5, 23 mS/cm) | 2.53 | 2.2 | 3.30 | 18.6 |
| (3) Shield H + VPro (1.75 g/L, pH 5, 23 mS/cm) | 2.87 | 2.2 | 3.30 | 18.7 |
| (4) VPro (pH 1.75 g/L, 4.2, 23 mS/cm) | 3.09 | 2.2 | 3.30 | 18.8 |
| (5) Shield + VPro (pH 1.75 g/L, 4.2, 23 mS/cm) | 2.85 | 2.4 | 3.30 | 18.8 |
| (6) VPF + VPro (1.75 g/L, pH 5, 23 mS/cm) | 2.37 | 3 | 3.20 | 18.2 |
| (7) VPro (1.75 g/L, pH 6, 23 mS/cm) | 2.97 | 2.2 | 3.40 | 18.5 |
| (8) Shield H + VPro (1.75 g/L, pH 6, 23 mS/cm) | 2.82 | 2.3 | 3.30 | 18 |
| (9) X0SP + VPro (1.75 g/L, pH 5, 23 mS/cm) | 0.92 | 2.4 | 3.30 | 17.9 |
| (10) X0SP + VPro (pH 1.75 g/L, 4.2, 23 mS/cm) | 2.47 | 3.4 | 3.50 | 19.3 |
| (11) X0SP + VPro (7 g/L, pH 4.2, 23 mS/cm) | 3.31 | 3.3 | 3.70 | 17.8 |
| (12) Shield + VPro (7 g/L, pH 4.2, 23 mS/cm) | 4.03 | 2.9 | 3.8 | 18.3 |
| (13) Shield + VPro (7 g/L, pH 6, 28 mS/cm) | 2.88 | 3.7 | 4.6 | 16.4 |
| (14) Shield H + VPro (7 g/L, pH 4.2, 28 mS/cm) | 4.54 | 2.2 | 3.6 | 18.3 |
| (15) Shield H + VPro (7 g/L, pH 6, 28 mS/cm) | 2.83 | 2.8 | 4.3 | 16.2 |
| (16) X0SP + VPro (7 g/L, pH 6, 28 mS/cm) | 0.70 | 2.1 | 4.7 | 15.3 |
| VPro load PQ for BiTE ®A | | | | |
| (A) 1.75 g/L, pH 5, 23 mS/cm, | 2.96 | 2.4 | 4.1 | 16.7 |
| (B) 7 g/L, pH 4.2, 23 mS/cm | 3.84 | 2.6 | 4.1 | 17.1 |
| (C) 7 g/L, pH 4.2, 28 mS/cm | 4.40 | 3.2 | 4.1 | 17.0 |
| (D) 7 g/L, pH 6, 28 mS/cm | 2.92 | 2.6 | 4.8 | 15.9 |

Results

1) Midpoint pH, Low Concentration, and Low Conductivity for BiTE® a (pH 5, Conductivity 23 mS/Cm, 1.75 g/L)

Hydraulic Performance

The viral filter alone, and in combination with the surface modified membrane prefilters and depth filters, Shield, Shield H, VPF, and X0SP, were tested at the midpoint pH, low concentration and low conductivity conditions for BiTE® A (pH 5, conductivity 23 mS/cm, 1.75 g/L), Runs 1-3, 6 and 9, Table 10. The viral filter in combination with a depth filter (VPF or X0SP) reached a steady state at ~10% flux decay. The viral filter in combination with a surface modified membrane filter (Shield or Shield H) showed more initial fouling, but also reached steady state at ~25-30% flux decay. The viral filter alone, without a surface modified membrane prefilter or depth filter had a throughput of 250 L/m², with an observed flux decay of 40%. See Table 11 Runs 1-3, 6 and 9, FIG. 7.

Product Quality

Of the combinations tested, the viral filter in combination with a depth filter (X0SP) had the greatest impact on product quality, reducing the aggregate (HMW %) level to 0.9%. See Table 12 Runs 1-3, 6 and 9, FIGS. 10A, 10C, 10E, 10G, load quality, Table 12 row (A).

2) Low pH, Low Concentration, Low Conductivity Conditions (pH 4.2, 23 mS/Cm, 1.75 g/L)

Hydraulic Performance

The viral filter alone or in combination with a depth filter (X0SP) and a surface modified prefilter (Shield) was tested at the low pH, low concentration, and low conductivity conditions (pH 4.2, 23 mS/cm, 1.75 g/L), Runs 4, 5, and 10, Table 10. The low pH condition had a minor effect on the combination of the viral filter and depth filter, reducing the flux decay to ~15% at 300 L/m2 and showing some mild fouling. The viral filter alone, and the combination with the surface modified prefilter, experienced 80% flux decay and showed significant fouling at the low pH condition. See Table 11 Runs 4, 5, and 10, FIG. 8.

Product Quality

Due to better aggregate removal capability, the flux decay for the combination of the viral filter and depth filter was just 15%, as compared to the viral filter alone or the viral filter in combination with the surface modified prefilter, which each had an 80% flux decay. Clip and charge profile were similar across the various combinations, see Table 12 Runs 4, 5, and 10 FIGS. 10A, 10C, 10E, and 10G.

3) High pH, Low Concentration, Low Conductivity (1.75 g/L, pH 6, 23 mS/Cm)

Hydraulic Performance

The viral filter alone or in combination with a surface modified prefilter (Shield H) were tested at low concentration, high pH, low conductivity conditions (1.75 g/L, pH 6, 23 mS/cm), Table 10 Runs 7 and 8. Both the viral filter alone or in combination with the surface modified prefilter had about a 20% flux decay.

Product Quality

The combination of the viral filter and the surface modified prefilter was no better in removing aggregates than the viral filter alone. The charge profile and clips were similar across both combinations.

See Table 12 Runs 7 and 8, FIGS. 10A, 10C, 10E, 10G.

4) Low pH, High Conductivity, High Concentration (7 g/L, pH 4.2, 23 mS/Cm)

Hydraulic Performance

The viral filter in combination with a depth filter (X0SP) and two surface-modified prefilters (Shield, and Shield H) were tested at the low pH and high concentration conditions, 7 g/L, pH 4.2, 23 mS/cm, see Table 10 Runs 11, 12 and 14. All three combinations experienced over 80% flux decay, see Table 11 Runs 11, 12, and 14, FIG. 8.

Product Quality

Figure 10A:
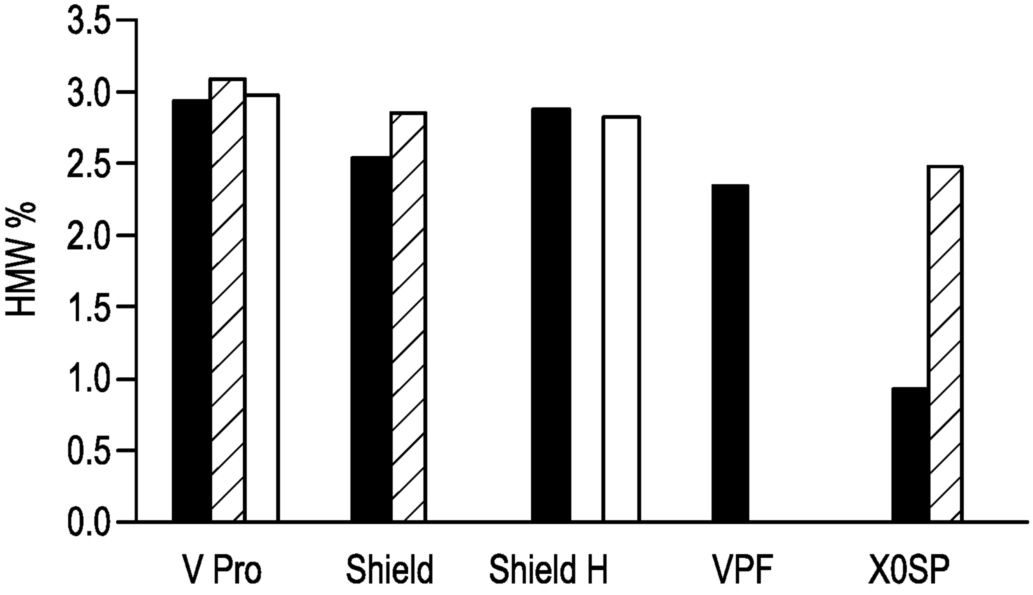
FIG. 10: A: HMW % Product quality data for Molecule A—1.75 g/L, pH 5 [black bars], pH 4.2 [grey bars] and pH 6.0 [patterned bars].
Figure 10B:
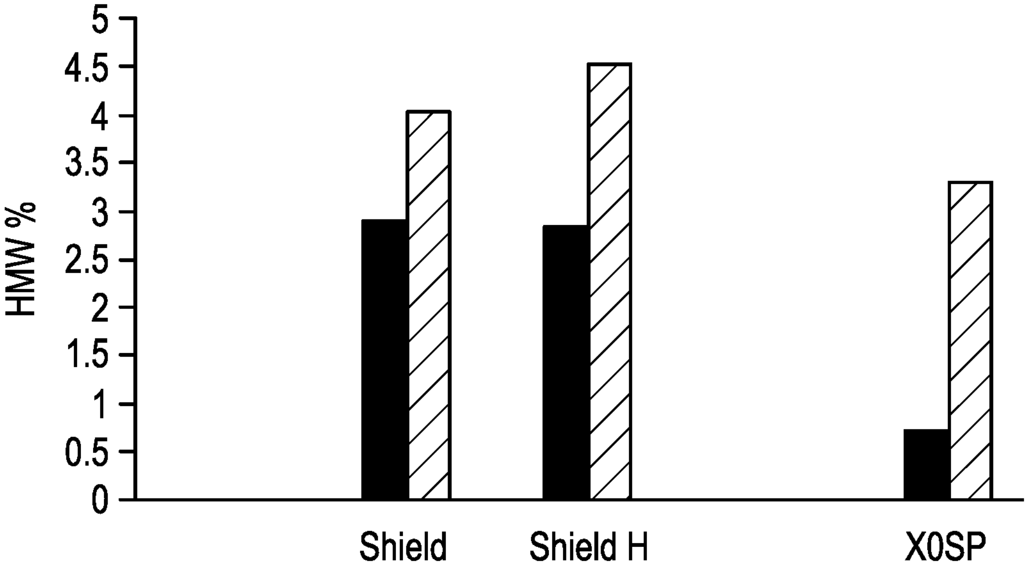
Figure 10C:
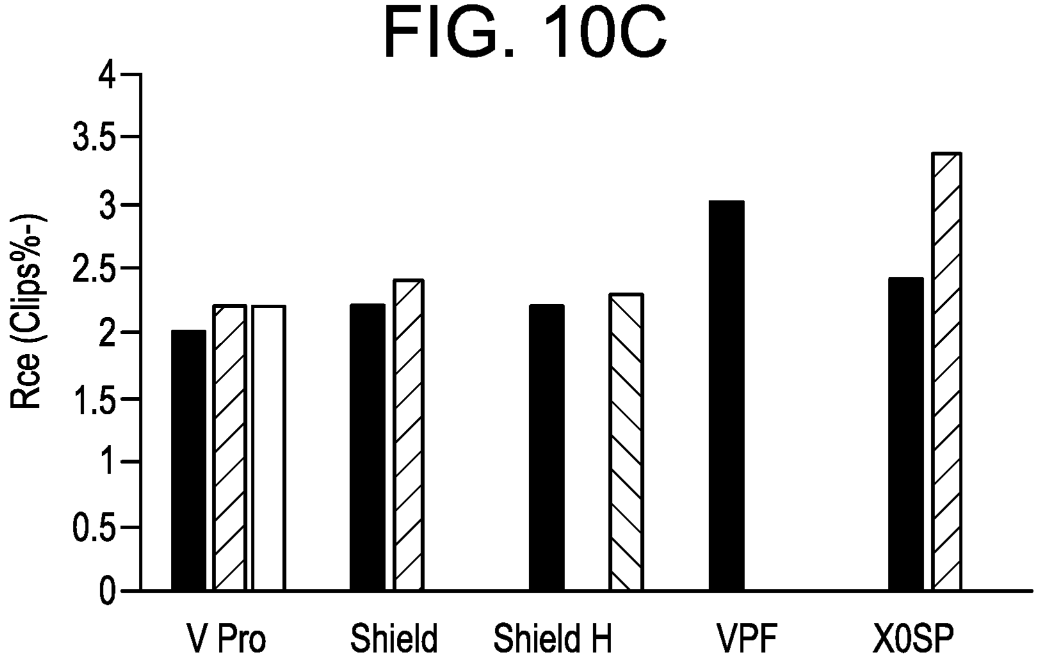
Figure 10D:
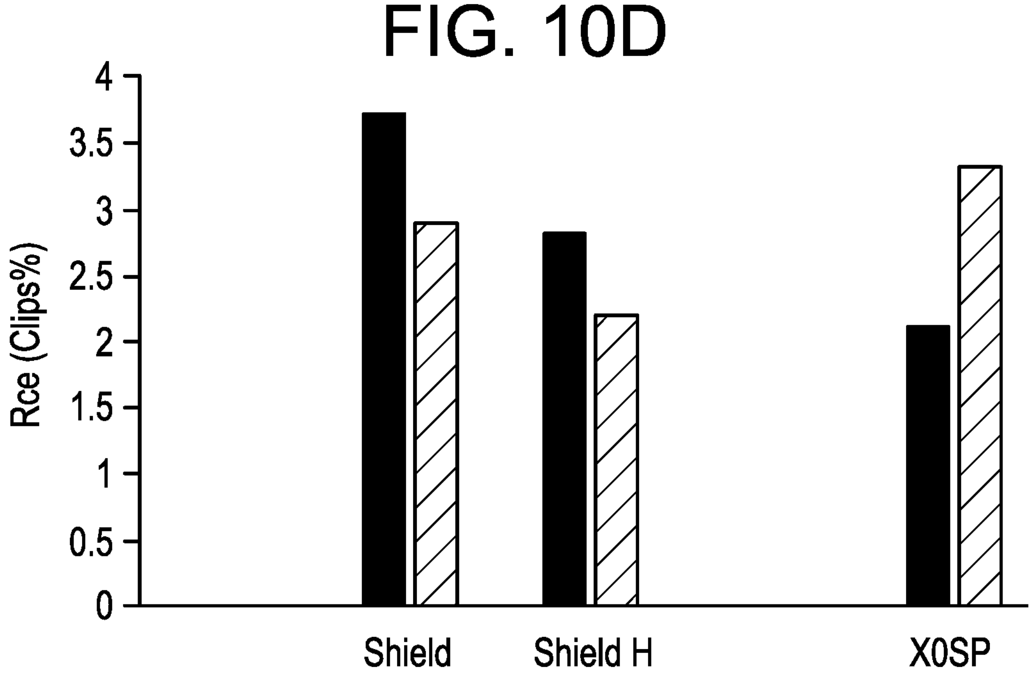
Figure 10E:
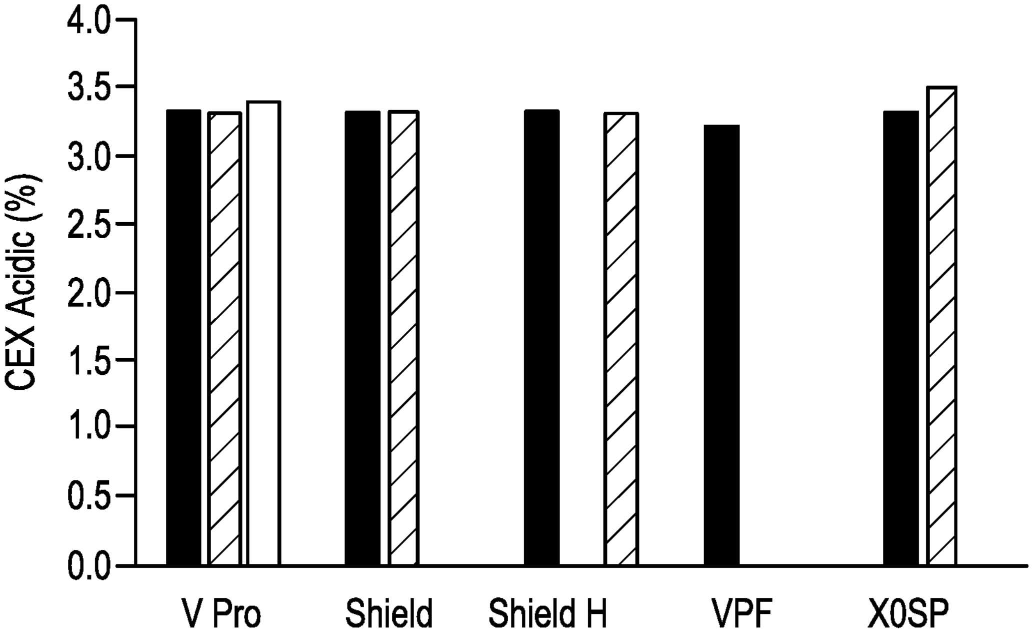
Figure 10F:
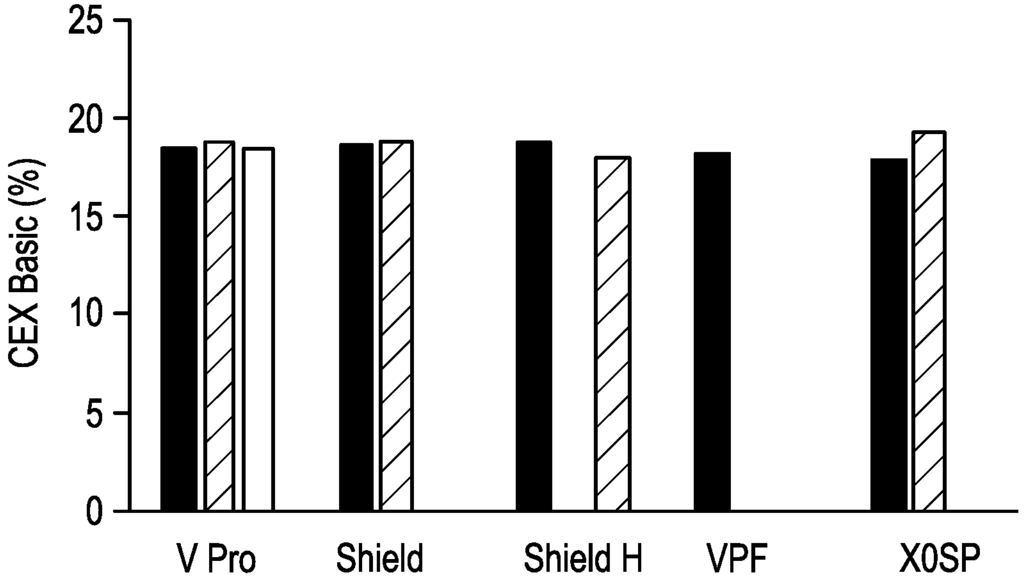
Figure 10G:
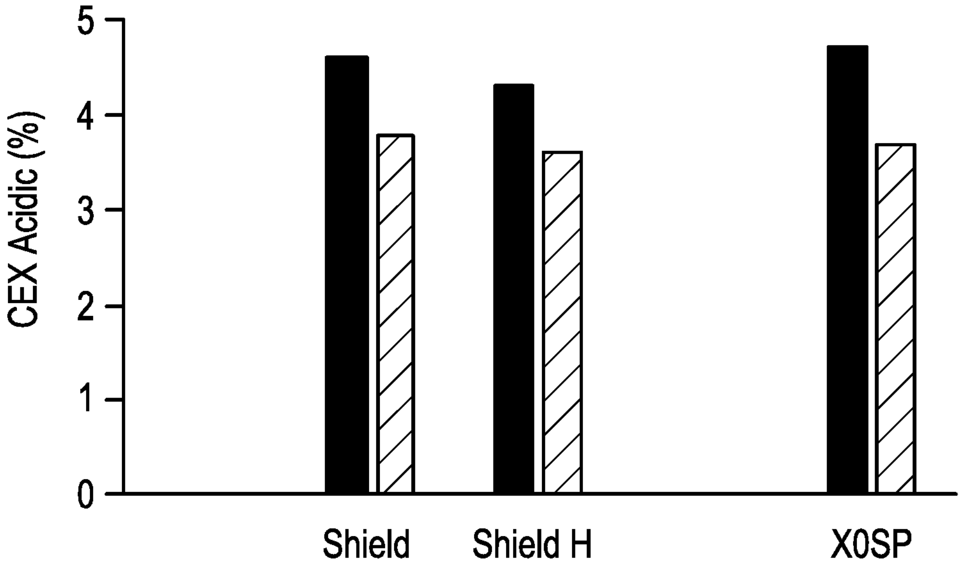
Figure 10H:
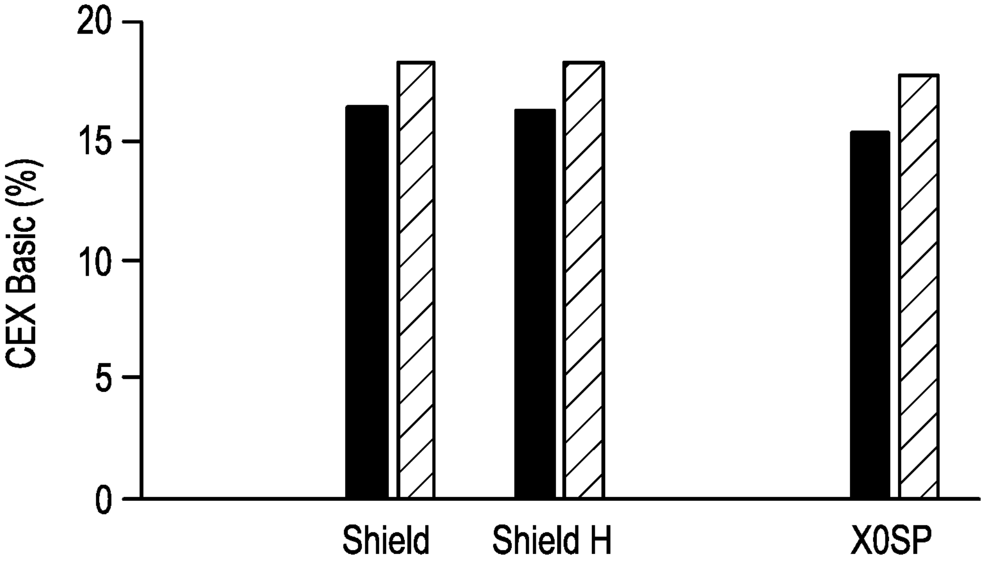

None of the combinations was more effective in removing the increase in aggregates created at these conditions, of the three, the combination of the viral filter and the prefilter was the best in removing aggregates, see Table 12 Runs 11, 12, and 14. The charge profile and clips were similar across the three prefilter conditions, see Table 12 Runs 11, 12, and 14, FIGS. 10B, 10D, and 10F, Table 12 rows (B) and (D).

5) High pH, High Conductivity, High Concentration (7 g/L, pH 6, 28 mS/Cm)

Hydraulic Performance

The viral filter, in combination with the synthetic depth filter (X0SP) and the two surface-modified prefilters (Shield, and Shield H), were tested at the high pH, high conductivity, and concentration conditions (7 g/L, pH 6, 28 mS/cm), see Table 10 Runs 13, 15 and 16. All three combinations had over 90% flux decay, see Table 11, FIG. 9 Runs 13, 15, and 16.

Product Quality

The combination of the viral filter and synthetic depth filter reduced aggregate levels to a significantly low level, 0.07%. reduced aggregate levels to a very low level, 0.07%, see Table 12 Runs 13, 15, and 16, FIGS. 10B, 10D, 10E, 10H, Table 12 row (C).

It was observed that when the concentrated feed of 7 g/L at the midpoint pH 5.0, and low conductivity (pH 5, 23 mS/cm, 3.8% aggregate level) was titrated to pH 6.0, and high conductivity (28 mS/cm), the aggregates were lower in comparison to titrating to a low pH 4.2, high and high conductivity (28 mS/cm). At pH 6.0, the load aggregate level was 2.92% as compared to 4.4% at the low pH (pH 4.2). conditions. It is probable that there is a maximum threshold aggregate level from which the viral filter in combination with the depth filter (X0SP) can reduce, and that could be the reason that at high pH the filter could still reduce the aggregate levels, although the flux is still high. But at low pH it is beyond a theoretical maximum level.

Example 6 Viral Filtration Comparing a Bispecific T Cell Engager and a Monoclonal Antibody A half-life extended bispecific T cell engager, BiTE® A, and a monoclonal antibody, Mab A, were compared with respect to process and product quality performance using a combination of a viral filter and depth filter. For BiTE® A and Mab A, the viral filter was a Viresolve® Pro (VPro), polyethersulfone (PES) (3.1 $cm^2$) pavovirus retentive filter, tested in combination with an absorptive depth filter, Viresolve® Prefilter, (VPF) (5 $cm^2$), both from MilliporeSigma (Burlington, Mass.).

BiTE® A was also tested using the combination of the VPro viral filter and a synthetic depth filter, Millistak+® HC Pro X0SP (X0SP) (5 $cm^2$/3.1 $cm^2$), both from MilliporeSigma (Burlington, Mass.).

The BiTE® A load concentration was low concentration, 1.75 g/L, midpoint pH 5.0, and midpoint conductivity 23 mS/cm, see Example 5, runs 6 and 9. For Mab A, an eluate pool containing Mab A was adjusted to midpoint pH 6.7, conductivity 20 mS/cm, and a load concentration of 12.4 g/L.

Hydraulic Performance

For Mab A, the combination of the viral filter and absorptive depth filter was able to achieve >1000 L/$m^2$ with approximately ~ 40% flux decay (4 hours processing time), while BiTE® A, with either viral filter/pre-filter combination, was able to achieve >250 L/$m^2$, but with approximately ~ 10% flux decay. Due to feed limitations, further data for BiTE® A could not be obtained. FIG. 11 shows the normalized flux decay as a function of volumetric throughput (L/$m^2$), for the pH and feed stream concentrations. At low concentration and mid to high pH [5 or greater], BiTE A (and even BiTE B in Example 7), the volumetric throughput obtained is similar to an antibody when using a VPF or a synthetic prefilter.

Product Quality

For Mab A, samples of the load pool and viral filtrate pool showed practically no difference in HMW %. For BiTE® A, the combination of the viral filter and the synthetic depth filter reduced aggregate level (HMW %) in the viral filter pool, see Table 12 Run 9 and row (A).

BiTE® A was also tested a higher load concentration, pH and conductivity, 7 g/L, pH, 6.0, and 28 mS/cm, using the combination of the VPro viral filter and synthetic depth filter, (X0SP), as described in Example 5, Run 16. FIG. 11 shows the normalized flux decay as a function of volumetric throughput (L/$m^2$), for the high pH and high feed stream concentration for both. For the Mab A, the load pool and viral filtrate pool showed practically no difference in HMW %. For the higher concentration and pH BiTE® A, the combination of the viral filter and the synthetic depth filter was able to significantly reduce aggregate level in the viral filtrate pool, see Table 12 Run 16 and row (D), FIG. 10A.

It was easier to filter the feed stream containing Mab A (12.7 g/L) at midpoint pH (6.7) and conductivity (20 mS/cm), to achieve a relatively high volumetric throughput with minimal flux decay as compared to the high concentration BiTE® A (7 g/L) at high pH (6.0) and conductivity (28 mS/cm), which had less volumetric throughput with significant flux decay, see Table 11, Runs 13, 15, and 16. It may be that at high concentrations, the aggregate content of BiTE® A is different compared to Mab A which had no change in aggregate (% HMW) content between the pre- and post-filtrate pool. For BiTE® A, the prefilter removed some of the aggregate, but some higher form of aggregate may remain behind which may be the cause of the low filterability.

The filterability of the low feed concentration, BiTE® A and Mab A was similar, see FIG. 11. However, even with a low feed concentration, the prefilters were able to remove some of the aggregates associated with BiTE® A and possibly the content of the remaining aggregates is such that the filterability of BiTE® A is relatively high with high volumetric throughput [>250 L/m$^2$] achieved at a smaller flux decay (10%), see FIG. 10A and Table 12, Run 9. With regard to BiTE®, the synthetic depth filter was very sensitive to removal of aggregate from the load, 2.96%, (see Table 12, row (A)), to 0.92% in the filtrate pool, (see Table 12, run 9), while the absorptive depth filter reduced to 2.37%, (see Table 12, Run 6), under the same conditions. The overall difference between the absorptive depth filter and the synthetic depth filter is that one is synthetic, the synthetic filter may be better suited for removing the types of aggregates formed by BiTEs® under these conditions.

Example 7 Viral Filtration Performance with BiTE® B

This experiment assessed the viral filtration in normal flow filtration under constant pressure mode and the effect of feed conditions [pH, conductivity and concentration] on viral filter hydraulic performance and product quality attributes in the presence and absence of various prefilters, for a half-life extended bispecific T cell engager (HLE BiTE® B) molecule feed stream, as described in Example 6.

As described in Example 6, a Viresolve® Pro (VPro), polyethersulfone (PES) (3.2 cm$^2$) parvoviral retentive viral filter, was tested alone and in combination with a surface modified, polyethersulfone, membrane prefilter, Viresolve® Pro Shield H (Shield H) (3.2 cm$^2$); and two depth filters, an adsorptive depth filter Viresolve® Prefilter, (VPF) (5 cm$^2$), and a synthetic depth filter Millistak+® HC Pro X0SP (X0SP, composed of double layer silica fiber aid with polyacrylic fiber) (5 cm$^2$), all from MilliporeSigma (Burlington, Mass.). Following virus filtration, BiTE® B was evaluated with respect to product quality and performance. The feed condition used in the experiments are shown in Table 13 and the run conditions based on the feed conditions, are provided in Table 14.

TABLE 13

| Feed Design conditions | | | | |
|---|---|---|---|---|
| Process Fluid | pH | Conductivity (mS/cm) | Concentration (g/L) | Buffer Components |
| BiTE ® B (mid point pH) | 5.9 | 31.36 | 1.81 | 100 mM MES/MES-Sodium, 290 mM NaCl |
| BiTE ® B (high conductivity) | 5.9 | 45 | 1.81 | 100 mM MES/MES-Sodium, 290 mM NaCl |
| BiTE ® B (low pH) | 4.2 | 31.36 | 1.81 | 100 mM MES/MES-Sodium, 290 mM NaCl |

TABLE 14

| Experimental run conditions | | | | |
|---|---|---|---|---|
| Run # | Filter Combination | pH | Conductivity (mS/cm) | Concentration (g/L) |
| 17 | VPro alone | 5.9 | 31.36 | 1.81 |
| 18 | Shield H + VPro | 5.9 | 31.36 | 1.81 |
| 19 | VPF + VPro | 5.9 | 31.36 | 1.81 |
| 20 | X0SP + VPro | 5.9 | 31.36 | 1.81 |
| 21 | Shield H + VPro | 5.9 | 45 | 1.81 |
| 22 | X0SP + VPro | 5.9 | 45 | 1.81 |
| 23 | Shield H + VPro | 4.2 | 31.36 | 1.81 |
| 24 | X0SP + VPro | 4.2 | 31.36 | 1.81 |

The product quality profile for BiTE® B was only obtained for the high molecular weight aggregates in the viral filtrate pool, Table 16. For the midpoint pH and low conductivity condition (pH 5.9, 1.81 g/L, 31.36 mS/cm), Table 14 Runs 17-20, the combination of the viral filter and the synthetic depth filter (X0SP) removed a higher percent of aggregates compared to the combination of the viral filter with the absorptive depth filter (VPF) or the surface-modified prefilter (Shield H) (Table 15 Runs 17-20). The combination of the viral filter with either prefilter did not result in significant flux decay (see FIG. 13, Table 15 Runs 17-20).

For the low pH, low conductivity condition (1.81 g/L, pH 4.2, 31.36 mS/cm) (Runs 23, 24), the combination of the viral filter and synthetic depth filter only had a 20% flux decay, compared to a flux decay of 80% for the combination of the viral filter and the surface-modified prefilter (see FIG. 14, Table 15 Runs 23-24). From a product quality perspective, the viral filter in combination with the synthetic depth filter was slightly better at removing high molecular weight aggregates (1.6%), (see Table 16, Run 24), compared to the viral filter in combination with the surface-modified prefilter (2.1%) (Table 16 Runs 23-24), see FIG. 15.

For the high pH, high conductivity condition (1.81 g/L, pH 5.9, 45 mS/cm), Table 14 Runs 21-22, the viral filter in combination with either the synthetic depth filter or the surface-modified prefilter had very low flux decay, 3.7% and 5.2%, (see FIG. 14, Table 15 Runs 21-22), however, from a product quality perspective, the combination of the viral filter with the synthetic prefilter fared very well in removing high molecular weight aggregates to a final value of 0.3% as compared to 1.8% for the combination of the viral filter with the surface-modified prefilter which was not very effective (see Table 16 Runs 21-22, FIG. 15). The higher conductivity did not appear to alter the hydraulic performance and aggregate removal performance significantly the midpoint pH, low conductivity condition (Table 16 Run 20 compared to Run 22).

TABLE 15 shows a summary of the volumetric throughput and % flux decay

| Run | Conditions | Throughput ($L/m^2$) | % Flux decay |
|---|---|---|---|
| 17 | VPro alone (1.81 g/L, pH 5.9, 31.36 mS/cm) | 323.0 | 20.9 |
| 18 | VPro + Shield H (1.81 g/L, pH 5.9, 31.36 mS/cm) | 319.8 | 6.9 |
| 19 | VPro + VPF (1.81 g/L, pH 5.9, 31.36 mS/cm) | 313.4 | 9.1 |
| 20 | VPro + X0SP (1.81 g/L, pH 5.9, 31.36 mS/cm) | 315.0 | 6.3 |
| 21 | VPro + Shield H (1.81 g/L, pH 5.9, 45 mS/cm) | 109.7 | 5.2 |
| 22 | VPro + X0SP (1.81 g/L, pH 5.9, 45 mS/cm) | 316.2 | 3.7 |
| 23 | VPro + Shield H (1.81 g/L, pH 4.2, 31.36 mS/cm) | 196.1 | 82.6 |
| 24 | VPro + X0SP (1.81 g/L, pH 4.2, 31.36 mS/cm) | 311.0 | 19.8 |

TABLE 16

Product Quality results

| Run # | Condition type | SE-HPLC HMW % | SE-HPLC MAIN % |
|---|---|---|---|
| 17 | VPro alone (1.81 g/L, pH 5.9, 31.36 mS/cm) | 1.9 | 98.1 |
| 18 | VPro + Shield H (1.81 g/L, pH 5.9, 31.36 mS/cm) | 1.9 | 98.1 |
| 19 | VPro + VPF (1.81 g/L, pH 5.9, 31.36 mS/cm) | 1.3 | 98.7 |
| 20 | VPro + X0SP (1.81 g/L, pH 5.9, 31.36 mS/cm) | 0.5 | 99.5 |
| 21 | VPro + Shield H (1.81 g/L, pH 5.9, 45 mS/cm) | 1.8 | 98.2 |
| 22 | VPro + X0SP (1.81 g/L, pH 5.9, 45 mS/cm) | 0.3 | 99.7 |
| 23 | VPro + Shield H (1.81 g/L, pH 4.2, 31.36 mS/cm) | 2.1 | 97.9 |
| 24 | VPro + X0SP (1.81 g/L, pH 4.2, 31.36 mS/cm) | 1.6 | 98.4 |

For BiTE B, at mid-point pH conditions, the viral filter alone was able to provide a good volumetric throughput at relatively low flux decay, addition of a prefilter reduced the flux decay. However, the synthetic prefilter reduced aggregates significantly. At mid-point pH and high conductivity, both surface modified and synthetic depth prefilters performed well with high volumetric throughput achieved at low flux decays, but only the synthetic depth filter was able to significantly remove aggregates.

At low pH and low conductivity, only synthetic depth filter provided high volumetric throughput with minimal flux decay, while the surface modified prefilter suffered significant flux decay, and throughput achieved was relatively smaller compared to synthetic depth prefilter. At this condition, none of the prefilters tested were able to remove aggregates significantly.

What is claimed is:

1. An integrated, continuous method for producing a recombinant biologic therapeutic comprising a) providing a solution of a purified recombinant protein of interest;

b) concentrating or diluting the purified recombinant protein by ultrafiltration;

c) buffer exchanging the purified recombinant protein resulting from step b) by diafiltration into a buffer comprising one or more pharmaceutically acceptable carriers;

d) further diluting or concentrating the solution resulting from step c) by ultrafiltration in an ultrafiltration and diafiltration retentate tank;

e) after ultrafiltration and diafiltration in steps b)-d), adding a non-ionic detergent or surfactant directly to the ultrafiltration and diafiltration retentate tank, resulting in a bulk drug substance;

f) filtering the bulk drug substance to reduce bioburden, resulting in a bulk drug product;

g) transferring the bulk drug product of f) to a filling station;

h) sterile filtering the bulk drug product, resulting in a sterile bulk drug product;

i) filling a primary drug product container with the sterile bulk drug product; and j) sealing, labeling and packaging the primary drug product container;

wherein neither the purified recombinant protein nor the bulk drug substance is subjected to freezing and thawing.

2. The method according to claim 1, wherein the non-ionic detergent or surfactant is a poly-oxy-ethylene (PEO)-based surfactant.

3. The method according to claim 1, wherein the non-ionic detergent or surfactant is selected from polysorbate 80 and polysorbate 20.

4. The method according to claim 1, wherein the concentration of the non-ionic detergent or surfactant is from 0.001 to 0.1% (weight/volume).

5. The method according to claim 1, wherein transferring in step g) is to an aseptic processing facility.

6. The method according to claim 5, wherein the filling in step i) uses at least one gloveless, sterile isolator.

7. The method according to claim 1, wherein the solution from step c) is diluted in step d) by ultrafiltration.

8. The method according to claim 1, wherein the solution from step c) is concentrated in step d) by ultrafiltration.

9. The method according to claim 1, wherein the ultrafiltration in steps b) and d) is performed using a stabilized cellulose based hydrophilic membrane, loading up to 72 $g/m^2$ of membrane area.

10. The method according to claim 1, wherein the ultrafiltration in step b) is performed using a stabilized based hydrophilic membrane at target concentration less than or equal to 3.20 mg/ml.

11. The method according to claim 1, wherein the ultrafiltration in step b) is performed using a stabilized cellulose based hydrophilic membrane at a target overconcentration of 1.1x to 2.5x the initial concentration.

12. The method according to claim 1 wherein the ultrafiltration and diafiltration in steps b)-d) is performed using a regenerated cellulose, alkali stable membrane loaded up to 170 g/$m^2$ of membrane area.

13. The method according to claim 1, wherein the ultrafiltration and diafiltration in steps b)-d) is performed using a regenerated cellulose, alkali stable membrane at an intermediate target overconcentration of less than or equal to 9 g/L after the ultrafiltration in step b, with up to 13 diavolumes of the buffer in step c.

14. The method according to claim 1, further comprising filtering with at least one viral filter following step e) and before step f).

15. The method according to claim 14, wherein the purified recombinant protein of interest is a bispecific T cell engager, and the bispecific T cell engager has a formulation concentration of 5 g/L or less in the bulk drug substance in step e).

16. The method according to claim 14, wherein the viral filter is selected from a hydrophilized polyvinylidene fluoride (PVDF) hollow fiber filter, a cuprammonium-regenerated cellulose hollow fiber filter, or a polyethersulfone (PES) parvovirus retentive filter.

17. The method according to claim 14, wherein at least one viral filter also includes a prefilter.

18. The method according to claim 17, wherein the prefilter is a depth filter.

19. The method according to claim 1, wherein one or more additional purified recombinant proteins of interest or drug substances are added prior to step g).

20. The method according to claim 1, wherein the purified protein of interest is an antigen-binding protein.

21. The method according to claim 20, wherein the antigen-binding protein is a multispecific protein.

22. The method according to claim 21, wherein the multispecific protein is a bispecific antibody.

23. The method according to claim 22, wherein the bispecific antibody is a bispecific T cell engager.

24. The method according to claim 23, wherein the bispecific T cell engager is a half life extended bispecific T cell engager.

25. The method according to claim 23, wherein one binding domain of the bispecific T cell engager is specific for a tumor-associated surface antigen on target cell selected from EGFRVIII, MSLN, CDH19, DLL3, CD19, CD33, CD38, FLT3, CDH3, BCMA, PSMA, MUC17, CLDN18.2, or CD70.

26. A method for producing a recombinant protein drug product comprising a) expanding cells expressing a protein of interest;
b) inoculating and/or feeding a bioreactor with the expanded cells and cultivating the cells to express a recombinant protein of interest;
c) recovering the recombinant protein in a harvested recombinant protein solution;
d) purifying the recombinant protein from the harvested recombinant protein solution through capture chromatography;
e) purifying the recombinant protein through polish chromatography, resulting in a purified recombinant protein solution;
f) subjecting the purified recombinant protein solution to ultrafiltration and diafiltration, the ultrafiltration and diafiltration comprising
   concentrating or diluting the purified recombinant protein by ultrafiltration;
   buffer exchanging the purified recombinant protein by diafiltration into a buffer comprising one or more pharmaceutically acceptable carriers; and
   further diluting or concentrating the purified recombinant protein solution by ultrafiltration in an ultrafiltration and diafiltration tank,
g) after diafiltration and ultrafiltration in step f), adding a non-ionic detergent or surfactant directly to the ultrafiltration and diafiltration retentate tank containing the purified recombinant protein solution, resulting in a drug substance;
h) filtering the drug substance to reduce bioburden, resulting in a filtered bulk drug product;
i) transferring the bulk drug product of h) to a filling station;
j) sterile filtering the bulk drug product, resulting in a sterile bulk drug product;
k) filling a primary drug product container with sterile bulk drug product; and
1) sealing, labeling and packaging the primary drug product container;

wherein neither the recombinant protein nor the drug substance is subjected to freezing and thawing.

* * * * *